United States Patent [19]

Matsuo et al.

[11] Patent Number: 5,164,372
[45] Date of Patent: Nov. 17, 1992

[54] PEPTIDE COMPOUNDS HAVING SUBSTANCE P ANTAGONISM, PROCESSES FOR PREPARATION THEREOF AND PHARMACEUTICAL COMPOSITION COMPRISING THE SAME

[75] Inventors: Masaaki Matsuo, Toyonaka; Daijiro Hagiwara, Moriguchi; Hiroshi Miyake, Kyoto, all of Japan

[73] Assignee: Fujisawa Pharmaceutical Company, Ltd., Osaka, Japan

[21] Appl. No.: 505,457

[22] Filed: Apr. 6, 1990

[30] Foreign Application Priority Data

Apr. 28, 1989 [GB] United Kingdom ............... 8909795
Aug. 1, 1989 [GB] United Kingdom ............... 8917542

[51] Int. Cl.$^5$ ............ A61K 37/00; A61K 37/02; C07K 5/00; C07K 7/00
[52] U.S. Cl. .............................. 514/19; 514/18; 514/17; 530/330
[58] Field of Search ............ 548/467; 514/17, 19, 514/18; 530/314, 330

[56] References Cited

U.S. PATENT DOCUMENTS

| | | | |
|---|---|---|---|
| 4,228,077 | 10/1980 | Ondetti et al. | |
| 4,254,107 | 3/1981 | Veber et al. | 424/177 |
| 4,404,135 | 9/1983 | Jones | 530/302 |
| 4,680,283 | 7/1987 | Veber et al. | 514/17 |
| 4,791,102 | 12/1988 | Bernat et al. | 514/19 |
| 4,839,465 | 6/1989 | Singh et al. | 530/330 |

Primary Examiner—Lester L. Lee
Assistant Examiner—A. M. Davenport
Attorney, Agent, or Firm—Oblon, Spivak, McClelland, Maier & Neustadt

[57] ABSTRACT

Peptide compounds having Substance P antagonism of the formula:

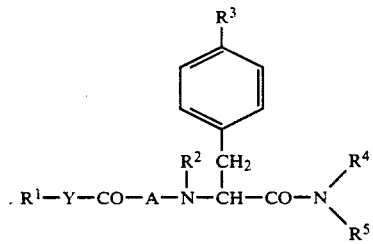

wherein $R^1$ is lower alkyl, aryl, arylamino, pyridyl, pyrrolyl, pyrazolopyridyl, quinolyl, or a group of the formula:

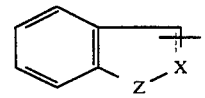

wherein the symbol of a line and dotted line is a single bond or a double bond; X is CH or N; Z is O, S or NH; $R^2$ is hydrogen or lower alkyl; $R^3$ is hydrogen or hydroxy; $R^4$ is lower alkyl which may have suitable substituent(s); $R^5$ is ar(lower)alkyl which may have suitable substituent(s) or pyridyl(lower)alkyl, or $R^4$ and $R^5$ are linked together to form benzene-condensed lower alkylene; A is an amino acid residue excepting D-Trp, which may have suitable substituent(s); and Y is bond, lower alkylene or lower alkenylene;

and their pharmaceutically acceptable salts are disclosed.

10 Claims, No Drawings

PEPTIDE COMPOUNDS HAVING SUBSTANCE P ANTAGONISM, PROCESSES FOR PREPARATION THEREOF AND PHARMACEUTICAL COMPOSITION COMPRISING THE SAME

The present invention relates to new peptide compounds and pharmaceutically acceptable salt thereof.

More particularly, it relates to new peptide compounds and pharmaceutically acceptable salts thereof which have pharmacological activities such as tachykinin antagonism, especially substance P antagonism, neurokinin A antagonism, neurokinin B antagonism, and the like, to processes for preparation thereof, to pharmaceutical composition comprising the same, and to a use of the same as a medicament.

One object of the present invention is tm provide new and useful peptide compounds and pharmaceutically acceptable salts thereof which have pharmacological activities such as tachykinin antagonism, especially substance P antagonism, neurokinin A antagonism, neurokinin B antagonism, and the like.

Another object of the present invention is to provide processes for the preparation of said peptide compounds and salts thereof.

A further object of the present invention is to provide a pharmaceutical composition comprising, as an active ingredient, said peptide compounds and pharmaceutically acceptable salts thereof.

Still further object of the present invention is to provide a use of said peptide compound or a pharmaceutically acceptable salt thereof as tachykinin antagonist, especially substance P antagonist, neurokinin A antagonist or neurokinin B antagonist, useful for treating or preventing tachykinin mediated diseases, for example, respiratory diseases such as asthma, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, and the like; pains or aches (e.g., migraine, headache, toothache, cancerous pain, etc.); and the like in human being or animals.

The object compounds of the present invention can be represented by the following general formula (I).

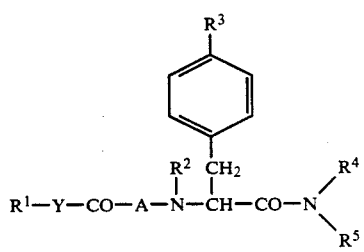

wherein
R¹ is lower alkyl, aryl, arylamino, pyridyl, pyrrolyl, pyrazolopyridyl, quinolyl, or a group of the formula:

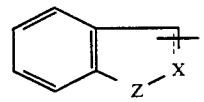

wherein
the symbol of a line and dotted line is a single bond or a double bond,
X is CH or N, and
Z is O, S or NH,
each of which may have suitable substituent(s);
R² hydrogen or lower alkyl;
R³ is hydrogen or hydroxy;
R⁴ is lower alkyl which may have suitable substituent(s), and
R⁵ is ar(lower)alkyl which may have suitable substituent(s) or pyridyl(lower)alkyl, or
R⁴ and R⁵ are linked together to form benzene-condensed lower alkylene;
A is an amino acid residue excepting D-Trp, which may have suitable substituent(s); and
Y is bond, lower alkylene or lower alkenylene.

According to the present invention, the new peptide compounds (I) can be prepared by processes which are illustrated in the following schemes.

Process 1

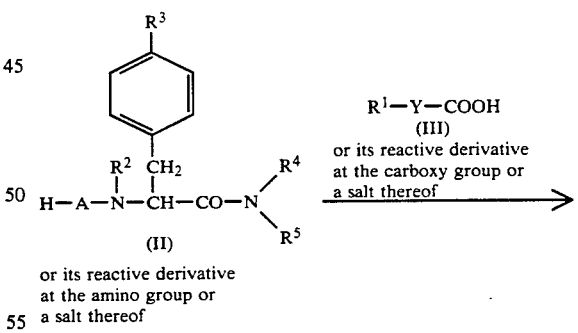

or its reactive derivative at the amino group or a salt thereof

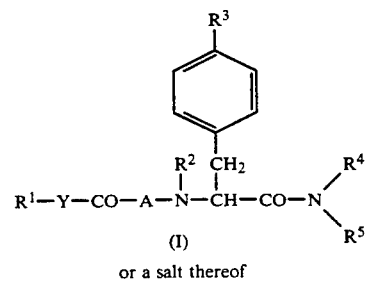

or a salt thereof

Process 2
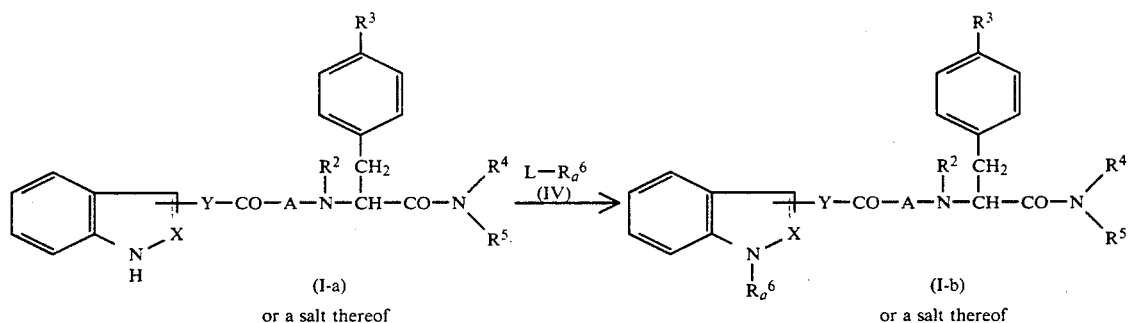
Process 3
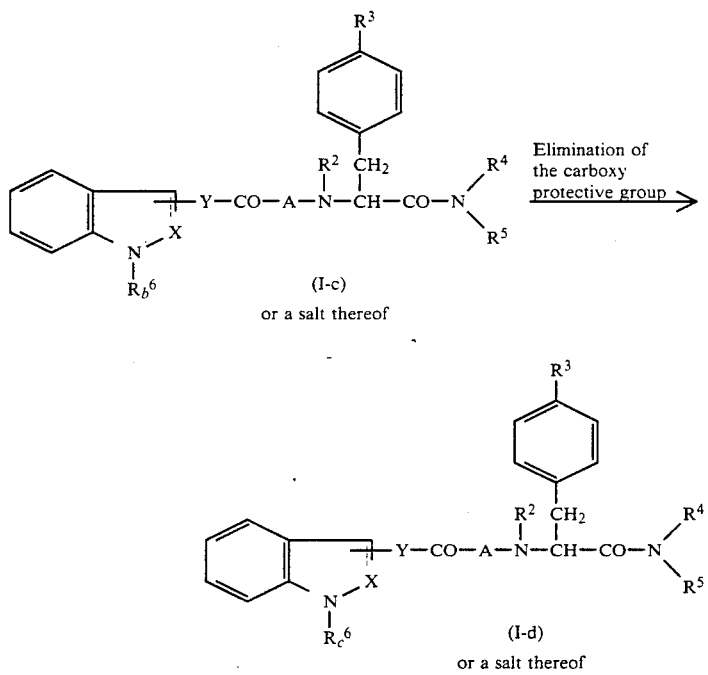
Process 4
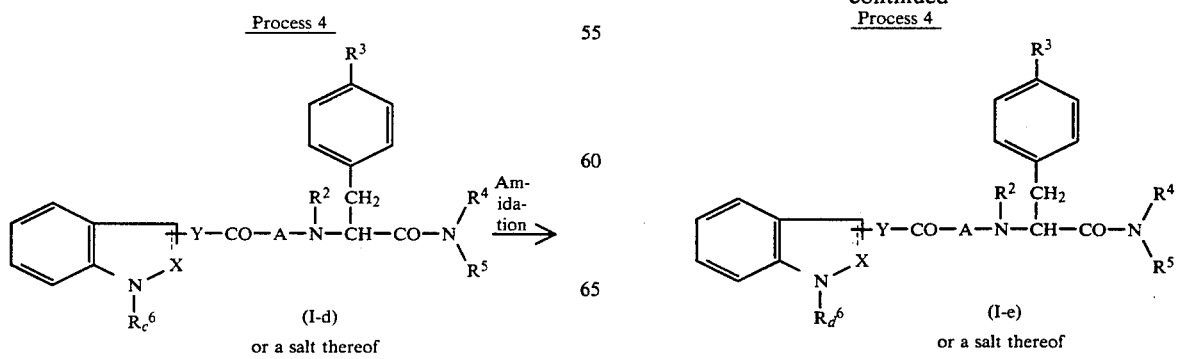

Process 5

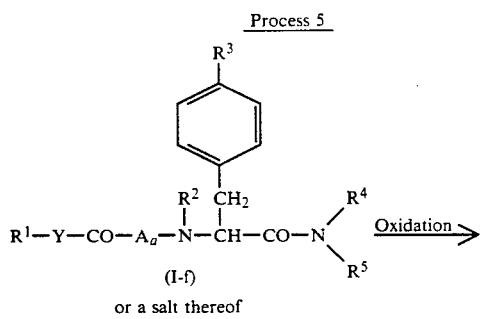
(I-f) or a salt thereof → Oxidation →

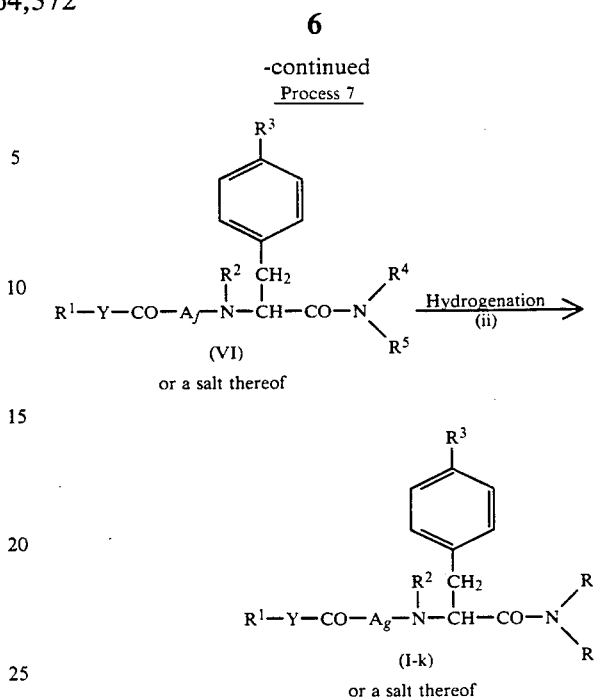

(I-g) or a salt thereof

Process 6

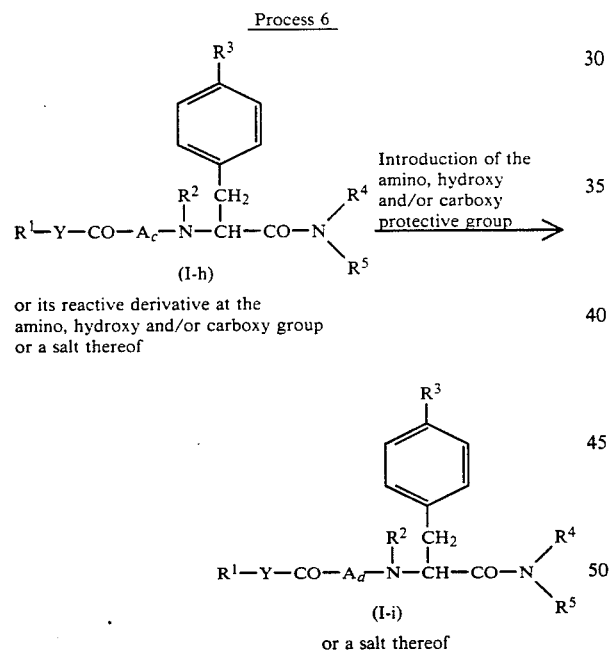
(I-h) or its reactive derivative at the amino, hydroxy and/or carboxy group or a salt thereof → Introduction of the amino, hydroxy and/or carboxy protective group →

(I-i) or a salt thereof

Process 7

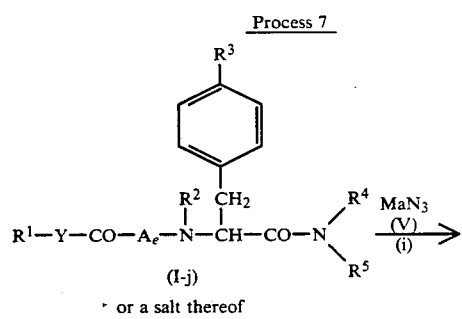
(I-j) or a salt thereof → MaN₃ (V) (i) →

-continued
Process 7

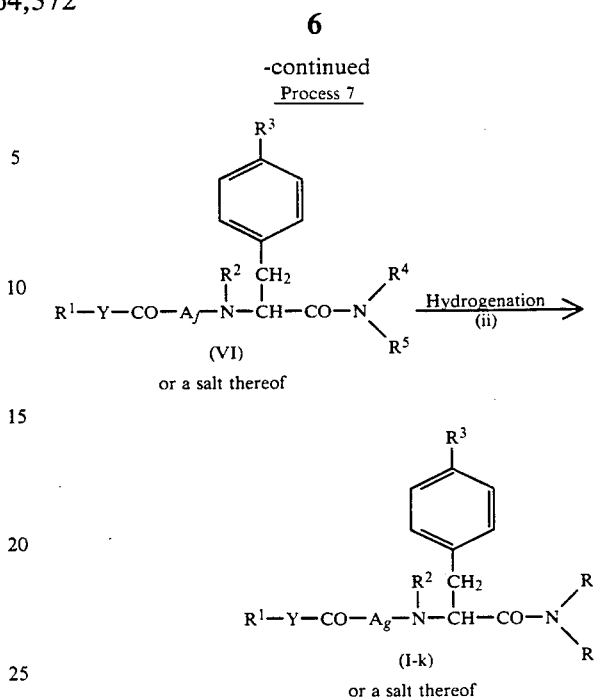
(VI) or a salt thereof → Hydrogenation (ii) →

(I-k) or a salt thereof

Process 8

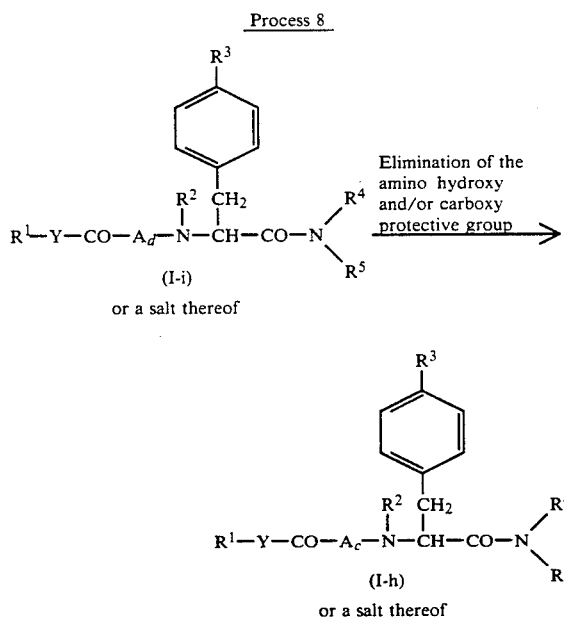
(I-i) or a salt thereof → Elimination of the amino hydroxy and/or carboxy protective group →

(I-h) or a salt thereof

Process 9

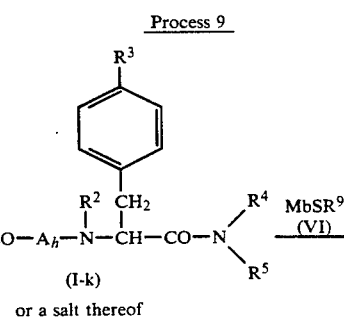
(I-k) or a salt thereof → MbSR⁹ (VI) →

-continued
Process 9

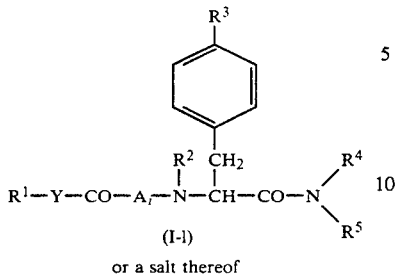

(I-l)
or a salt thereof

-continued
Process 11

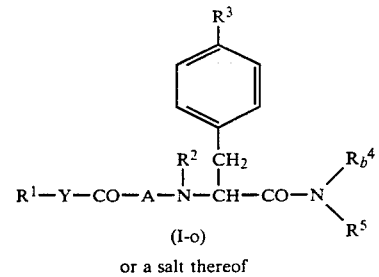

(I-o)
or a salt thereof

Process 10

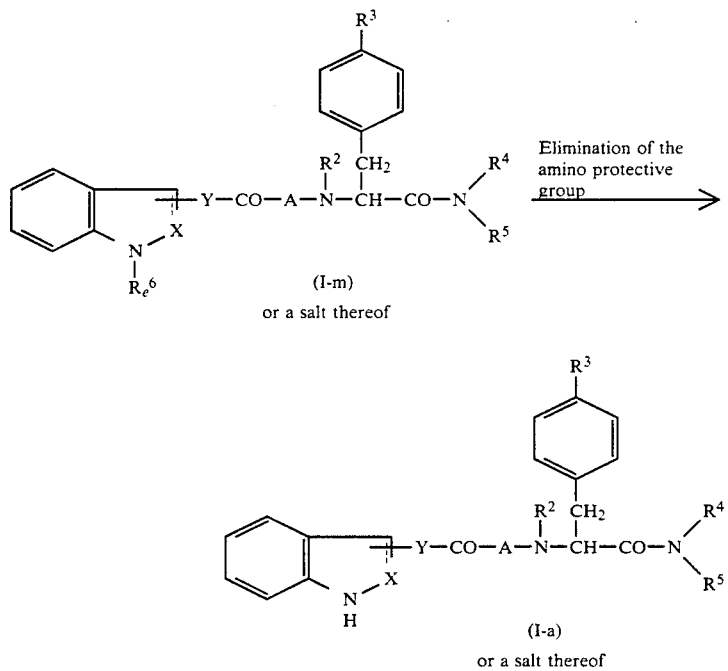

Elimination of the amino protective group

Process 11

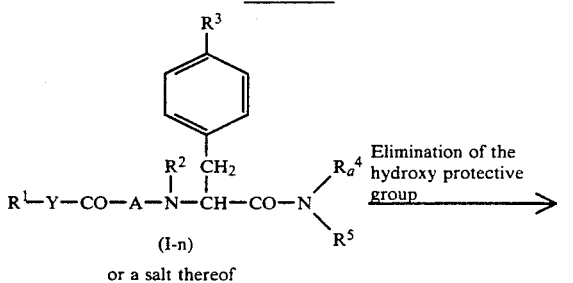

(I-n)
or a salt thereof

Elimination of the hydroxy protective group wherein
$R^1$, $R^2$, $R^3$, $R^4$, $R^5$, A, X and Y are each as defined above,
$R_a^4$ is protected hydroxy(lower)alkyl,
$R_b^4$ is hydroxy(lower)alkyl,
$R_a^6$ is lower alkyl which may have suitable substituent(s),
$R_b^6$ is protected carboxy(lower)alkyl,
$R_c^6$ is carboxy(lower)alkyl,
$R_d^6$ is carbamoyl(lower)alkyl which may have suitable substituent(s),
$R_e^6$ is amino protective group,
$R^9$ is lower alkyl,
$A_a$ is an amino acid residue containing a thio,
$A_b$ is an amino acid residue containing a sulfinyl or sulfonyl,
$A_c$ is an amino acid residue containing an amino, a hydroxy and/or a carboxy,
$A_d$ is an amino acid residue containing a protected amino, a protected hydroxy and/or a protected carboxy,
$A_e$ is an amino acid residue containing a sulfonyloxy which has a suitable substituent,
$A_f$ is an amino acid residue containing an azido, $A_g$ is an amino acid residue containing an amino,
$A_h$ is an amino acid residue containing a protected hydroxy,
$A_i$ is an amino acid residue containing lower alkylthio,
L is an acid residue, and
$M_a$ and $M_b$ are each an alkaline metal.

As to the starting compounds (II) and (III), some of them are novel and can be prepared by the procedures described in the preparations and Examples mentioned later or a conventional manner.

Throughout the present specification, the amino acid, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues.

Suitable pharmaceutically acceptable salts of the starting and object compound are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkyl" may include a straight or branched one such as methyl, ethyl, propyl, isopropyl, butyl, isobutyl, tert-butyl, pentyl, hexyl, and the like, in which the most preferred one is methyl.

Suitable "aryl" and the aryl moiety of "arylamino" may include phenyl, tolyl, xylyl, mesityl, cumenyl, naphtyl, and the like, in which the preferred one is $C_6$-$C_{10}$ aryl and the most preferred one is phenyl.

Suitable "lower alkylene" is one having 1 to 6 carbon atom(s) and may include methylene, ethylene, trimethylene, propylene, tetramethylene, methyltrimethylene, hexamethylene, and the like, in which the preferred one is methylene, ethylene or trimethylene.

Suitable "lower alkenylene" is one having 2 to 6 carbon atom(s) and may include vinylene, propenylene, and the like, in which the preferred one is vinylene.

Suitable "an amino acid residue excepting D-Trp" means a bivalent residue derived from an amino acid excepting D-Trp, and such amino acid may be glycine (Gly), D- or L- alanine (Ala), β-alanine (βAla), D- or L-valine (Val), D- or L- leucine (Leu), D- or L-isoleucine (Ile), D- or L- serine (Ser), D- or L- threonine (Thr), D- or L-cysteine (Cys), D- or L- methionine (Met), D- or L-phenylalanine (Phe), L-tryptophan (Trp), D- or L- tyrosine (Tyr), D- or L- proline (Pro), D- or L- hydroxypropine (Pro(OH)) such as 3-hydroxyproline (Pro[3OH)) and 4-hydroxyproline (Pro(4OH)), D- or L- azetidine-2-carboxylic acid (Azt), D- or L- thioproline (Tpr), D- or L-aminoproline (Pro(NH₂)) such as 3-aminoproline (Pro(3NH₂)) and 4-aminoproline (Pro(4NH₂)), D- or L- pyroglutamic acid (pGlu), D- or L- 2-aminoisobutyric acid (Aib), D- or L-glutamic acid (Glu), D- or L- aspartic acid (Asp), D- or L- glutamine (Gln), D- or L- asparagine (Asn), D- or L-lysine (Lys), D- or L- arginine (Arg), D- or L- histidine (His), D- or L- ornithine (Orn), D- or L- hydroxypiperidinecarboxylic acid such as 5-hydroxypiperidine-2-carboxylic acid, D- or L- mercaptoproline (Pro(SH)) such as 3-mercaptoproline (Pro(3SH)) and 4-mercaptoproline (Pro(4SH)), whose side chains, which are amino, hydroxy, thiol or carboxy groups, may be substituted by the suitable substituent(s). Said suitable substituent(s) may include acyl such as carbamoyl, lower alkanoyl (e.g., formyl, acetyl, etc.), trihalo(lower)alkoxycarbonyl (e.g. 2,2,2-trichloroethoxycarbonyl, etc.), ar(lower)alkoxycarbonyl (e.g. benzyloxycarbonyl, etc.), lower alkylsulfonyl (e.g., mesyl ethylsulfonyl, etc.), lower alkoxalyl (e.g., methoxyalyl, ethoxyalyl, etc.), arylsulfonyl (e.g., phenylsulfonyl, tolylsulfonyl, etc.), haloar(lower)alkoxycarbonyl (e.g., o-chlorobenzyloxycarbonyl, etc.), carboxy(lower)alkanoyl (e.g., carboxyacetyl, carboxypropionyl, etc.), glycyl, β-alanyl, N-lower alkoxycarbonylglycyl (e.g., N-t-butoxycarbonylglycyl, etc.) and N-lower alkoxycarbonyl-β-alanyl (e.g., N-t-butoxycarbonyl-β-alanyl, etc.), N,N-di(lower)alkylamino(lower)alkanoyl (e.g., N,N-dimethylaminoacetyl, N,N-diethylaminoacetyl, N,N-dimethylaminopropionyl, N,N-diethylaminopropionyl, etc.), carboxyalyl, morpholinocarbonyl, amino(lower)alkanoyl (e.g., aminoacetyl, aminopropionyl, etc.), N-ar(lower)alkoxycarbonylamino(lower)alkanoyl (e.g., N-benzyloxycarbonylaminoacetyl, etc.), threonyl, N-lower alkoxycarbonylthreonyl (e.g. N-t-butoxycarbonylthreonyl, etc.), N-lower alkanoylthreonyl (e.g., N-acetylthreonyl, etc.), N-lower alkoxycarbonyl(lower)alkyl-N-lower alkoxycarbonylamino(lower)alkanoyl (e.g., N-t-butoxycarbonylmethyl-N-t-butoxycarbonylaminoacetyl, etc.), α-glutamyl, N-ar(lower)alkoxycarbonyl-O-ar(lower)alkyl-α-glutamyl (e.g., N-benzyloxycarbonyl-O-benzyl-α-glutamyl, etc.), γ-glutamyl, N-ar(lower)alkoxycarbonyl-O-ar(lower)alkyl-γ-glutamyl (e.g., N-benzyloxycarbonyl-O-benzyl-γ-glutamyl, etc.), lower alkyl (e.g., methyl, ethyl, t-butyl, etc.), carboxy(lower)alkyl (e.g. carboxymethyl, etc.), morpholino, glycino amide, threonino amide, N'-glutamino N-lower alkylamide (e.g., N'-glutamino N-t-butylamide, etc.), di(lower)alkylamino (e.g. dimethylamino, etc.), ar(lower)alkyl (e.g., benzyl, phenethyl, etc.), trihalo(lower)alkyl (e.g., 2,2,2-trichloroethyl, etc.), lower alkoxycarbonyl(lower)alkyl (e.g., methoxycarbonylmethyl, ethoxycarbonylmethyl, t-butoxycarbonylmethyl, etc.), or usual protecting group used in the field of art. In case that such amino acid contain a thio, it may be its sulfoxide or sulfone.

Suitable "carboxy(lower)alkyl" may include carboxymethyl, carboxyethyl, carboxypropyl, and the like.

Suitable "protected carboxy(lower)alkyl" means the above-mentioned carboxy(lower)alkyl, in which the carboxy group is protected by a conventional protective group such as esterified carboxy group. Preferred example of the ester moiety thereof may include lower alkyl ester (e.g. methyl ester, ethyl ester, propyl ester, tert-butyl ester, etc.), and the like.

Suitable "carbamoyl(lower)alkyl which may have suitable substituent(s)" may include carbamoyl(lower)alkyl (e.g., carbamoylmethyl, carbamoylethyl, carbamoylpropyl, etc.), carbamoyl(lower)alkyl having suitable substituent(s) such as lower alkylcarbamoyl(lower)alkyl (e.g., methylcarbamoylmethyl, ethylcarbamoylmethyl, etc.), amino(lower)alkylcarbamoyl(lower)alkyl (e.g., aminomethylcarbamoylmethyl, aminoethylcarbamoylmethyl, etc.), lower alkylamino(lower)alkylcarbamoyl(lower)alkyl (e.g., dimethylaminomethylcarbamoylmethyl, dimethylaminoethylcarbamoylmethyl, etc.), and the like.

Suitable "lower alkyl which may have suitable substituent(s)" may include a conventional group, which is used in the field of art such as lower alkyl, carboxy(lower)alkyl, protected carboxy(lower)alkyl, carbamoyl(lower)alkyl which may have suitable substituent(s), each of which is as exemplified above, lower alkylamino(lower)alkyl (e.g. dimethylaminomethyl, dimethylaminoethyl, etc.), hydroxy(lower)alkyl (e.g., hydroxymethyl, hydroxyethyl, etc.), protected hydroxy(lower)alkyl such as acyloxy(lower)alkyl (e.g. acetyloxyethyl, etc.) and the like.

Suitable "an amino acid residue containing a thio" means a bivalent residue derived from an amino acid containing a thio, and may include Tpr, Met, and the like.

Suitable "an amino acid residue containing a sulfinyl or sulfonyl" means a bivalent residue derived from an amino acid containing a sulfinyl or sulfonyl, and may include Tpr(O), Met(O), Tpr(O$^2$), Met(O$^2$), and the like.

Suitable "an amino acid residue containing an amino, a hydroxy and/or a carboxy" may include a bivalent residue of an amino acid such as Pro(4OH), Ser, Thr, Tyr, and the like.

Suitable "an amino acid residue containing a protected amino, a protected hydroxy and/or a protected carboxy" means the above-mentioned group, in which the amino, hydroxy and/or carboxy is protected by a conventional group used in the field of the art such as carbamoyl, lower alkylsulfonyl (e.g., mesyl, ethylsulfonyl, etc.), arylsulfonyl (e.g., phenylsulfonyl, tolylsulfonyl, etc.), lower alkoxycarbonyl(lower)alkyl (e.g., methoxycarbonylmethyl, ethoxycarbonylmethyl, etc.), and the like.

Suitable "an amino acid residue containing sulfonyloxy which has a suitable substituent" means a bivalent residue derived from an amino acid containing sulfonyloxy which has a suitable substituent, in which "sulfonyloxy which has a suitable substituent" may include lower alkylsulfonyloxy (e.g., methylsulfonyloxy, ethylsulfonyloxy, etc.), halo(lower)alkylsulfonyloxy (e.g., trifluoromethylsulfonyloxy, etc.), arylsulfonyloxy (e.g., phenylsulfonyloxy, tolylsulfonyloxy, etc.), and the like.

Suitable "an amino acid residue containing an azido" may include a bivalent residue of an amino acid such as Pro(4N$_3$), and the like.

Suitable "an amino acid residue containing an amino" may include a bivalent residue of an amino acid such as Pro(4NH$_2$), and the like.

Suitable "alkaline metal" may include sodium, potassium, and the like.

Suitable "an acid residue" may include halogen (e.g., fluoro, chloro, bromo, iodo), acyloxy (e.g., tosyloxy, mesyloxy, etc.), and the like.

Suitable "ar(lower)alkyl which may have suitable substituent(s)" may include a conventional group, which is used in the field of amino acid and peptide chemistry, such as ar(lower)alkyl (e.g. trityl, benzhydryl, benzyl, phenethyl, etc.), substituted ar(lower)alkyl (e.g., o-fluorobenzyl, m-fluorobenzyl, o-trifluoromethylbenzyl, etc.), and the like.

Suitable "pyridyl(lower)alkyl" may include 2-pyridylmethyl, 3-pyridylmethyl, 4-pyridylmethyl, and the like.

Suitable group of the formula:

in which R$^4$ and R$^5$ are linked together to form benzene-condensed lower alkylene, may include 1-indolinyl, 2-isoindolinyl, 1,2,3,4-tetrahydroquinolin-1-yl, 1,2,3,4-tetrahydroisoquinolin-2-yl, and the like.

Suitable "hydroxy(lower)alkyl" may include hydroxymethyl, hydroxyethyl, hydroxypropyl, and the like.

Suitable "protected hydroxy(lower)alkyl" means the above-mentioned hydroxy(lower)alkyl, in which the hydroxy group is protected by a conventional protective group such as acyl (e.g. acetyl, etc.), and may include acetyloxyethyl and the like.

Suitable "amino protective group" may be a conventional protective group, which is used in the field of amino acid and peptide chemistry, that is, may include acyl such as lower alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, etc.), and the like.

Suitable "an amino acid residue containing lower alkylthio" means a bivalent residue of an amino acid containing lower alkylthio, in which lower alkylthio may include methylthio, ethylthio, and the like.

Suitable substituent on R$^1$ moiety may include a conventional group, which is used in the field of amino acid and peptide chemistry, such as lower alkyl which may have suitable substituent(s), amino protective group, each as defined above, hydroxy, halogen (e.g. fluoro, chloro, etc.), lower alkoxy (e.g. methoxy, butoxy, etc.), N,N-di(lower)alkylamino (e.g. dimethylamino, etc.), lower alkoxycarbonyl (e.g. methoxycarbonyl, t-butoxycarbonyl, etc.), and the like.

Particularly, the preferred embodiments of R$^1$, R$^2$, R$^3$, R$^4$, R$^5$, A and Y are as follows.

R$^1$ is
lower alkyl (e.g. isopentyl, etc.);
aryl which may have one or more, preferably one to three substituent(s) selected from hydroxy, lower alkoxy and N,N-di(lower)alkylamino (e.g. phenyl, hydroxyphenyl, dihydroxyphenyl, hydroxydimethoxyphenyl, N,N-dimethylaminophenyl, etc.);
arylamino (e.g. anilino, etc.);
pyridyl;
pyrrolyl;
pyrazolopyridyl;
quinolyl;
benzofuryl;
indazolyl;
benzothienyl;

a group of the formula:

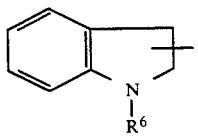

wherein
R⁶ is
hydrogen; or
lower alkoxycarbonyl (e.g. t-butoxycarbonyl, etc.);
or a group of the formula:

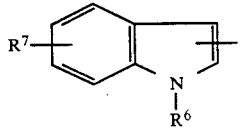

wherein
R⁶ is
hydrogen; lower alkyl (e.g. methyl, isopropyl, etc.);
carboxy(lower)alkyl (e.g. carboxymethyl etc.);
esterified carboxy(lower)alkyl such as lower alkoxycarbonyl(lower)alkyl (e.g. t-butoxycarbonylmethyl, etc.);
N,N-di(lower)alkylamino(lower)alkyl (e.g. N,N-dimethylaminoethyl, etc.); or
N,N-di(lower)alkylamino(lower)alkylcarbamoyl(lower)alkyl (e.g. N,N-dimethylaminoethylcarbamoylmethyl, etc.); and
R⁷ is
hydrogen;
hydroxy;
halogen (e.g. chloro, etc.);
lower alkyl (e.g. methyl, etc.);
lower alkoxy (e.g. methoxy, etc.); or
N,N-di(lower)alkylamino (e.g. N,N-dimethylamino, etc.);
R² is
hydrogen; or
lower alkyl (e.g. methyl, etc.);
R³ is
hydrogen; or
hydroxy;
R⁴ is
lower alkyl (e.g. methyl, etc.);
hydroxy(lower)alkyl (e.g. hydroxyethyl, etc.); or
acyloxy(lower)alkyl such as lower alkanoyloxy(lower)alkyl (e.g. acetyloxyethyl, etc.);
R⁵ is
ar(lower)alkyl such as mono or di or triphenyl(lower)alkyl (e.g. benzyl, etc.);
haloar(lower)alkyl such as halo-substituted mono or di or triphenyl(lower)alkyl (e.g. fluorobenzyl, chlorobenzyl, etc.);
halo(lower)alkylar(lower)alkyl such as halo(lower)alkyl-substituted mono or di or triphenyl(lower)alkyl (e.g. trifluoromethylbenzyl, etc.); or
pyridyl(lower)alkyl (e.g. pyridylmethyl, etc.); or
R⁴ and R⁵ are
linked together to form benzene-condensed lower alkylene (e.g. 1,2,3,4-tetrahydroquinolin-2-yl, etc.);
A is
a bivalent residue derived from an amino acid excepting D-Trp, which may have suitable substituent(s) such as proline, hydroxyproline (e.g. 4-hydroxyproline, etc.), glycine, serine, asparagine, aminoisobutyric acid (e.g. 2-aminoisobutyric acid, etc.), azetidinecarboxylic acid (e.g. azetidine-2-carboxylic acid, etc.), thioproline, aspartic acid, lysine, methionine, threonine, alanine, ornithine, hydroxypiperidinecarboxylic acid e.g. 5-hydroxypiperidine-2-carboxylic acid, etc.), 4-acyloxyproline (e.g. 4-lower alkanoyloxyproline, 4-lower alkanesulfonyloxyproline, 4-arenesulfonyloxyproline, 4-carbamoyloxyproline, etc.], 4-lower alkoxyproline, 4-carboxy(lower)alkoxyproline, 4-lower alkoxycarbonyl-lower alkoxyproline, 4-lower alkylthioproline, 4-aminoproline, 4-acylaminoproline [e.g. 4-carboxy(lower)alkanoylaminoproline, 4-amino(lower)alkanoylaminoproline, 4-ar(lower)alkoxycarbonylamino(lower)alkanoylaminoproline, 4-amino and carboxy substituted lower alkanoylaminoproline, 4-ar(lower)alkoxycarbonylamino and ar(lower)alkoxycarbonyl substituted lower alkanoylaminoproline, etc.), 4-oxaloaminoproline, 4-lower alkoxalylaminoproline, 4-lower alkanesulfonylaminoproline, 4-N,N-di(lower)alkylamino(lower)alkanoylaminoproline, etc.], O³-lower alkylserine, O³-ar(lower)alkylserine, thioproline sulfoxide, thioproline sulfone, O⁴-ar(lower)alkyl hydrogen aspartate, (carbamoyl and hydroxy substituted lower alkylamino)-β-aspartate, carbamoyl(lower)alkylamino-β-aspartate, morpholino-β-aspartate, (carbamoyl and lower alkylcarbamoyl substituted lower alkylamino)-β-aspartate, N⁶-acyllysine [e.g. N⁶-ar(lower)alkoxycarbonyllysine, N⁶-haloar(lower)alkoxycarbonyllysine, N⁶-N,N-di(lower)alkylamino-lower alkanoyllysine, N⁶-morpholinocarbonyllysine, N⁶-N-lower alkoxycarbonyl-N-lower alkoxycarbonyl(lower)alkylamino(lower)alkanoyllysine, N⁶-(hydroxy and lower alkanoylamino substituted lower alkanoyl)lysine, N⁶-(hydroxy and lower alkoxycarbonylamino substituted lower alkanoyl)lysine, N⁶-lower alkoxycarbonylamino(lower)alkanoyllysine, N⁶-amino(lower)alkanoyllysine, etc.], N⁵-acylornithine [e.g. N⁵-ar(lower)alkoxycarbonylornithine, N⁵-(hydroxy and lower alkanoylamino substituted lower alkanoyl)ornithine, N⁵-(hydroxy and lower alkoxycarbonylamino substituted lower alkanoyl)ornithine, etc.], etc.;
more preferably Pro, D—Pro, Pro(4OH), Gly, Ser, Asn, Aib, Azt, Tpr, Asp, Lys, Met, Thr, Ala, Orn, Tpr(O), Tpr(O₂), Pro(4OCH₂CO₂Buᵗ), Pro(4OMs), Pro(4NH₂), 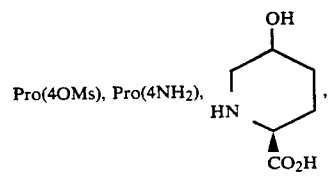

Pro(4NHCOCO₂Et), Pro(4OCONH₂), Asp(OBzl),

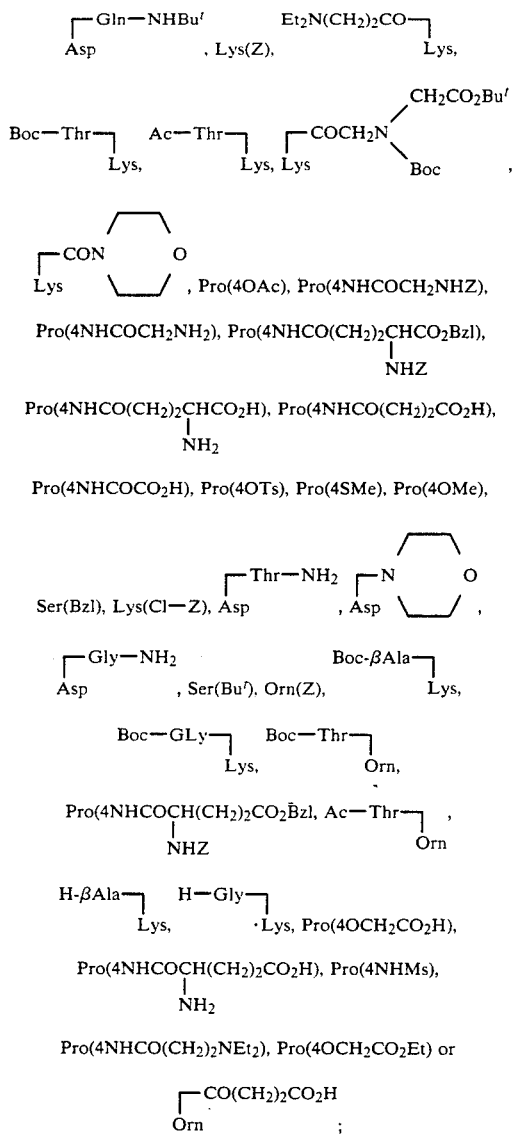

and

Y is
bond;
lower alkylene (e.g. methylene, ethylene, trimethylene, etc.); or
lower alkenylene (e.g. vinylene, etc.).

The processes for preparing the object compound (I) are explained in detail in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl) acetamide, bis(trimethylsilyl)urea or the like; a derivative formed by reaction of the compound (II) with phosphorus trichloride or phosgene, and the like.

Suitable salts of the compound (II) and its reactive derivative can be referred to the ones as exemplified for the compound (I).

Suitable reactive derivative at the carboxy group of the compound (III) may include an acid halide, an acid anhydride, an activated amide, an activated ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. metaanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl

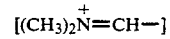

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of the compound (III) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N- cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; benzotriazol-1-yl-oxy-tris(dimethylamino)-phosphoniumhexafluorophosphate; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound (I-b) or a salt thereof can be prepared by reacting the compound (I-a) or a salt thereof with the compound (IV).

The present reaction is usually carried out in the presence of a base such as alkali lithium (e.g. n-butyl lithium, etc.), alkali metal hydride (e.g. sodium hydride, potassium hydride, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

If necessary, the present reaction can be used phase transfer catalyst (e.g. cetyltrimethylammonium chloride, etc.).

The reaction temperature is not critical and the reaction is usually carried out under cooling, at ambient temperature or under heating.

The present reaction includes, within its scope, the case that the hydroxy group on A is reacted during the reaction or at the post-treating step of the present process.

Process 3

The object compound (I-d) or a salt thereof can be prepared by subjecting the compound (I-c) or a salt thereof to elimination reaction of the carboxy protective group.

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid.

The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-one, 1,4-diazabicyclo[2.2.2]octane, 1,5-diazabicyclo[5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water, or a mixed solvent thereof.

The reaction temperature is not critical, and it may suitably be selected in accordance with the kind of the carboxyprotective group and the elimination method.

The elimination using Lewis acid is carried out by reacting the compound (I-c) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reduction elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like.

The reduction method applicable for the elimination reacting may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

The present elimination reaction includes, within its scope, the case that the amino, hydroxy and/or carboxy protective group for A is eliminated during the reaction or at the post-treating step of the present process.

Process 4

The object compound (I-e) or a salt thereof can be prepared by subjecting the compound (I-d) or its reactive derivative at the carboxy group or a salt thereof to amidation.

The amidating agent to be used in the present amidation may include amine which may have suitable substituent(s) such as lower alkyl (e.g., methyl, ethyl, etc.), amino(lower)alkyl (e.g., aminomethyl, aminoethyl, etc.), lower alkylamino(lower)alkyl (e.g., dimethylaminomethyl, dimethylaminoethyl, etc.) and the like.

Suitable reactive derivative at the carboxy group of the compound (I-d) can be referred to the ones as exemplified for the compound (III) in Process 1.

This reaction can be carried out in substantially the same manner as Process 1, and therefore the reaction mode and reaction conditions (e.g. reaction derivatives, solvents, reaction temperature, etc.] of this reaction are to be referred to those as explained in Process 1.

Process 5

The object compound (I-g) or a salt thereof can be prepared by oxidizing the compound (I-f) or a salt thereof.

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt, thereof, etc.), ozone, hydrogen peroxide, urea-hydrogen peroxide, N-halosuccinimide (e.g. N-bromosuccinimide, N-chlorosuccinimide, etc.), hydrochlorite compound (e.g. tert-butyl hydrochlorite, etc.) permanganate (e.g. potassium permanganate, etc.), or any other conventional oxidizing agent which can oxidide a sulfinyl group to a sulfonyl group.

The present reaction can also be carried out in the presence of a compound comprising Group Vb or VIb metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol or a mixture thereof.

The reaction temperature is not critical and the reaction is preferably carried out under cooling to at ambient temperature.

Process 6

The object compound (I-i) or a salt thereof can be prepared by subjecting the compound (I-h) or its reactive derivative at the amino, hydroxy and/or carboxy group or a salt thereof to introduction reaction of the amino, hydroxy and/or carboxy protective group.

The reaction can be carried out in substantially the same manner as Process 1, and therefore the reaction mode and reaction conditions [e.g. solvents, reaction temperature, etc.] of this reaction are to be referred to those as explained in Process 1.

The present reaction includes, within its scope, the case that the amino group on $R^1$ is reacted during the reaction or at the post-treating step of the present process.

Process 7-(i)

The compound (VI) or a salt thereof can be prepared by reacting the compound (I-j) or a salt thereof with the compound (V).

The reaction is usually carried out in a conventional solvent such as dimethyl sulfoxide or any other solvent which does not adversely influence the reaction.

The reaction temperature is not critical and the reaction is usually carried out under warming to heating.

Process 7-(ii)

The object compound (I-k) or a salt thereof can be prepared by subjecting the compound (VI) or a salt thereof to hydrogenation. This reaction is usually carried out in the presence of triphenylphosphine, palladium on carbon, or the like.

The reaction is usually carried out in a conventional solvent such as alcohol (e.g., methanol, ethanol, etc.), or any other solvent which does not adversely influence the reaction.

The reaction temperature is not critical and the reaction is usually carried out under cooling to heating.

Process 8

The object compound (I-h) or a salt thereof can be prepared by subjecting the compound (I-i) or a salt thereof to elimination reaction of the amino, hydroxy and/or carboxy protective group.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

The present elimination reaction includes, within its scope, the case that the carboxy protective group for $R^1$ is eliminated during the reaction or at the post-treating step of the present process.

Process 9

The object compound (I-l) or a salt thereof can be prepared by reacting the compound (I-k) or a salt thereof with the compound (VI).

The reaction is usually carried out in a conventional solvent such as N,N-dimethylformamide or any other solvent which does not adversely influence the reaction.

The reaction temperature is not critical and the reaction is usually carried out under cooling to heating.

Process 10

The object compound (I-a) or a salt thereof can be prepared by subjecting the compound (I-m) or a salt thereof to elimination reaction of the amino, protective group.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

Process 11

The object compound (I-o) or a salt thereof can be prepared by subjecting the compound (I-n) or a salt thereof to elimination reaction of the hydroxy protective group.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

The compounds obtained by the above processes can be isolated and purified by a conventional method such as pulverization, recrystallization, column chromatography, reprecipitation, or the like.

It is to be noted that the compound (I) and the other compounds may include one or more stereoisomers due to asymmetric carbon atoms, and all of such isomers and mixture thereof are included within the scope of this invention.

The object compounds (I) and pharmaceutically acceptable salt thereof have pharmacological activities such as tachykinin antagonism, especially substance P antagonism, neurokinin A antagonism or neurokinin B antagonism, and therefore are useful for treating or preventing tachykinin mediated diseases, for example, respiratory diseases such as asthma, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, and the like; pains or aches (e.g. migraine, headache, toothache, cancerous pain, etc.); and the like.

Further, it is expected that the object compounds (I) of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, and the like; pollakiuria; dementia; schizophrenia; Huntington's chorea; carcinoid syndrome; immunosuppresive agent; and the like.

For therapeutic purpose, the compounds (I) and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparation, auxiliary substances, stabilizing agents, wetting or emulsifying agents, buffers and other commonly used additives.

While the dosage of the compounds (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating asthma and the like. In general, amounts between 0.1 mg/body and about 1,000 mg/body may be administered per day.

In order to illustrate the usefulness of the object compound (I), the pharmacological test data of some representative compounds of the compound (I) are shown in the following.

Test Compounds:

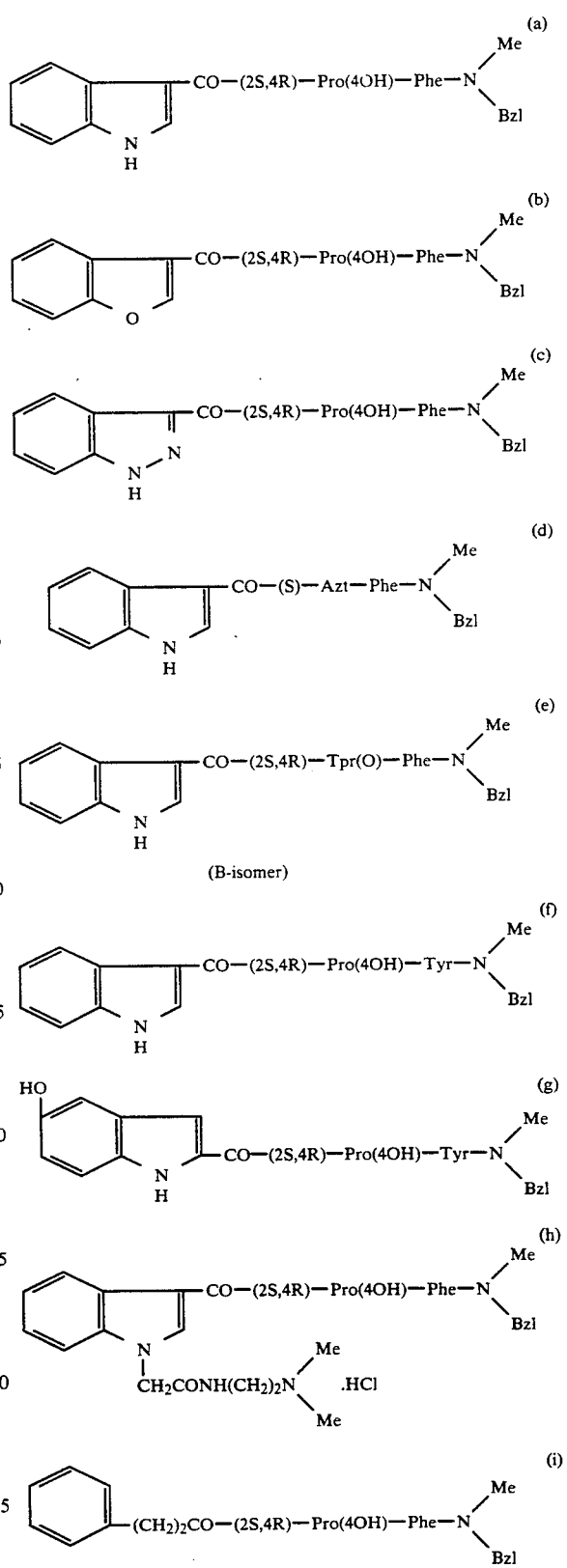

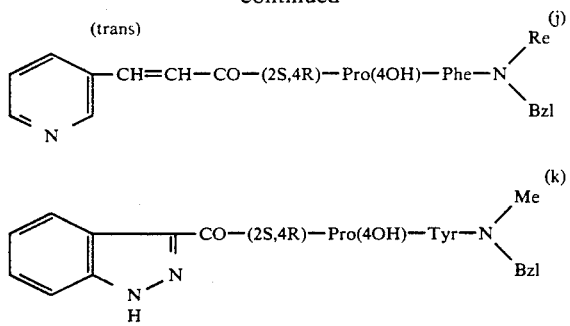

(1) ³H-Substance P receptor binding

Test Method:

(a) Crude lung membrane preparation

Male Hartly strain guinea pigs were sacrificed by decapitation. The trachea and lung were removed and homogenized in buffer (0.25M sucrose, 50 mM Tris-HCl pH 7.5, 0.1 mM EDTA) by using Polytoron (Kinematica). The homogenate was centrifuged (1000 xg, 10 min) to remove tissue clumps and the supernatant was centrifuges (14000 xg 20 min) to yield pellets. The pellets were resuspended in buffer (5 mM Tris-HCl pH 7.5), homogenized with a teflon homogenizer and centrifuged (14,000 xg, 20 min) to yield pellets which were referred to as crude membrane fractions. The obtained pallets were stored at −70° C. until use.

(b) ³H-Substance P binding to preparation membrane

Frozen crude membrane fractions were thawed and resuspended in Medium 1 (50 mM Tris-HCl pH 7.5, 5 mM MnCl₂, 0.02% BSA, 2 µg/ml chymostatin, 4 µg/ml leupeptin, 40 µg/ml bacitracin.) ³H-substance P (1 nM) was incubated with 100 µl of the membrane preparation in Medium 1 at 4° C. for 30 minutes in a final volume of 500 µl. At the end of the incubation period, reaction mixture was quickly filtered over a Whatman GF/B glass filter (pretreated with 0.1% polyethylene imine for 3 hours prior to use) under aspiration. The filters were then washed four times with 5 ml of the buffer (50 mM Tris-HCl, pH 7.5). The radioactivity was counted in 5 ml of Aquazol-2 in Packerd scintillation counter (Packerd TRI -CARB 4530).

Test Results:

| Test Compounds (0.1 µl/ml) | Inhibition (%) |
|---|---|
| (a) | 96 |
| (b) | 99 |
| (c) | 99 |
| (d) | 93 |
| (e) | 100 |
| (f) | 100 |
| (g) | 98 |
| (h) | 100 |
| (i) | 98 |
| (j) | 94 |
| (k) | 100 |

(2) Effect of intratrachea administration on substance P induced bronchoconstriction in guinea-pigs Test Method:

Male Hartley strain guinea-pigs weighing 300–500 g were immobilized with sodium pentobarbital (10 mg/animal administered intraperitoneally). A catheter was also intubated into trachea for artifical ventilation. The animal was respirated by means of a miniature respiration Harvard B-34, 5 ml/stroke, 60 strokes/minutes). Test Compound was suspended in 0.1% methyl cellulose-saline) and administered intratrachea.

Test Results:

| Test Compounds | ED₅₀ (mg/kg) |
|---|---|
| (a) | 0.072 |
| (k) | 0.08 |

The following examples are given for purpose of illustrating the present invention in detail.

In these examples, there are employed the following abbreviations in addition to the abbreviations adopted by the IUPAC-IUB.

| | |
|---|---|
| Ac | acetyl |
| Aib | 2-aminoisobutyric acid |
| Azt | azetidine-2-carboxylic acid |
| Boc | t-butoxycarbonyl |
| BSA | bistrimethylsilylacetamide |
| Buᵗ | t-butyl |
| Bz | benzoyl |
| Bzl | benzyl |
| Bzl(o-F) | o-fluorobenzyl |
| Bzl(m-F) | m-fluorobenzyl |
| Bzl(o-CF₃) | o-trifluoromethylbenzyl |
| DMAP | dimethylaminopyridine |
| DMF | dimethylformamide |
| DMSO | dimethylsulfoxide |
| Et | ethyl |
| HOBT | N-hydroxybenzotriazole |
| IPE | isopropyl ether |
| Me | methyl |
| Ms | mesyl |
| NMM | N-methylmorpholine |
| 4N—HCl/DOX | 4N-hydrogen chloride in 1,4-dioxane |
| Prⁱ | isopropyl |
| Py(2) | 2-pyridyl |
| Su | succinimido |
| TEA | triethylamine |
| TFA | trifluoroacetic acid |
| THF | tetrahydrofuran |
| Tpr | thioproline |
| Ts | tosyl |
| WSC | 1-ethyl-3-(3'-dimethylaminopropyl)-carbodiimide |
| Z | benzyloxycarbonyl |

The Starting Compounds used and the Object Compounds obtained in the following examples are given in The Table as below, in which the formulae of the Starting Compounds are in the upper and the formulae of the Object Compounds are in the lower, respectively.

TABLE

Formula

Preparation No.

1    Boc—Phe—OH

TABLE-continued

| | Formula |
|---|---|
| | Boc—Phe—N(Me)(Bzl) |
| 2 | Boc—Phe—N(Me)(Bzl) |
| | HCl.H—Phe—N(Me)(Bzl) |
| 3 | HCl.H—Phe—N(Me)(Bzl) |
| | Boc—(2S,4R)—Pro(4OH)—Phe—N(Me)(Bzl) |
| 4 | Boc—(2S,4R)—Pro(4OH)—Phe—N(Me)(Bzl) |
| | HCl.H—(2S,4R)—Pro(4OH)—Phe—N(Me)(Bzl) |
| 5-(1) | HCl.H—Phe—N(Me)(Bzl) |
| | Boc—Pro—Phe—N(Me)(Bzl) |
| 5-(2) | HCl.H—Phe—N(Me)(Bzl) |
| | Boc—D—Pro—Phe—N(Me)(Bzl) |
| 5-(3) | HCl.H—Phe—N(Me)(Bzl) |
| | Boc—Gly—Phe—N(Me)(Bzl) |
| 5-(4) | HCl.H—Phe—N(Me)(Bzl) |

| | Formula |
|---|---|
| | Boc—Ser—Phe—N(Me)(Bzl) |
| 5-(5) | HCl·H—Phe—N(Me)(Bzl) |
| | Boc—Asn—Phe—N(Me)(Bzl) |
| 5-(6) | HCl·H—Phe—N(Me)(Bzl) |
| | Boc—Aib—Phe—N(Me)(Bzl) |
| 6 | H—(2S,4S)—Pro(4OH)—OH |
| | Boc—(2S,4S)—Pro(4OH)—OH |
| 7 | H—(S)—Azt—OH |
| | Boc—(S)—Azt—OH |
| 8-(1) | HCl·H—Phe—N(Me)(Bzl) |
| | Boc—(2S,4S)—Pro(4OH)—Phe—N(Me)(Bzl) |
| 8-(2) | HCl·H—Phe—N(Me)(Bzl) |
| | Boc—(2S)—Azt—Phe—N(Me)(Bzl) |
| 8-(3) | HCl·H—Phe—N(Me)(Bzl) |
| | Boc—Tpr—Phe—N(Me)(Bzl) |
| 9 | Boc—Tyr—OH |
| | Boc—Tyr—N(Me)(Bzl) |
| 10 | Boc—Tyr—N(Me)(Bzl) |

TABLE-continued

Formula

Boc—(2S,4R)—Pro(4OH)—Tyr—N(Me)(Bzl)

11  Boc—(2S,4R)—Pro(4OH)—Phe—N(Me)(Bzl)

Boc—(2S,4R)—Pro(4OCONHCOCCl₃)—Phe—N(Me)(Bzl)

12  Boc—(2S,4R)—Pro(4OCONHCOCCl₃)—Phe—N(Me)(Bzl)

Boc—(2S,4R)—Pro(4OCONH₂)—Phe—N(Me)(Bzl)

13  Boc—(2S,4R)—Pro(4OCONH₂)—Phe—N(Me)(Bzl)

HCl.H—(2S,4R)—Pro(4OCONH₂)—Phe—N(Me)(Bzl)

14  Boc—(2S,4R)—Pro(4OH)—Phe—N(Me)(Bzl)

Boc—(2S,4R)—Pro(4OCH₂CO₂Et)—Phe—N(Me)(Bzl)

15  Boc—(2S,4R)—Pro(4OCH₂CO₂Et)—Phe—N(Me)(Bzl)

HCl.H—(2S,4R)—Pro(4OCH₂CO₂Et)—Phe—N(Me)(Bzl)

16  HCl.H—Phe—N(Me)(Bzl)

Boc—Asp(OBzl)—Phe—N(Me)(Bzl)

17  HCl.H—Phe—N(Me)(Bzl)

TABLE-continued

| | Formula |
|---|---|
| | Boc—Asp(OBzl)—Phe—N(Me)(Bzl) |
| 18 | Boc—Asp(OBzl)—Phe—N(Me)(Bzl) |
| | HCl.H—Asp(OBzl)—Phe—N(Me)(Bzl) |
| 19 | Boc—Tyr—OH |
| | Boc—Tyr—N(Me)(CH₂Py(2)) |
| 20 | Boc—Phe—N⟨tetrahydroisoquinoline⟩ |
| | Boc—Pro—Phe—N⟨tetrahydroisoquinoline⟩ |
| 21-(1) | Boc—(2S,4R)—Pro(4OH)—Phe—N(Me)(Bzl(o-F)) |
| | HCl.H—(2S,4R)—Pro(4OH)—Phe—N(Me)(Bzl(o-F)) |
| 21-(2) | Boc—(2S,4R)—Pro(4OH)—Phe—N(Me)(Bzl(o-CF₃)) |
| | HCl.H—(2S,4R)—Pro(4OH)—Phe—N(Me)(Bzl(o-CF₃)) |
| 21-(3) | Boc—(2S,4R)—Pro(4OH)—Phe—N(Me)(Bzl(m-F)) |
| | HCl.H—(2S,4R)—Pro(4OH)—Phe—N(Me)(Bzl(m-F)) |
| 21-(4) | Boc—Pro—Phe—N(Me)(Bzl) |
| | HCl.H—Pro—Phe—N(Me)(Bzl) |

TABLE-continued

| | Formula |
|---|---|
| 21-(5) | Boc—Phe—N(Me)(Bzl(o-F)) |
| | HCl·H—Phe—N(Me)(Bzl(o-F)) |
| 21-(6) | Boc—Phe—N(Me)(Bzl(o-CF$_3$)) |
| | HCl·H—Phe—N(Me)(Bzl(o-CF$_3$)) |
| 21-(7) | Boc—Phe—N(Me)(Bzl(m-F)) |
| | HCl·H—Phe—N(Me)(Bzl(m-F)) |
| 21-(8) | Boc—Ser—Phe—N(Me)(Bzl) |
| | HCl·H—Ser—Phe—N(Me)(Bzl) |
| 21-(9) | Boc—(2S,4R)—Pro(4OH)—Tyr—N(Me)(CH$_2$Py(2)) |
| | 2HCl·H—(2S,4R)—Pro(4OH)—Tyr—N(Me)(CH$_2$Py(2)) |
| 21-(10) | Boc—(2S,4R)—Pro(4OH)—Phe—N(Me)(CH$_2$Py(2)) |
| | 2HCl·H—(2S,4R)—Pro(4OH)—Phe—N(Me)(CH$_2$Py(2)) |
| 21-(11) | Boc—(2S,4R)—Pro(4OH)—Phe—N((CH$_2$)$_2$OAC)(Bzl) |
| | HCl·H—(2S,4R)—Pro(4OH)—Phe—N((CH$_2$)$_2$OAC)(Bzl) |

TABLE-continued

| | Formula |
|---|---|
| 22-(1) | HCl.H—Phe—N(Me)(Bzl) |
| | Boc—Lys(Z)—Phe—N(Me)(Bzl) |
| 22-(2) | HCl.H—Phe—N(Me)(Bzl) |
| | Boc—Lys(Cl—Z)—Phe—N(Me)(Bzl) |
| 22-(3) | HCl.H—Phe—N(Me)(Bzl) |
| | Boc—Orn(Z)—Phe—N(Me)(Bzl) |
| 23-(1) | Boc—Asp(—Gln—NHBu$^t$)—Phe—N(Me)(Bzl) |
| | HCl.H—Asp(—Gln—NHBu$^t$)—Phe—N(Me)(Bzl) |
| 23-(2) | Boc—Lys(Cl—Z)—Phe—N(Me)(Bzl) |
| | HCl.H—Lys(Cl—Z)—Phe—N(Me)(Bzl) |
| 23-(3) | Boc—Lys(Z)—Phe—N(Me)(Bzl) |
| | HCl.H—Lys(Z)—Phe—N(Me)(Bzl) |
| 23-(4) | Boc—Orn(Z)—Phe—N(Me)(Bzl) |
| | HCl.H—Orn(Z)—Phe—N(Me)(Bzl) |

TABLE-continued

| | Formula |
|---|---|
| 24 | Boc—MePhe—N(Me)(Bzl) |
| | HCl.H—MePhe—N(Me)(Bzl) |
| 25-(1) | Boc—Phe—OH |
| | Boc—Phe—N(Me)(Bzl(m-F)) |
| 25-(2) | Boc—Phe—OH |
| | Boc—Phe—N(Me)(Bzl(o-CF₃)) |
| 25-(3) | Boc—Phe—OH |
| | Boc—Phe—N(Me)(Bzl(o-F)) |
| 25-(4) | Boc—Phe—OH |
| | Boc—Phe—N(Me)(CH₂Py(2)) |
| 25-(5) | Boc—Phe—OH |
| | Boc—Phe—N((CH₂)₂OH)(Bzl) |
| 26 | Boc—MePhe—OH |
| | Boc—MePhe—N(Me)(Bzl) |
| 27 | Boc—Asp(OBzl)—Phe—N(Me)(Bzl) |
| | Boc—Asp—Phe—N(Me)(Bzl) |
| 28 | HCl.H—N piperidine with OH and COOH substituents |

TABLE-continued

| Formula |
|---|

29-(1)

Boc—N(piperidine-4-OH)—COOH (2S)

HCl·H—Phe—N(Me)(Bzl)

29-(2)

Boc—N(piperidine-4-OH)—CO—Phe—N(Me)(Bzl)

HCl·H—MePhe—N(Me)(Bzl)

Boc—Pro—MePhe—N(Me)(Bzl)

29-(3)

HCl·H—Phe—N(Me)(Bzl(o-CF$_3$))

Boc—(2S,4R)—Pro(4OH)—Phe—N(Me)(Bzl(o-CF$_3$))

29-(4)

HCl·H—Phe—N(Me)(Bzl(m-F))

Boc—(2S,4R)—Pro(4OH)—Phe—N(Me)(Bzl(m-F))

29-(5)

HCl·H—Phe—N(Me)(Bzl(o-F))

Boc—(2S,4R)—Pro(4OH)—Phe—N(Me)(Bzl(o-F))

29-(6)

HCl·H—Phe—N(Me)(Bzl)

Boc—(2S,4R)—Pro(4OMe)—Phe—N(Me)(Bzl)

TABLE-continued

| | Formula |
|---|---|
| 29-(7) | HCl.H—Phe—N(Me)(Bzl) |
| | Boc—Ala—Phe—N(Me)(Bzl) |
| 29-(8) | HCl.H—Phe—N(Me)(Bzl) |
| | Boc—Thr—Phe—N(Me)(Bzl) |
| 29-(9) | HCl.H—Phe—N(Me)(Bzl) |
| | Boc—Met—Phe—N(Me)(Bzl) |
| 29-(10) | HCl.H—MePhe—N(Me)(Bzl) |
| | Boc—Ser(Bzl)—MePhe—N(Me)(Bzl) |
| 29-(11) | HCl.H—MePhe—N(Me)(Bzl) |
| | Z—Ser(Bu$^t$)—MePhe—N(Me)(Bzl) |
| 30-(1) | Boc—Tyr—Phe—N(Me)(CH$_2$Py(2)) |
| | Boc—(2S,4R)—Pro(4OH)—Tyr—N(Me)(CH$_2$Py(2)) |
| 30-(2) | Boc—Phe—N(Me)(CH$_2$Py(2)) |
| | Boc—(2S,4R)—Pro(4OH)—Phe—N(Me)(CH$_2$Py(2)) |

TABLE-continued

| | Formula |
|---|---|
| 30-(3) | Boc—Phe—N(CH₂)OAc / Bzl |
| | Boc—(2S,4R)—Pro(4OH)—Phe—N(CH₂)₂OAc / Bzl |
| 31 | Boc—Asp—Phe—N(Me)(Bzl) |
| | Boc—Asp(Gln—NHBuᵗ)—Phe—N(Me)(Bzl) |
| 32 | Boc—Phe—N((CH₂)₂OH)(Bzl) |
| | Boc—Phe—N((CH₂)₂OAc)(Bzl) |
| 33 | Z—Ser(Buᵗ)—MePhe—N(Me)(Bzl) |
| | H—Ser(Buᵗ)—MePhe—N(Me)(Bzl) |
| 34 | Boc—(2S,4R)—Pro(4OH)—OH |
| | Boc—(2S,4R)—Pro(4OMe)—OH |

Example No.

| 1 | Boc—(2S,4R)—Pro(4OH)—Phe—N(Me)(Bzl) |
|---|---|
| | (indol-3-yl)CO—(2S,4R)—Pro(4OH)—Phe—N(Me)(Bzl) |
| 2 | Boc—(2S,4R)—Pro(4OH)—Phe—N(Me)(Bzl) |
| | (indol-2-yl)CO—(2S,4R)—Pro(4OH)—Phe—N(Me)(Bzl) |
| 3 | Boc—(2S,4R)—Pro(4OH)—Phe—N(Me)(Bzl) |

TABLE-continued

| | Formula |
|---|---|
| | Ph-CH=CHCO—(2S,4R)—Pro(4OH)—Phe—N(Me)(Bzl) (trans) |
| 4 | HCl.H—(2S,4R)—Pro(4OH)—Phe—N(Me)(Bzl) |
| | Indol-3-yl-CH₂CO—(2S,4R)—Pro(4OH)—Phe—N(Me)(Bzl) |
| 5 | HCl.H—(2S,4R)—Pro(4OH)—Phe—N(Me)(Bzl) |
| | Ph-CH₂CO—(2S,4R)—Pro(4OH)—Phe—N(Me)(Bzl) |
| 6-(1) | Boc—Pro—Phe—N(Me)(Bzl) |
| | Indol-3-yl-CO—Pro—Phe—N(Me)(Bzl) |
| 6-(2) | Boc—D—Pro—Phe—N(Me)(Bzl) |
| | Indol-3-yl-CO—D—Pro—Phe—N(Me)(Bzl) |
| 6-(3) | Boc—Gly—Phe—N(Me)(Bzl) |
| | Indol-3-yl-CO—Gly—Phe—N(Me)(Bzl) |
| 6-(4) | Boc—Ser—Phe—N(Me)(Bzl) |

TABLE-continued

| | Formula |
|---|---|
| | ![indole]-CO—Ser—Phe—N(Me)(Bzl) |
| 6-(5) | Boc—Asn—Phe—N(Me)(Bzl) |
| | ![indole]-CO—Asn—Phe—N(Me)(Bzl) |
| 6-(6) | Boc—Aib—Phe—N(Me)(Bzl) |
| | ![indole]-CO—Aib—Phe—N(Me)(Bzl) |
| 7-(1) | Boc—(2S,4R)—Pro(4OH)—Phe—N(Me)(Bzl) |
| | HO-![indole]-CO—(2S,4R)—Pro(4OH)—Phe—N(Me)(Bzl) |
| 7-(2) | Boc—Pro—Phe—N(Me)(Bzl) |
| | ![indole]-CO—Pro—Phe—N(Me)(Bzl) |
| 8 | Boc—Pro—Phe—N(Me)(Bzl) |
| | Ph-CH=CHCO—Pro—Phe—N(Me)(Bzl) (trans) |
| 9-(1) | HCl·H—(2S,4R)—Pro(4OH)—Phe—N(Me)(Bzl) |

| TABLE-continued |
|---|
| Formula |

Ph-(CH₂)₂CO—(2S,4R)—Pro(4OH)—Phe—N(Me)(Bzl)

9-(2)

HCl.H—(2S,4R)—Pro(4OH)—Phe—N(Me)(Bzl)

Ph-(CH₂)₃CO—(2S,4R)—Pro(4OH)—Phe—N(Me)(Bzl)

9-(3)

HCl.H—(2S,4R)—Pro(4OH)—Phe—N(Me)(Bzl)

Ph-NHCH₂CO—(2S,4R)—Pro(4OH)—Phe—N(Me)(Bzl)

9-(4)

HCl.H—(2S,4R)—Pro(4OH)—Phe—N(Me)(Bzl)

HO-(5-hydroxyindol-3-yl)-CH₂CO—(2S,4R)—Pro(4OH)—Phe—N(Me)(Bzl)

9-(5)

HCl.H—(2S,4R)—Pro(4OH)—Phe—N(Me)(Bzl)

(pyrrol-2-yl)-CO—(2S,4R)—Pro(4OH)—Phe—N(Me)(Bzl)

10-(1)

Boc—(2S,4S)—Pro(4OH)—Phe—N(Me)(Bzl)

(indol-3-yl)-CO—(2S,4S)—Pro(4OH)—Phe—N(Me)(Bzl)

10-(2)

Boc—(S)—Azt—Phe—N(Me)(Bzl)

TABLE-continued

| | Formula |
|---|---|
| | (indol-3-yl)−CO−(S)−Azt−Phe−N(Me)(Bzl) |
| 10-(3) | Boc−Tpr−Phe−N(Me)(Bzl) |
| | (indol-3-yl)−CO−Tpr−Phe−N(Me)(Bzl) |
| 10-(4) | Boc−(2S,4R)−Pro(4OH)−Tyr−N(Me)(Bzl) |
| | (indol-3-yl)−CO−(2S,4R)−Pro(4OH)−Tyr−N(Me)(Bzl) |
| 11-(1) | HCl.H−(2S,4R)−Pro(4OH)−Phe−N(Me)(Bzl) |
| | (benzofuran-2-yl)−CO−(2S,4R)−Pro(4OH)−Phe−N(Me)(Bzl) |
| 11-(2) | HCl.H−(2S,4R)−Pro(4OH)−Phe−N(Me)(Bzl) |
| | (indazol-3-yl)−CO−(2S,4R)−Pro(4OH)−Phe−N(Me)(Bzl) |
| 12-(1) | Boc−(2S,4R)−Pro(4OH)−Tyr−N(Me)(Bzl) |
| | (indazol-3-yl)−CO−(2S,4R)−Pro(4OH)−Tyr−N(Me)(Bzl) |
| 12-(2) | Boc−(2S,4R)−Pro(4OH)−Tyr−N(Me)(Bzl) |

| | TABLE-continued |
|---|---|
| | Formula |

| | |
|---|---|
| | HO-[5-hydroxyindole]-CO—(2S,4R)—Pro(4OH)—Tyr—N(Me)(Bzl) |
| | [indole]-CO—Tpr—Phe—N(Me)(Bzl) |
| 13 | [indole]-CO—(2R,4R)—Tpr(O)—Phe—N(Me)(Bzl) |
| | [indole]-CO—(2R,4S)—Tpr(O)—Phe—N(Me)(Bzl) |
| 14 | [indole]-CO—Tpr—Phe—N(Me)(Bzl) |
| | [indole]-CO—(2R,4R)—Tpr(O$_2$)—Phe—N(Me)(Bzl) |
| 15 | [indole]-CO—(2S,4R)—Pro(4OH)—Phe—N(Me)(Bzl) |
| A | [N-CH$_2$CO$_2$Bu$^t$ indole]-CO—(2S,4R)—Pro(4OCH$_2$CO$_2$Bu$^t$)—Phe—N(Me)(Bzl) |
| B | [N-CH$_2$CO$_2$Bu$^t$ indole]-CO—(2S,4R)—Pro(4OH)—Phe—N(Me)(Bzl) |
| 16 | [N-CH$_2$CO$_2$Bu$^t$ indole]-CO—(2S,4R)—Pro(4OH)—Phe—N(Me)(Bzl) |

| | Formula |
|---|---|
| | ![indole with N-CH2CO2H]—CO—(2S,4R)—Pro(4OH)—Phe—N(Me)(Bzl) |
| 17 | ![indole with N-CH2CO2H]—CO—(2S,4R)—Pro(4OH)—Phe—N(Me)(Bzl) |
| | ![indole with N-CH2CONH(CH2)2NMe2]—CO—(2S,4R)—Pro(4OH)—Phe—N(Me)(Bzl) · HCl |
| 18 | ![indole NH]—CO—(2S,4R)—Pro(4OH)—Phe—N(Me)(Bzl) |
| | ![indole with N-(CH2)2NMe2]—CO—(2S,4R)—Pro(4OH)—Phe—N(Me)(Bzl) |
| 19 | ![indole NH]—CO—(2S,4R)—Pro(4OH)—Phe—N(Me)(Bzl) |
| | ![indole NH]—CO—(2S,4R)—Pro(4OMs)—Phe—N(Me)(Bzl) |
| 20 | ![indole NH]—CO—(2S,4R)—Pro(4OMs)—Phe—N(Me)(Bzl) |
| | ![indole NH]—CO—(2S,4S)—Pro(4NH2)—Phe—N(Me)(Bzl) |
| 21 | ![indole NH]—CO—(2S,4S)—Pro(4NH2)—Phe—N(Me)(Bzl) |

TABLE-continued

Formula

[Indole]—CO—(2S,4S)—Pro(4NH₂)—Phe—N(Me)(Bzl) · HCl

22  [Indole]—CO—(2S,4S)—Pro(4NH₂)—Phe—N(Me)(Bzl)

[Indole]—CO—(2S,4S)—Pro(4NHCOCO₂Et)—Phe—N(Me)(Bzl)

23  HCl·H—(2S,4R)—Pro(4OCONH₂)—Phe—N(Me)(Bzl)

[Indazole]—CO—(2S,4R)—Pro(4OCONH₂)—Phe—N(Me)(Bzl)

24  [Indole, N-(CH₂)₂NMe₂]—CO—(2S,4R)—Pro(4OH)—Phe—N(Me)(Bzl)

[Indole, N-(CH₂)₂NMe₂]—CO—(2S,4R)—Pro(4OH)—Phe—N(Me)(Bzl) · HCl 25-(1)  HCl·H—(2S,4R)—Pro(4OCONH₂)—Phe—N(Me)(Bzl)

[Indole]—CO—(2S,4R)—Pro(4OCONH₂)—Phe—N(Me)(Bzl)

25-(2)  HCl·H—(2S,4R)—Pro(4OCH₂CO₂Et)—Phe—N(Me)(Bzl)

[Indole]—CO—(2S,4R)—Pro(4OCH₂CO₂Et)—Phe—N(Me)(Bzl)

| | TABLE-continued |
|---|---|
| | Formula |
| 26 | 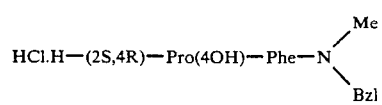 |
| | 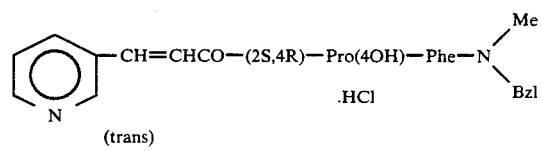 |
| 27 | 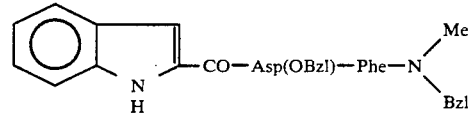 |
| | 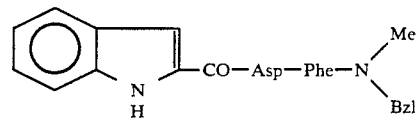 |
| 28 | 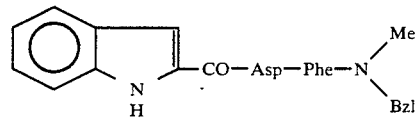 |
| | 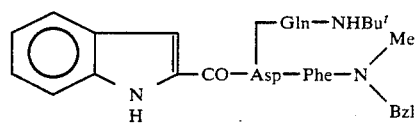 |
| 29 | 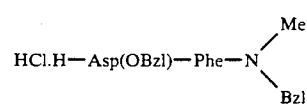 |
| | 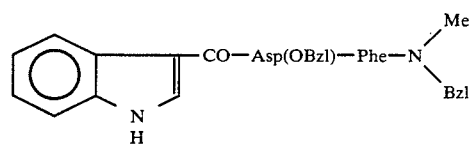 |
| 30 | 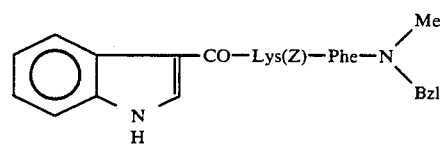 |
| | 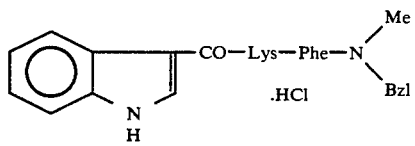 |
| 31 | 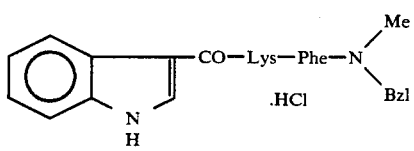 |

TABLE-continued

| | Formula |
|---|---|
| | Indole-3-CO-Lys(Et₂N(CH₂)₂CO)-Phe-N(Me)(Bzl) · HCl |
| 32 | Indole-3-CO-Lys(Boc-Thr)-Phe-N(Me)(Bzl) |
| | Indole-3-CO-Lys(Ac-Thr)-Phe-N(Me)(Bzl) |
| 33 | Indole-3-CO-Lys-Phe-N(Me)(Bzl) · HCl |
| | Indole-3-CO-Lys(COCH₂N(CH₂CO₂Buᵗ)(Boc))-Phe-N(Me)(Bzl) |
| 34 | Indole-3-CO-Lys-Phe-N(Me)(Bzl) · HCl |
| | Indole-3-CO-Lys(COCH₂-morpholino)-Phe-N(Me)(Bzl) |
| 35 | 1-Me-Indole-3-CO-(2S,4R)-Pro(4OH)-Phe-N(Me)(Bzl) |

TABLE-continued

| | Formula |
|---|---|
| | (1-Me-indol-3-yl)-CO—(2S,4R)-Pro(4OAc)—Phe—N(Me)(Bzl) |
| 36 | (indol-3-yl)-CO—(2S,4S)-Pro(4NH₂)—Phe—N(Me)(Bzl) |
| | (indol-3-yl)-CO—(2S,4S)-Pro(4NHCOCH₂NHZ)—Phe—N(Me)(Bzl) |
| 37 | (indol-3-yl)-CO—(2S,4S)-Pro(4NHCOCH₂NHZ)—Phe—N(Me)(Bzl) |
| | (indol-3-yl)-CO—(2S,4S)-Pro(4NHCOCH₂NH₂)—Phe—N(Me)(Bzl) · HCl |
| 38 | (indol-3-yl)-CO—(2S,4S)-Pro(4NHCO(CH₂)₂CH(S)(NHZ)CO₂Bzl)—Phe—N(Me)(Bzl) |
| | (indol-3-yl)-CO—(2S,4S)-Pro(4NHCO(CH₂)₂CH(S)(NH₂)CO₂H)—Phe—N(Me)(Bzl) |
| 39 | (indol-3-yl)-CO—(2S,4S)-Pro(4NH₂)—Phe—N(Me)(Bzl) |
| | (indol-3-yl)-CO—(2S,4S)-Pro(4NHCO(CH₂)₂COONa)—Phe—N(Me)(Bzl) |
| 40 | (indol-3-yl)-CO—(2S,4S)-Pro(4NHCOCO₂Et)—Phe—N(Me)(Bzl) |

TABLE-continued

| | Formula |
|---|---|
| | (indole-NH)—CO—(2S,4S)—Pro(4NHCOCO₂Na)—Phe—N(Me)(Bzl) |
| 41 | (indole-N-CH₂CO₂H)—CO—(2S,4R)—Pro(4OH)—Phe—N(Me)(Bzl) |
| | (indole-N-CH₂CO₂Na)—CO—(2S,4R)—Pro(4OH)—Phe—N(Me)(Bzl) |
| 42 | (indole-N-Me)—CO—(2S,4R)—Pro(4OTs)—PHe—N(Me)(Bzl) |
| | (indole-N-Me)—CO—(2S,4S)—Pro(4SMe)—Phe—N(Me)(Bzl) |
| 43-(1) | Boc—Met—Phe—N(Me)(Bzl) |
| | (indole-N-Me)—CO—Met—Phe—N(Me)(Bzl) |
| 43-(2) | Boc—Thr—Phe—N(Me)(Bzl) |
| | (indole-N-Me)—CO—Thr—Phe—N(Me)(Bzl) |
| 43-(3) | Boc—Ala—Phe—N(Me)(Bzl) |

TABLE-continued

Formula

[Indole-N-Me]-CO—Ala—Phe—N(Me)(Bzl)

43-(4)

Boc—(2S,4R)—Pro(4OMe)—Phe—N(Me)(Bzl)

[Indole-N-Me]-CO—(2S,4R)—Pro(4OMe)—Phe—N(Me)(Bzl)

43-(5)

Boc—Ser(Bzl)—MePhe—N(Me)(Bzl)

[Indole-N-Me]-CO—Ser(Bzl)—MePhe—N(Me)(Bzl)

44-(1)

HCl.H—Asp(OBzl)—Phe—N(Me)(Bzl)

[Indole-NH]-CO—Asp(OBzl)—Phe—N(Me)(Bzl)

44-(2)

HCl.H—Asp(—Gln—NHBu$^t$)—Phe—N(Me)(Bzl)

[Indole-NH]-CO—Asp(—Gln—NHBu$^t$)—Phe—N(Me)(Bzl)

44-(3)

HCl.H—Asp(OBzl)—Phe—N(Me)(Bzl)

[Indole-NH]-CH$_2$CO—Asp(OBzl)—Phe—N(Me)(Bzl)

TABLE-continued

Formula 44-(4)

HCl.H—Lys(Cl—Z)—Phe—N(Me)(Bzl)

[indole]-CO—Lys(Cl—Z)—Phe—N(Me)(Bzl)

44-(5)

HCl.H—Lys(Z)—Phe—N(Me)(Bzl)

[indole]-CH₂CO—Lys(Z)—Phe—N(Me)(Bzl)

44-(6)

HCl.H—(2S,4R)—Pro(4OH)—Phe—N(Me)(Bzl)

[5-Cl-indazole]-CH₂CO—(2S,4R)—Pro(4OH)—Phe—N(Me)(Bzl)

44-(7)

HCl.H—(2S,4R)—Pro(4OH)—Phe—N(Me)(Bzl)

HO—[C₆H₄]—(CH₂)₂CO—(2S,4R)—Pro(4OH)—Phe—N(Me)(Bzl)

44-(8)

HCl.H—(2S,4R)—Pro(4OH)—Phe—N(Me)(Bzl)

[N-Boc-indoline]-CO—(2S,4R)—Pro(4OH)—Phe—N(Me)(Bzl)

44-(9)

HCl.H—(2S,4R)—Pro(4OH)—Phe—N(Me)(Bzl)

[N-Me-indole]-CO—(2S,4R)—Pro(4OH)—Phe—N(Me)(Bzl)

| | TABLE-continued |
|---|---|
| | Formula |

44-(10)

HCl.H—(2S,4R)—Pro(4OH)—Phe—N(Me)(Bzl)

[indole-3-yl]—CO—(2S,4R)—Pro(4OH)—Phe—N(Me)(Bzl)  
(N-Pr$^i$)

44-(11)

HCl.H—(2S,4R)—Pro(4OH)—Phe—N(Me)(Bzl)

[5-Cl-indol-2-yl (NH)]—CO—(2S,4R)—Pro(4OH)—Phe—N(Me)(Bzl)

44-(12)

HCl.H—(2S,4R)—Pro(4OH)—Phe—N(Me)(Bzl)

HO—C$_6$H$_4$—CH=CHCO—(2S,4R)—Pro(4OH)—Phe—N(Me)(Bzl)  
(trans)

44-(13)

HCl.H—(2S,4R)—Pro(4OH)—Phe—N(Me)(Bzl)

(HO, 3,5-(MeO)$_2$-C$_6$H$_2$)—CH=CHCO—(2S,4R)—Pro(4OH)—Phe—N(Me)(Bzl)  
(trans)

44-(14)

HCl.H—(2S,4R)—Pro(4OH)—Phe—N(Me)(Bzl)

Me$_2$CH(CH$_2$)$_2$CO—(2S,4R)—Pro(4OH)—Phe—N(Me)(Bzl)

44-(15)

HCl.H—(2S,4R)—Pro(4OH)—Phe—N(Me)(Bzl)

[5-MeO-indol-2-yl (NH)]—CO—(2S,4R)—Pro(4OH)—Phe—N(Me)(Bzl)

TABLE-continued
| Formula |
|---|
44-(16)
HCl.H—(2S,4R)—Pro(4OH)—Phe—N(Me)(Bzl)
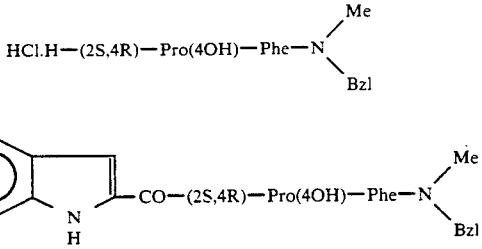
—CO—(2S,4R)—Pro(4OH)—Phe—N(Me)(Bzl)
44-(17)
HCl.H—(2S,4R)—Pro(4OH)—Phe—N(Me)(Bzl)
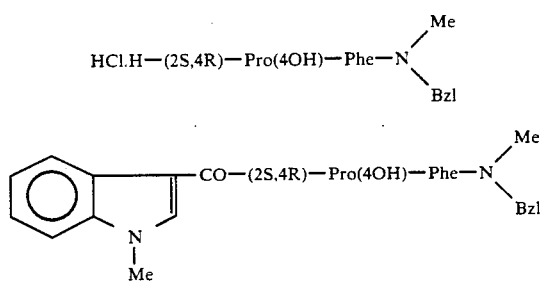
—CO—(2S,4R)—Pro(4OH)—Phe—N(Me)(Bzl)
44-(18)
HCl.H—(2S,4R)—Pro(4OH)—Phe—N(Me)(Bzl)
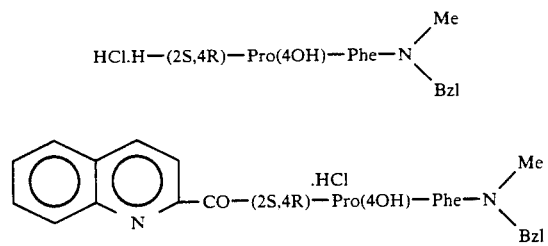
—CO—(2S,4R)—Pro(4OH)—Phe—N(Me)(Bzl) .HCl
44-(19)
HCl.H—(2S,4R)—Pro(4OH)—Phe—N(Me)(Bzl)
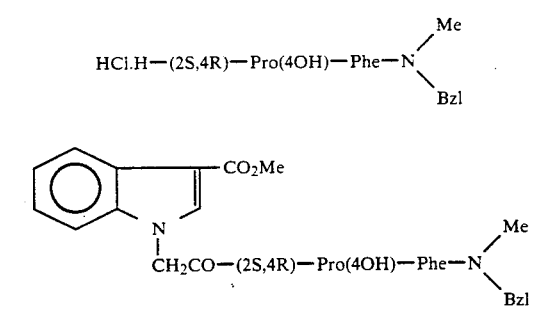
CH$_2$CO—(2S,4R)—Pro(4OH)—Phe—N(Me)(Bzl)
44-(20)
HCl.H—Ser—Phe—N(Me)(Bzl)
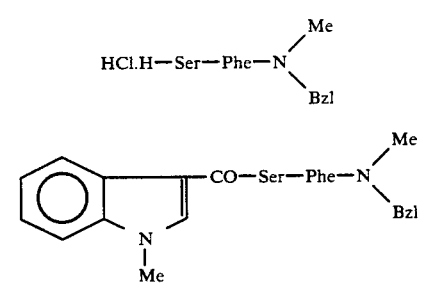
—CO—Ser—Phe—N(Me)(Bzl)
44-(21)
HCl.H—(2S,4R)—Pro(4OH)—Tyr—N(Me)(Bzl)
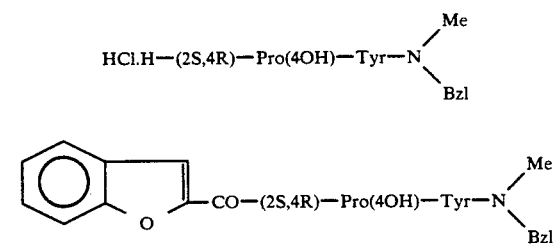
—CO—(2S,4R)—Pro(4OH)—Tyr—N(Me)(Bzl)

TABLE-continued
Formula
44-(22)
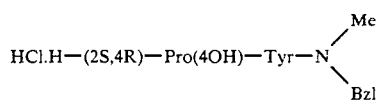
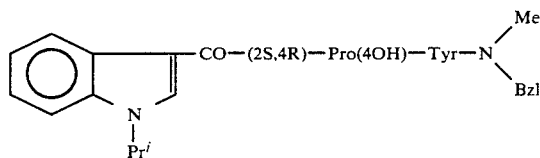
44-(23)
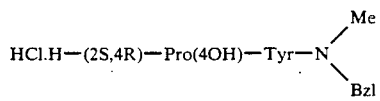
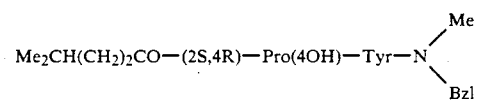
44-(24)
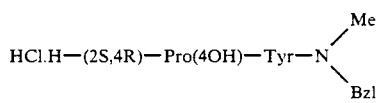
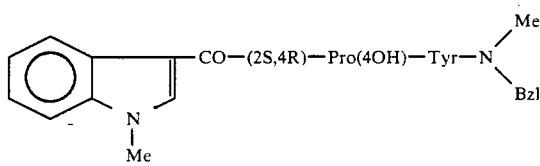
44-(25)
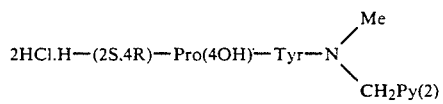
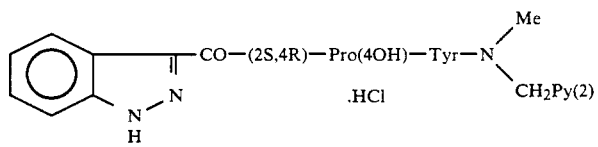
44-(26)
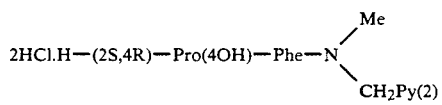
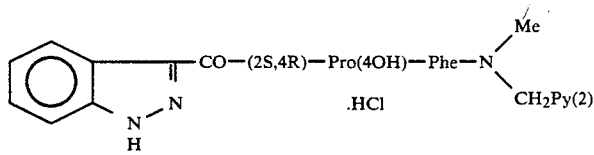
44-(27)
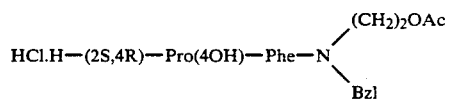
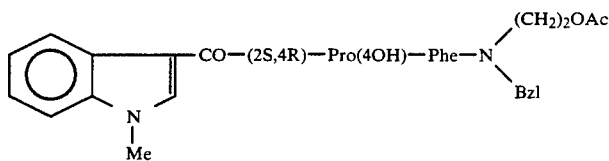

TABLE-continued
Formula
44-(28)
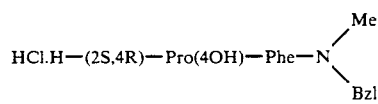
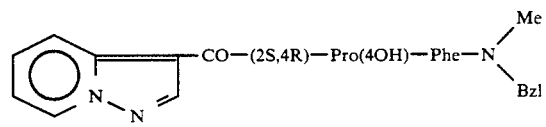
44-(29)
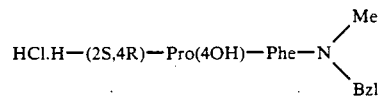
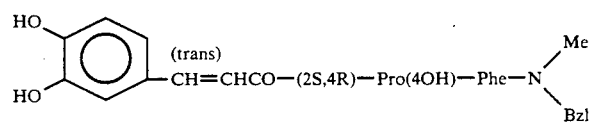
44-(30)
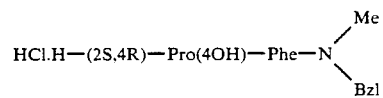
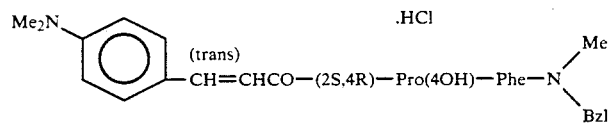
44-(31)
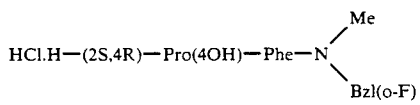
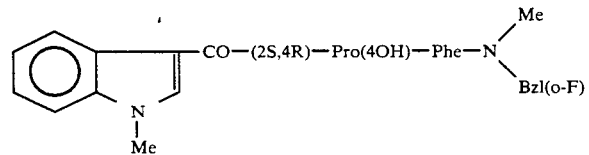
44-(32)
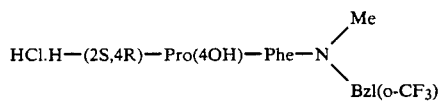
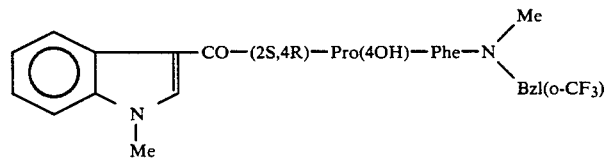
44-(33)
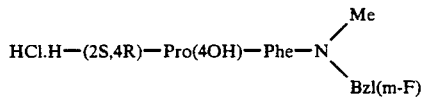
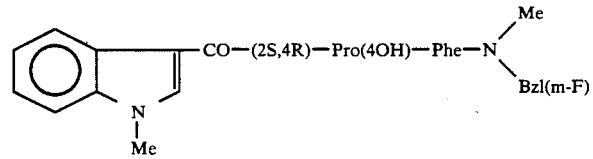

| | |
|---|---|
| | TABLE-continued |
| | Formula |
| 44-(34) | HCl.H—Pro—Phe—N(Me)(Bzl) |
| | [1-methylindol-3-yl]-CO—Pro—Phe—N(Me)(Bzl) |
| 45-(1) | [indol-3-yl]-CO—Asp(OBzl)—Phe—N(Me)(Bzl) |
| | [indol-3-yl]-CO—Asp—Phe—N(Me)(Bzl) |
| 45-(2) | [indol-3-yl]-CH₂CO—Asp(OBzl)—Phe—N(Me)(Bzl) |
| | [indol-3-yl]-CH₂CO—Asp—Phe—N(Me)(Bzl) |
| 46-(1) | [indol-3-yl]-CO—Asp—Phe—N(Me)(Bzl) |
| | [indol-3-yl]-CO—Asp(Gln—NHBuᵗ)—Phe—N(Me)(Bzl) |
| 46-(2) | [indol-2-yl]-CO—Asp—Phe—N(Me)(Bzl) |
| | [indol-2-yl]-CO—Asp(Thr—NH₂)—Phe—N(Me)(Bzl) |

Note: The formulas above are structural representations where the indolyl groups are drawn as fused bicyclic rings (indole) with substitution at the 2- or 3-position as indicated.

| | TABLE-continued |
|---|---|
| | Formula |
46-(3)
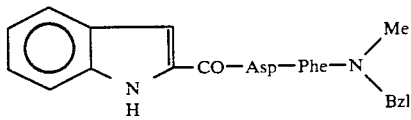
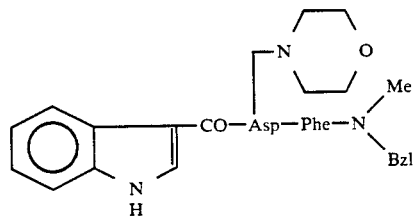
46-(4)
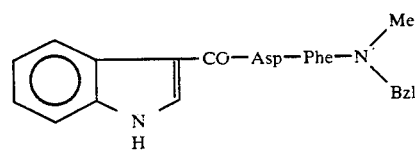
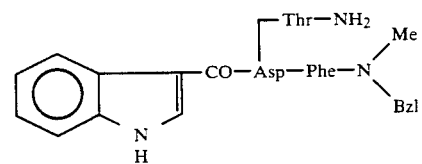
46-(5)
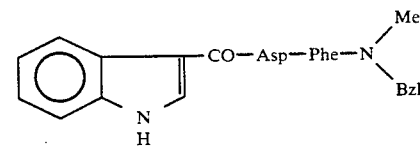
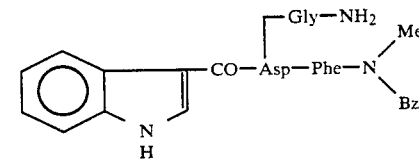
46-(6)
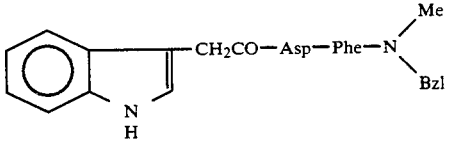
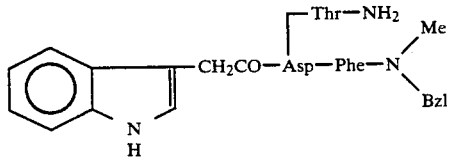
47-(1)
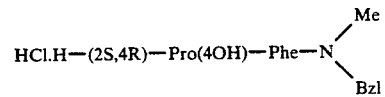
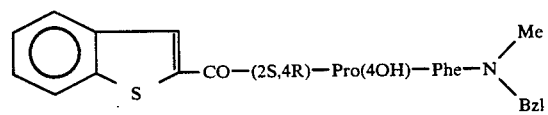

TABLE-continued

| | Formula |
|---|---|
| 47-(2) | HCl.H—Ser—Phe—N(Me)(Bzl) |
| | PhCH=CHCO—Ser—Phe—N(Me)(Bzl) (trans) |
| 47-(3) | HCl.H—(2S,4R)—Pro(4OH)—Tyr—N(Me)(Bzl) |
| | Me₂CHCH₂CO—(2S,4R)—Pro(4OH)—Tyr—N(Me)(Bzl) |
| 47-(4) | H—Ser(Buᵗ)—MePhe—N(Me)(Bzl) |
| | PhCH=CHCO—Ser(Buᵗ)—MePhe—N(Me)(Bzl) (trans) |
| 47-(5) | HCl.H—(2S,4R)—Pro(4OH)—Phe—N(Me)(Bzl) |
| | Bz—(2S,4R)—Pro(4OH)—Phe—N(Me)(Bzl) |
| 48-(1) | HCl.H—Lys(Z)—Phe—N(Me)(Bzl) |
| | Indol-3-yl-CO—Lys(Z)—Phe—N(Me)(Bzl) |
| 48-(2) | HCl.H—Orn(Z)—Phe—N(Me)(Bzl) |
| | Indol-3-yl-CO—Orn(Z)—Phe—N(Me)(Bzl) |
| 48-(3) | 2HCl.H—(2S,4R)—Pro(4OH)—Tyr—N(Me)(CH₂Py(2)) |

| | Formula |
|---|---|
| | Indol-3-yl-CO—(2S,4R)—Pro(4OH)—Tyr—N(Me)(CH₂Py(2)) · HCl |
| 48-(4) | 2HCl·H—(2S,4R)—Pro(4OH)—Phe—N(Me)(CH₂Py(2)) |
| | Indol-3-yl-CO—(2S,4R)—Pro(4OH)—Phe—N(Me)(CH₂Py(2)) · HCl |
| 49-(1) | Indol-3-yl-CH₂CO—Lys(Z)—Phe—N(Me)(Bzl) |
| | Indol-3-yl-CH₂CO—Lys—Phe—N(Me)(Bzl) · HCl |
| 49-(2) | Indol-3-yl-CO—Orn(Z)—Phe—N(Me)(Bzl) |
| | Indol-3-yl-CO—Orn—Phe—N(Me)(Bzl) · HCl |
| 50-(1) | Indol-3-yl-CO—Lys—Phe—N(Me)(Bzl) · HCl |
| | Indol-3-yl-CO—Lys(Boc-Thr)—Phe—N(Me)(Bzl) |
| 50-(2) | Indol-3-yl-CO—Lys—Phe—N(Me)(Bzl) · HCl |

TABLE-continued
Formula
| | |
|---|---|
| | 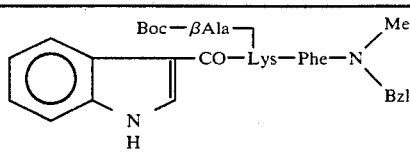 |
| 50-(3) | 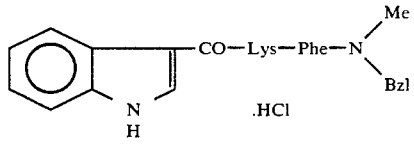 |
| | 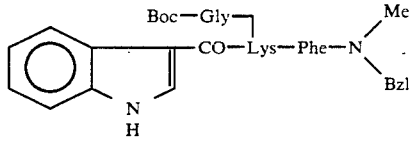 |
| 50-(4) | 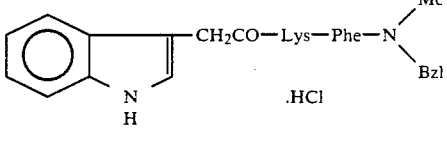 |
| | 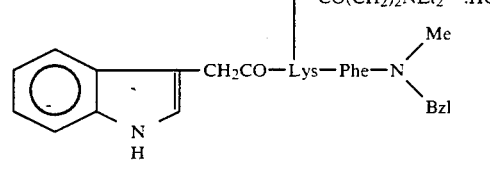 |
| 50-(5) | 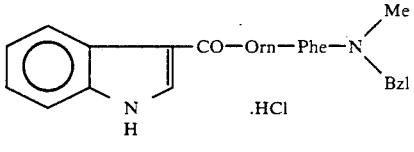 |
| | 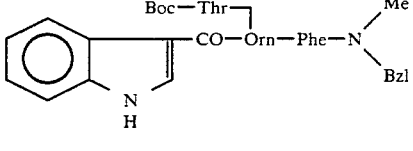 |
| 50-(6) | 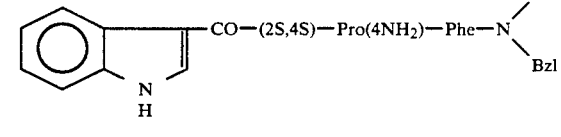 |
| | 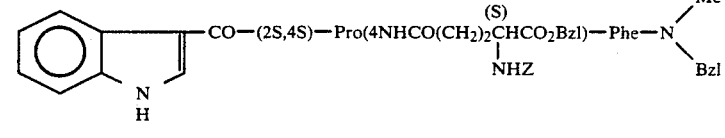 |
| 50-(7) | 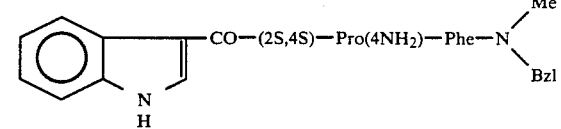 |

TABLE-continued

| | Formula |
|---|---|
| | Indole-CO—(2S,4S)—Pro(4NHCOCH(S)(CH₂)₂CO₂Bzl)—Phe—N(Me)(Bzl), with NHZ on the CH |
| 51-(1) | Indole-CO—Orn(Boc-Thr)—Phe—N(Me)(Bzl) |
| | Indole-CO—Orn(Ac-Thr)—Phe—N(Me)(Bzl) |
| 51-(2) | Boc-N-piperidine(5-OH)(2-CO)—Phe—N(Me)(Bzl) |
| | Indole-CO—N-piperidine(5-OH)(2-CO)—Phe—N(Me)(Bzl) |
| 51-(3) | Boc—Pro—MePhe—N(Me)(Bzl) |
| | Indole-CO—Pro—MePhe—N(Me)(Bzl) |
| 51-(4) | Boc—Pro—Phe—N(tetrahydroisoquinoline) |
| | Indole-CO—Pro—Phe—N(tetrahydroisoquinoline) |
| 52-(1) | Indole-CO—Lys(Boc-βAla)—Phe—N(Me)(Bzl) |

| TABLE-continued |
|---|
| Formula |

[Structure: Indole with HCl.H—βAla— attached, CO—Lys—Phe—N(Me)(Bzl)]

52-(2)

[Structure: Indole with Boc—Gly— attached, CO—Lys—Phe—N(Me)(Bzl)]

[Structure: Indole with HCl.H—Gly— attached, CO—Lys—Phe—N(Me)(Bzl)]

53-(1)

[Structure: Benzofuran—CO—Ser(Bu$^t$)—MePhe—N(Me)(Bzl)]

[Structure: Benzofuran—CO—Ser—MePhe—N(Me)(Bzl)]

53-(2)

[Structure: Phenyl—CH=CHCO (trans)—Ser(Bu$^t$)—MePhe—N(Me)(Bzl)]

[Structure: Phenyl—CH=CHCO (trans)—Ser—MePhe—N(Me)(Bzl)]

53-(3)

[Structure: N-(CH$_2$CO$_2$Bu$^t$)-indole—CO—(2S,4R)—Pro(4OCH$_2$CO$_2$Bu$^t$)—Phe—N(Me)(Bzl)]

[Structure: N-(CH$_2$CO$_2$H)-indole—CO—(2S,4R)—Pro(4OCH$_2$CO$_2$H)—Phe—N(Me)(Bzl)]

54-(1)

H—Ser(Bu$^t$)—MePhe—N(Me)(Bzl)

TABLE-continued

| | Formula |
|---|---|
| | [indol-3-yl, N-Me]—CO—Ser(Bu$^t$)—MePhe—N(Me)(Bzl) |
| 54-(2) | H—Ser(Bu$^t$)—MePhe—N(Me)(Bzl) |
| | [benzofuran-2-yl]—CO—Ser(Bu$^t$)—MePhe—N(Me)(Bzl) |
| 55 | [indol-3-yl, N-Me]—CO—(2S,4R)—Pro(4OH)—Phe—N(Me)(Bzl) |
| | [indol-3-yl, N-Me]—CO—(2S,4R)—Pro(4OTs)—Phe—N(Me)(Bzl) |
| 56-(1) | [indol-3-yl, N-H]—CO—(2S,4S)—Pro(4NHCOCH(CH$_2$)$_2$CO$_2$Bzl)(S)(NHZ)—Phe—N(Me)(Bzl) |
| | [indol-3-yl, N-H]—CO—(2S,4S)—Pro(4NHCOCH(CH$_2$)$_2$CO$_2$H)(NH$_2$)—Phe—N(Me)(Bzl) |
| 56-(2) | [indol-3-yl, N-Me]—CO—Ser(Bzl)—MePhe—N(Me)(Bzl) |
| | [indol-3-yl, N-Me]—CO—Ser—MePhe—N(Me)(Bzl) |
| 57 | [indol-3-yl, N-H]—CO—(2S,4S)—Pro(4NH$_2$)—Phe—N(Me)(Bzl) |

TABLE-continued

| | Formula |
|---|---|
| | Trp—CO—(2S,4S)—Pro(4NHMs)—Phe—N(Me)(Bzl) |
| 58 | Trp—CO—(2S,4S)—Pro(4NH₂)—Phe—N(Me)(Bzl) |
| | Trp—CO—(2S,4S)—Pro(4NHCO(CH₂)₂NEt₂)—Phe—N(Me)(Bzl) · HCl |
| 59 | Trp—CO—(2S,4R)—Pro(4OCH₂CO₂Et)—Phe—N(Me)(Bzl) |
| | Trp—CO—(2S,4R)—Pro(4OCH₂CO₂Na)—Phe—N(Me)(Bzl) |
| 60 | (N-CH₂CO₂H indole)—CO—(2S,4R)—Pro(4OCH₂CO₂H)—Phe—N(Me)(Bzl) |
| | (N-CH₂CO₂Na indole)—CO—(2S,4R)—Pro(4OCH₂CO₂Na)—Phe—N(Me)(Bzl) |
| 61 | (N-Boc indoline)—CO—(2S,4R)—Pro(4OH)—Phe—N(Me)(Bzl) |
| | (indoline)—CO—(2S,4R)—Pro(4OH)—Phe—N(Me)(Bzl) · HCl |
| 62 | Trp—CO—Orn—Phe—N(Me)(Bzl) · HCl |

TABLE-continued

| | Formula |
|---|---|
| 63 | (indole-2)-CO-Orn(-CO(CH₂)₂CO₂H)-Phe-N(Me)(Bzl), indole NH |
| | (1-Me-indole-3)-CO-(2S,4R)-Pro(4OH)-Phe-N((CH₂)₂OAc)(Bzl) |
| | (1-Me-indole-3)-CO-(2S,4R)-Pro(4OH)-Phe-N((CH₂)₂OH)(Bzl) |

Preparation 1

A solution of Starting Compound (5.48 g) and NMM (2.09 g) in methylene chloride (50 ml) was cooled at −20° C. To this solution was added dropwise isobutyl chloroformate (2.82 g) maintaining the temperature between −22° C. to −20° C. in 7 minutes. After stirring the mixture for 20 minutes at the same temperature, the solution was cooled to −35° C. and HNMeBzl (2.50 g) was added dropwise to the solution. The reaction mixture was stirred for 2 hours during which period the temperature was gradually raised to −2° C. The solution was washed successively with water (twice), diluted sodium hydrogencarbonate solution (twice), water, 0.5N hydrochloric acid (twice) and sodium chloride solution, and dried over magnesium sulfate. After evaporation, the solidified residue was pulverized in hot IPE (10 ml), and after cooling, n-hexane (30 ml) was added to the mixture. The crystalline solid was filtered, washed with n-hexane (5 ml×2), and dried to give Object Compound (6.49 g).

mp: 90°–91.5° C.
IR (Nujol): 3380, 1690, 1645 (sh), 1635, 1525 cm$^{-1}$
NMR (CDCl₃, δ): 1.37 (s) and 1.43 (s)(9H), 2.67 (s) and 2.87 (s)(3H), 3.04 (2H, d, J=7Hz), 4.28 (ABq, J=14Hz) and 4.52 (s)(2H), 4.90 (1H, m), 5.4 (1H, m), 7.0–7.4 (10H)
Elemental Analysis. Calculated for C₂₂H₂₈N₂O₃: C 71.71, H 7.66, N 7.60; Found: C 72.04, H 7.65, N 7.65
$[\alpha]_D^{25}$ +19.99° (C=1.035, CHCl₃)

Preparation 2

To an ice-cooled solution of Starting Compound (3.0 g) and anisole (3 ml) in methylene chloride (10 ml) was added TFA (12 ml). The solution was stirred for 15 minutes at this temperature and for additional half an hour at room temperature. After evaporation, addition and re-evaporation of 4N-HCL/DOX were repeated twice (4.1 ml and 2.0 ml, respectively). The residue was dissolved in ether (15 ml), and crystallized by seeding. After standing overnight, the crystals were filtered, washed with ether, and dried to give Object Compound (2.12 g).

mp: 133°–135° C.
IR (Nujol): 3400, 1650 cm$^{-1}$
NMR (CDCl₃, δ): 2.43 (s) and 2.70 (s) (3H), 3.5 (2H, m), 4.13 and 4.75 (2H, ABq, J=14Hz), 5.0 (1H, m), 7.0–7.4 (10H, m), 8.85 (3H, br s)
Elemental Analysis. Calculated for C₁₇H₂₀N₂O.HCl.½H₂O: C 65.06, H 7.07, N 8.93; Found: C 65.53, H 6.86, N 8.90
$[\alpha]_D^{25}$ +57.78° (C=1.066, CHCl₃)

Preparation 3

To an ice-cooled solution of Boc-(2S,4R)-Pro(4OH)-OH (1.80 g), Starting Compound (2.37 g), and HOBT (1.05 g) in methylene chloride (50 ml), was added WSC (1.21 g). The solution was stirred at the same temperature for two hours and at room temperature for two hours. After concentration, the product was extracted with ethyl acetate and the organic layer was washed successively with water, diluted sodium hydrogencarbonate solution, 0.5N hydrochloric acid and sodium chloride solution, and dried over anhydrous magnesium sulfate to give Object Compound (3.82 g) as an amorphous solid.

NMR (DMSO-d₆, δ): 1.25 and 1.47 (9H, s), 1.5–2.1 (2H, m), 2.78 and 2.85 (3H, s), 2.8–3.1 (2H, m), 3.2–3.5 (3H, m), 4.1–4.25 (2H, m), 4.35–4.6 (2H, m), 4.8–5.1 (2H, m), 7.0–7.35 (10H, m), 8.3–8.4 (1H, m)

Preparation 4

Starting Compound (3.0 g) was dissolved in methylene chloride (30 ml), and to the solution 4N-HCl/DOX (30 ml) was added under ice-cooling and the solution was stirred at the same temperature for 10 minutes and further at room temperature for 40 minutes. After evaporation, the residue was triturated with IPE, filtered, washed with the same solvent, and dried under vacum to give Object Compound 2.90 g).

NMR (DMSO-d₆, δ): 1.7–1.9 (1H, m), 2.2–2.4 (1H, m), 2.75 (s) and 2.85 (s) (3H), 2.8–3.2 (3H, m), 3.2–3.4 (1H, m), 4.2–4.7 (4H, m), 4.85–5.05 (1H, m), 7.0–7.4 (10H, m), 8.59 (1H, broad), 9.24 (1H, d, J=8Hz), 10.29 (1H, broad)

Preparation 5

The object compounds were obtained according to a similar manner to that of Preparation 3.

(1)

IR (CH$_2$Cl$_2$): 3400, 1700, 1650, 1505, 1395, 1170 cm$^{-1}$

NMR (CDCl$_3$, δ): 1.47 (9H, s), 1.7–2.2 (4H, m), 2.67 and 2.87 (3H, s), 2.92–3.1 (2H, m), 3.27–3.52 (2H, m), 4.3 (1H, m), 4.40 and 4.62 (2H, ABq, J=14Hz), 5.20 (1H, dt, J=8Hz and 6Hz), 6.95–7.4 (10H, m)

(2)

IR (CH ): 3450, 1700, 1650 cm$^{-1}$

NMR (CDCl$_3$, δ): 1.46 (9H, s), 1.8–1.9 (2H, m), 1.95–2.1 (2H, m), 2.58 and 2.81 (3H, s), 3.01 and 3.02 (2H, d, J=7.2Hz), 3.5 (2H, m), 4.2–4.3 (1H, m), 4.38 and 4.56 (2H, ABq, J=14.5Hz), 5.18 (1H, d, J=7Hz), 6.7–7.0 (1H, m), 7.07–7.35 (10H, m)

(3)

IR (Neat): 3300, 1710, 1635, 1495 cm$^{-1}$

NMR (DMSO$_6$, δ): 1.37 (9H, s), 2.73 (s) and 2.79 (s)(3H), 2.75–3.15 (2H, m), 3.35–3.70 (2H, m), 4.20–4.70 (2H, m), 4.75–5.20 (1H, m), 6.70–7.45 (11H, m), 8.00–8.35 (1H, m)

(4)

IR (Neat): 3300, 1710, 1640, 1630, 1490 cm$^{-1}$

NMR (DMSO-d$_6$, δ): 1.37 (9H, s), 2.71 (s) and 2.77 (s)(3H), 2.7–3.2 (2H, m), 3.3–3.6 (2H, m), 3.8–4.1 (1H, m), 4.43 (2H, s), 4.73 (1H, t, J=6Hz), 4.8–5.2 (1H, m), 6.4–6.8 (1H, m), 6.9–7.4 (10H, m), 8.0–8.2 (1H, m)

(5)

IR (Nujol): 3400, 3350, 3300, 3200, 1690, 1650, 1525 cm$^{-1}$

NMR (DMSO-d$_6$, δ): 1.36 (9H, s), 2.20–2.45 (2H, m), 2.70 (s) and 2.75 (s)(3H), 2.75–3.15 (2H, m), 4.00–4.60 (3H, m), 4.75–5.10 (1H, m), 6.83 (2H, broad s), 6.90–7.50 (11H, m), 7.90–8.20 (1H, m)

(6)

IR (Neat): 3320, 1720, 1705, 1690, 1650, 1640, 1630 cm$^{-1}$

NMR (DMSO-d$_6$, δ): 1.20 (s), 1.26 (s) and 1.29 (s)(6H), 1.36 (9H, s), 2.6–3.2 (2H, m), 2.72 (s) and 2.78 (s)(3H), 4.2–4.7 (2H, m), 4.8–5.2 (1H, m), 6.6–6.9 (1H, m), 7.0–7.4 (10H, m), 7.4–7.7 (1H, m)

Preparation 6

In a mixture of water (10 ml) and dioxane (5 ml), Starting Compound (1.0 g) was suspended. To the mixture TEA (1.06 ml) and di-tert-butyl dicarbonate (1.83 g) was added successively under ice-cooling. The mixture was stirred overnight at room temperature, then water (20 ml) was added. After washing with ethyl acetate (20 ml), the aqueous layer was cooled with ice bath and acidified with 5N-hydrochloric acid. The product was extracted with ethyl acetate, and the organic layer was washed with brine, dried over anhydrous magnesium sulfate and evaporated. The residue was crystallized with a mixture of ethyl acetate and IPE, filtered and dried to give Object Compound (1.34 g).

mp: 145°–146° C.

IR (Nujol): 3450, 1735, 1675 cm$^{-1}$

NMR (DMSO-d$_6$, δ): 1.34 (s) and 1.39 (s)(9H), 1.75–1.90 (1H, m), 2.20–2.40 (1H, m), 3.05–3.15 (1H, m), 3.40–3.55 (1H, m), 4.00–4.25 (2H, m)

Preparation 7

The object compound was obtained according to a similar manner to that of Preparation 6.

IR (Nujol): 1760, 1640 cm$^{-1}$

NMR (DMSO-d$_6$, δ): 1.46 (9H, s), 1.95–2.10 (1H, m), 2.40–2.60 (1H, m), 3.70–3.90 (2H, m), 4.44 (1H, dd, J=5 and 9Hz), 12.75 (1H, br s)

Preparation 8

The object compounds were obtained according to a similar manner to that of Preparation 3.

(1)

IR (Neat): 3300, 1690, 1635 cm$^{-1}$

NMR (DMSO-d$_6$, δ): 1.26 (s), 1.39 (s) and 1.40 s)(9H), 1.5–1.8 (1H, m), 2.2–2.4 (1H, m), 2.7–3.1 (5H, m), 3.1–3.3 (1H, m), 3.4–3.5 (1H, m), 4.1–4.2 (2H, m), 4.3–4.6 (2H, m), 4.9–5.1 (1H, m), 5.18 (1H, d, J=6Hz), 7.0–7.1 (2H, m), 7.1–7.3 (8H, m), 8.3–8.4 (1H, m)

(2)

IR (Neat): 1710, 1680, 1645 cm$^{-1}$

NMR (DMSO-d$_6$, δ): 1.31 (9H, s), 1.7–1.9 (1H, m), 2.2–2.4 (1H, m), 2.76 (s) and 2.86 (s)(3H), 2.8–3.1 (2H, m), 3.7–3.9 (2H, m), 4.4–4.6 (3H, m), 4.9–5.1 (1H, m), 7.0–7.4 (10H, m), 8.25–8.35 (1H, m)

(3)

IR (Neat): 3300, 1705, 1640, 1495 cm$^{-1}$

NMR (DMSO-d$_6$, δ): 1.31 (9H, s), 2.7–3.1 (6H, m), 3.2–3.4 (1H, m), 4.3–4.7 (5H, m), 4.9–5.1 (1H, m), 7.0–7.1 (3H, m), 7.1–7.3 (7H, m), 8.43 (1H, br t, J=8Hz)

Preparation 9

The object compound was obtained according to a similar manner to that of Preparation 1.

mp: 111°–113° C.

IR (Neat): 3300, 1680, 1640, 1525, 1415, 1265, 1170 cm$^{-1}$

NMR (DMSO-d$_6$, δ): 1.25 (s), 1.29 (s) and 1.36 (s)(9H), 2.60–2.90 (2H, m), 2.73 (s) and 2.83 (s)(3H), 4.20–4.70 (3H, m), 6.60 (d, J=8Hz) and 6.65 (d, J=8Hz)(2H), 6.89 (d, J=8Hz) and 7.05 (d, J=8Hz)(2H), 7.10–7.40 (5H, m), 9.22 (1H, s)

Elemental Analysis. Calculated for $C_{22}H_{28}N_2O_4$: C 68.73, H 7.34, N 7.29; Found: C 68.54, H 7.35, N 7.14

Preparation 10

The object compound was obtained according to similar manners to those of Preparation 2 and Preparation 3, successively.

IR (Nujol): 3280, 1665, 1630, 1515 cm$^{-1}$

NMR (DMSO-d$_6$, δ): 1.28 (s) and 1.39 (s)(3H), 1.60–1.90 (1H, m), 1.90–2.10 (1H, m), 2.60–3.00 (2H, m), 2.75 (s) and 2.82 (s)(3H), 3.20–3.30 (1H, m), 3.35–3.50 (1H, m), 4.10–4.70 (4H, m), 4.70–5.05 (2H, m), 6.60 (d, J=8Hz) and 6.64 (d, J=8Hz)(2H), 6.86 (d, J=8Hz) and 7.03 (d, J=8Hz)(2H), 6.90–7.10 (2H, m), 7.20–7.35 (3H, m), 8.20–8.40 (1H, m), 9.19 (s) and 9.23 (s)(1H)

Preparation 11

To a solution of Starting Compound (2.56 g) in methylene chloride (40 ml) was added trichloroacetyl isocyanate (1.0 g) under ice-cooling. After stirring for five minutes, the solution was washed with water, aqueous sodium hydrogencarbonate solution, and aqueous sodium chloride solution and dried over magnesium sulfate to give Object Compound (3.55 g).

IR (CH$_2$Cl$_2$): 3400, 1810, 1740, 1690, 1645, 1490, 1160 cm$^{-1}$

NMR (CDCl$_3$, δ): 1.47 (9H, s), 2.1–2.4 (2H, m), 2.65 and 2.87 (3H, s), 2.95–3.1 (2H, m), 3.5–4.0 (2H, m), 4.3–4.63 (3H, m), 5.1–5.4 (2H, m), 7.0–7.4 (11H, m), 8.63 (1H, s)

Preparation 12

To a solution of Starting Compound (3.10 g) in methanol (50 ml) was added 1N-sodium hydroxide solution (4.6 ml). The solution was stirred for two hours at room temperature. After concentration, the product was extracted with ethyl acetate and the organic layer was washed with water, sodium chloride solution and dried over magnesium sulfate, to give Object Compound (2.75 g).

IR (CH$_2$Cl$_2$): 3540, 3520, 1730, 1680, 1640, 1580 cm$^{-1}$

NMR (DMSO-d$_6$, δ): 1.25 and 1.39 (9H, s), 1.75–2.0 and 2.1–2.3 (2H, m), 2.78 and 2.85 (3H, s), 2.8–3.1 (2H, m), 3.35–3.7 (2H, m), 4.2 (1H, m), 4.35–4.8 (2H, m), 4.9–5.05 (2H, m), 6.32 (2H, br s), 7.0–7.3 (10H, m), 8.4–8.5 (1H, m)

Preparation 13

The object compound was obtained according to a similar manner to that of Preparation 4.

NMR (DMSO-d$_6$, δ): 1.9–2.1 (1H, m), 2.4–2.6 (1H, m), 2.76 and 2.83 (3H, s), 2.85–3.1 (2H, m), 3.15–3.2 and 3.37 (2H, m), 4.2–4.3 (1H, m), 4.45–4.65 (2H, m), 4.9–5.2 (2H, m), 6.73 (2H, s), 7.0–7.4 (12H, m), 9.25 (1H, d, J=7.6Hz)

Preparation 14

To a solution of Starting Compound (6.0 g) and cetyltrimethylammonium chloride (0.56 g) in methylene chloride (120 ml) were added powdered sodium hydroxide (2.5 g) and ethyl bromoacetate (1.66 ml) at room temperature. After stirring the solution overnight, powdered sodium hydroxide (0.5 g) and ethyl bromoacetate (0.69 ml) were added. The mixture was heated under reflux for further four hours. After evaporation of methylene chloride, ethyl acetate (200 ml) was added, and under ice-cooling, 1N-hydrochloric acid was added until the aqueous layer was neutralized to pH 4. The organic layer was washed with diluted sodium hydrogencarbonate solution, 0.5N hydrochloric acid, sodium chloride solution and dried with magnesium sulfate. After concentration, the residue was applied to a silica gel (95 g) column eluting first with methylene chloride then with a mixed solvent of methylene chloride and ethyl acetate (9:1 to 3:2) to give purified Object Compound (3.4 g) as an amorphous solid.

IR (CH$_2$Cl$_2$): 3400, 1745, 1680, 1640 cm$^{-1}$

NMR (CDCl$_3$, δ): 1.29 (3H, t, J=7Hz), 1.46 (9H, s), 1.9–2.4 (2H, m), 2.64 and 2.87 (3H, s), 2.95–3.1 (2H, m), 3.4–3.6 and 3.8 (2H, m), 4.0–4.65 (9H, m), 5.16 (1H, m), 6.8–7.4 (10H, m)

Preparation 15

The object compound was obtained according to a similar manner to that of Preparation 4.

NMR (DMSO-d$_6$, δ): 1.22 (3H, t, J=7Hz), 1.75–2.0 (1H, m), 2.5–2.6 (1H, m), 2.75 and 2.81 (3H, s), 2.9–3.1 (2H, m), 3.25–3.5 (2H, m), 4.14 (2H, q, J=7Hz), 4.20 (2H, s), 4.2–4.6 (4H, m), 4.9–5.05 (1H, m), 7.0–7.4 (10H, m), 8.68 (1H, br s), 9.20 (1H, d, J=7.7Hz), 10.38 (1H, br s)

Preparation 16

To a solution of Boc-Asp(OBzl)-OH (3.23 g) and NMM (1.01 g) in methylene chloride (30 ml) was added isobutyl chloroformate (1.37 g) dropwise at −20° C. The solution was stirred at the same temperature for twenty minutes. The solution was cooled to −35° C. and was added to a solution of Starting Compound (3.05 g) and NMM (1.01 g) in methylene chloride (20 ml). The mixture was stirred for an hour, raising the temperature gradually to 0° C., and further stirred under ice cooling for half an hour. After concentration, the product was extracted with ethyl acetate and the organic layer was washed with water, diluted sodium hydrogencarbonate solution, 0.5N hydrochloric acid, and sodium chloride solution, and dried over magnesium sulfate. After concentration and crystallization with a mixed solvent of diethyl ether and IPE under ice-cooling gave Object Compound (3.97 g).

mp: 56°–57° C.

IR (Nujol): 3300, 1736, 1690, 1660, 1640 (sh), 1630, 1515 cm$^{-1}$

NMR (CDCl$_3$, δ): 1.48 (9H, s), 2.58 (2H, s), 2.8–3.17 (5H, m), 4.2 (1H, m), 4.4–4.7 (2H, m), 5.17 (2H, s), 5.2 (1H, m), 5.58 (1H, d, J=8Hz), 7.1 (1H, m), 7.2–7.5 (15H, m)

Preparation 17

To a solution of Boc-Asp(OBzl)-OH (0.97 g), Starting Compound (0.914 g) and HOBT (0.405 g) in a mixed solvent of methylene chloride (25 ml) and DMF (5 ml) was added WSC (0.511 g) under ice-cooling. The solution was stirred at the same temperature for three hours. After concentration the product was extracted with ethyl acetate. The organic layer was washed successively with water, diluted sodium hydrogencarbonate solution, 0.5N hydrochloric acid, sodium chloride solution, and dried over magnesium sulfate. Concentration gave a crude product (1.72 g), which was purified on a silica gel column eluting with chloroform-ethyl acetate (4:1) to give Object Compound (1.68 g).

Preparation 18

A mixture of Starting Compound (1.0 g) and anisole (1.0 ml) was treated with TFA (15 ml) under ice-cooling for fifteen minutes and further at room temperature for twenty minutes. After concentration of the mixture, 4N-HCl/DOX (0.85 ml) was added and concentrated again. The residue was washed with n-hexane and IPE four times respectively and the powder was filtered, washed with IPE and dried under vacum to give Object Compound (0.87 g). The product was used in the next reaction without purification.

Preparation 19

To an ice-cooled solution of Starting Compound (2.81 g), HOBT (1.35 g) and N-(2-pyridylmethyl)-N-methylamine (1.22 g) in methylene chloride (28 ml) was added WSC.HCl (1.92 g). The solution was stirred at room temperature for four hours and washed successively with 5% sodium hydrogencarbonate solution, sodium chloride solution and was dried over magnesium sulfate. Evaporation and purification on a silica gel column (84 g) eluting with chloroform-methanol (20:1) gave Object Compound (3.14 g) as an oil.

IR (Neat): 3300, 1700, 1640, 1510, 1245, 1165, 650 cm$^{-1}$

NMR (DMSO-d$_6$, δ): 1.27 (s) and 1.35 (s)(9H), 2.6–3.0 (2H, m), 2.82 (s) and 2.96 (s)(3H), 4.4–4.9 (3H, m), 6.5–6.7 (2H, m), 6.8–7.4 (5H, m), 7.6–7.8 (1H, m), 8.48 (d, J=4Hz) and 8.53 (d, J=4Hz)(1H), 9.14 (s) and 9.22 (s)(1H)

Preparation 20

To an ice-cooled solution of Starting Compound (3.9 g) and anisole (3.9 ml) in methylene chloride (40 ml) was added TFA (25 ml). The solution was stirred for half an hour at room temperature. After evaporation, addition and re-evaporation of 4N-HCl/DOX (5 ml) were repeated twice. The residue was extracted with ethyl acetate and the organic layer was washed successively with saturated sodium hydrogencarbonate solution and brine, and dried over anhydrous magnesium sulfate to give the above Intermediate (3.03 g). To the solution in DMF (50 ml) containing Intermediate obtained was added Boc-Pro-OH (2.15 g), HOBT (1.35 g) and WSC.HCl (1.92 g). The solution was stirred for one and half an hour at room temperature. After evaporation and extraction with ethyl acetate. The organic layer was washed successively with water, 1N hydrochloric acid, water, 5% sodium hydrogencarbonate, water and saturated sodium chloride and dried over magnesium sulfate. The evaporated residue was subjected to column chromatography on silica gel (120 g) and eluted with a mixture of ethyl acetate and toluene (1:3). The fractions containing the object compound were combined and evaporated. The residue was collected by filtration, and dried to give Object Compound (4.34 g).

IR (Neat): 3300 1690 1640 cm$^{-1}$

NMR (DMSO-d$_6$, δ): 1.21 (s) and 1.36 (s)(9H), 1.4–1.8 (3H, m), 1.8–2.1 (1H, m), 2.5–3.1 (4H, m), 3.1–3.4 (2H, m), 3.4–3.7 (2H, m), 4.0–4.1 (1H, m), 4.4–4.8 (2H, m), 4.9–5.1 (1H, m), 7.0–7.3 (9H, m), 8.1–8.3 (1H, m)

Preparation 21

The object compounds were obtained according to a similar manner to that of Preparation 4 or 18.

(1)

IR (CHCl$_3$): 1735, 1685, 1675, 1655, 1640, 1625, 1560, 1545, 1490, 1450 cm$^{-1}$

NMR (DMSO-d$_6$, δ): 1.7–1.9 (1H, m), 2.2–2.4 (1H, m), 2.78 (s) and 2.88 (s)(3H), 2.9–3.2 (2H, m), 3.2–3.4 (1H, m), 3.5–3.7 (1H, m), 4.2–4.6 (4H, m), 4.8–5.1 (1H, m), 5.5–5.6 (1H, m), 6.9–7.2 (9H, m), 8.64 (br s) and 10.06 (br s)(1H), 9.18 (1H, d, J=8Hz)

(2)

IR (CHCl$_3$): 1760–1740, 1680, 1655, 1640, 1565, 1545, 1490, 1315 cm$^{-1}$

NMR (DMSO-d$_6$, δ): 1.6–1.9 (1H, m), 2.1–2.4 (1H, m), 2.81 (s) and 2.93 (s)(3H), 2.9–3.2 (2H, m), 3.2–3.5 (2H, m), 4.2–4.8 (4H, m), 5.08 (1H, q, J=7Hz), 5.57 (1H, br s), 6.9 (1H, d, J=7Hz), 7.0–7.8 (8H, m), 8.61 (br s) and 10.80 (br s)(1H), 9.1–9.3 (1H, m)

(3)

IR (CHCl$_3$): 1675, 1640, 1630, 1590, 1565, 1545, 1490 cm$^{-1}$

NMR (DMSO-d$_6$, δ): 1.7–1.9 (1H, m), 2.2–2.4 (1H, m), 2.76 (s) and 2.85 (s)(3H), 2.9–3.2 (3H, m), 3.2–3.4 (1H, m), 4.2–4.6 (4H, m), 4.9–5.1 (1H, m), 5.5–5.6 (1H, m), 6.9–7.4 (10H, m), 9.20 (1H, d, J=7Hz)

(4)

IR (Nujol): 3220, 3060, 2620, 1670, 1645, 1580, 1555, 1455 cm$^{-1}$

NMR (DMSO-d$_6$, δ): 1.6–2.0 (3H, m), 2.2–2.4 (1H, m), 2.76 (s) and 2.83 (s)(3H), 2.9–3.1 (2H, m), 3.1–3.3 (2H, m), 4.1–4.3 (1H, m), 4.3–4.7 (2H, m1, 4.9–5.1 (1H, m), 7.0–7.4 (10H, m), 8.3–8.7 (br s) and 9.9–10.3 (br s)(1H), 9.13 (1H, d, J=8Hz)

(5)

IR (CHCl$_3$): 3650–3300, 1655, 1640, 1585, 1490, 1455 cm$^{-1}$

NMR (DMSO$_6$, δ): 2.62 (s) and 2.70 (s)(3H), 2.9–3.3 (2H, m), 4.3–4.7 (3H, m), 7.1–7.4 (9H, m), 8.53 (2H, s)

(6)

IR (CHCl$_3$): 1655, 1605, 1580, 1510, 1495, 1455, 1365, 1315 cm$^{-1}$

NMR (DMSO$_6$, δ): 2.65 (s) and 2.70 (s)(3H), 2.9–3.1 (1H, m), 3.1–3.3 (1H, m), 3.5–3.9 (1H, m), 4.3–4.8 (2H, m), 7.49 (1H, d, J=7Hz), 7.2–7.7 (7H, m), 7.72 (1H, d, J=7Hz), 8.64 (2H, s)

(7)

mp: 94°–105° C.

IR (Nujol): 3450, 1650, 1630, 1590, 1470, 1275 cm$^{-1}$

NMR (DMSO$_6$, δ): 2.59 (s) and 2.67 (s)(3H), 2.9–3.1 (1H, m), 3.1–3.3 (1H, m), 4.3–4.7 (3H, m), 6.9–7.2 (9H, m), 8.53 (2H, s)

(8)

NMR (DMSO-d$_6$, δ): 2.74 (s) and 2.81 (s)(3H), 2.8–3.1 (2H, m), 3.6–3.9 (3H, m), 4.46 (2H, dd, J=15 and 20Hz), 4.9–5.1 (1H, m), 5.52 (1H, broad s), 7.0–7.4 (10H, m), 8.29 (3H, broad s), 9.0–9.1 (1H, m)

(9)

NMR (DMSO-d$_6$, δ): 1.7–1.9 (1H, m), 2.2–2.4 (1H, m), 2.7–3.5 (7H, m), 4.2–4.5 (2H, m), 4.6–5.0 (3H, m), 6.65 (d, J=8Hz) and 6.70 (d, J=8Hz)(2H), 6.96 (d, J=8Hz) and 7.07 (d, J=8Hz)(2H), 7.34 (1H, d, J=8Hz), 7.61 (t, J=8Hz), and 7.83 (t, J=8Hz)(1H), 8.06 (t, J=8Hz) and 8.35 (t, J=8Hz)(1H), 8.71 (d, J=4Hz) and 8.78 (d, J=4Hz)(1H)

(10)

NMR (DMSO-d$_6$, δ): 1.7–1.9 (1H, m), 2.2–2.4 (1H, m), 2.8–3.4 (7H, m), 4.2–4.5 (2H, m), 4.75 (1H, d, J=16Hz), 4.87 (1H, d, J=16Hz), 4.96 (1H, q, J=8Hz), 7.2–7.35 (6H, m), 7.40 (1H, d, J=8Hz), 7.62 (t, J=6Hz) and 7.83 (t, J=6Hz)(1H), 8.10 (t, J=8Hz) and 8.37 (t, J=8Hz)(1H), 8.61 (1H, broad), 8.70 (d, J=5Hz) and 8.78 (d, J=5Hz)(1H), 9.23 (1H, d, J=7Hz), 10.20 (1H, broad)

(11)

IR (CHCl$_3$): 1740, 1680, 1640, 1550, 1495 cm$^{-1}$

NMR (DMSO-d$_6$, δ): 1.7–1.9 (1H, m) 1.93 (s) and 1.95 (s)(3H), 2.2–2.4 (1H, m), 2.8–3.2 (3H, m), 3.2–3.6 (3H, m), 3.9–4.1 (2H, m), 4.2–5.1 (5H, m), 5.57 (1H, s), 7.0–7.4 (11H, m), 9.20 (1H, t J=8Hz)

Preparation 22

The object compounds were obtained according to a similar manner to that of Preparation 3 or 17.

(1)

mp: 112°–113° C.

IR (Nujol): 3370, 3310, 1700, 1690 (sh), 1660, 1645, 1630, 1538, 1525 (sh), 1285, 1260, 1175 cm$^{-1}$ NMR (CDCl$_3$, δ): 1.41 (9H, s), 1.2–1.8 (6H, m), 2.60 and 2.78 (3H, s), 2.85–3.2 (4H, m), 3.9–4.7 (3H, m), 4.9–5.35 (5H, m), 6.8–7.4 (16H, m)

Elemental Analysis. Calculated for $C_{36}H_{46}N_4O_6$: C 68.55, H 7.35, N 8.88; Found C 68.90, H 6.96, N 8.88

(2)

NMR (CDCl$_3$, δ): 1.3–1.9 (6H, m), 1.43 (9H, s), 2.65 and 2.83 (3H, s), 3.0–3.4 (4H, m), 3.9–4.3 (2H, m), 4.33 and 4.65 (ABq, 2H, J=14Hz), 5.0–5.4 (3H, m), 5.20 (2H, s), 6.9–7.5 (14H, m)

(3)

NMR (CDCl$_3$, δ): 1.45 (9H, s), 1.5–2.1 (4H, m), 2.66 and 2.79 (3H, s), 2.92–3.4 (4H, m), 4.0–4.3 (1H, m), 4.43 (2H, ABq, J=15Hz), 5.09 (2H, s), 4.9–5.3 (3H, m), 6.9–7.4 (15H, m)

Preparation 23

The object compounds were obtained according to a similar manner to that of Preparation 4 or 18.

(1)~(4)

The products were used in the next reaction without purification.

Preparation 24

The object compound was obtained according to a similar manner to that of Preparation 2 or 4.

IR (Nujol): 2700, 2450, 1640 cm$^{-1}$

NMR (DMSO-d$_6$, δ): 2.47 (3H, s), 2.51 (3H, s), 2.7–3.6 (2H, m), 4.40 (2H, s), 4.64 (1H, dd, J=6 and 9Hz), 6.9–7.4 (10H, m), 9.5 (2H, br s)

Preparation 25

The object compounds were obtained according to a similar manner to that of Preparation 19.

(1)

IR (Neat): 3320, 2990, 1720, 1705, 1690, 1655, 1640, 1580, 1490 cm$^{-1}$

NMR (DMSO-d$_6$, δ): 1.24 (s) and 1.35 (s)(9H), 2.74 (s) and 2.86 (s)(3H), 2.7–3.0 (2H, m), 4.30 (1H, d, J=15Hz), 4.5–4.7 (2H, m), 6.9–7.4 (10H, m)

(2)

IR (CHCl$_3$): 3300, 2950, 1705, 1645, 1490, 1365, 1315 cm$^{-1}$

NMR (DMSO-d$_6$, δ): 1.18 and 1.36 (s)(9H), 2.7–3.2 (2H, m), 2.91 (s) and 2.94 (s)(3H), 4.3–4.5 (1H, m), 4.6–4.9 (2H, m), 7.0–7.8 (10H, m)

(3)

IR (Neat): 3320, 2980, 1705, 1640, 1490, 1455, 1365 cm$^{-1}$

NMR (DMSO-d$_6$, δ): 1.23 (s) and 1.34 (s)(3H), 2.7–3.0 (5H, m), 4.4–4.7 (3H, m), 7.0–7.4 (11H, m)

(4)

IR (Neat): 3300, 1710, 1640, 1170 cm$^{-1}$

NMR (DMSO-d$_6$, δ): 1.24 (s) and 1.34 (s)(9H), 2.7–3.0 (2H, m), 2.84 (s) and 2.99 (s)(3H), 4.4–4.9 (3H, m), 6.9–7.3 (8H, m), 7.6–7.8 (1H, m), 8.49 (d, J=4Hz) and 8.54 (d, J=4Hz)(1H)

(5)

IR (Nujol): 3460, 3390, 1690, 1625, 1520 cm$^{-1}$

NMR (DMSO-d$_6$, δ): 1.25 (s) and 1.32 (s)(9H), 2.6–3.8 (6H, m), 4.2–4.9 (4H, m), 6.9–7.4 (11H, m)

Preparation 26

The object compound was obtained according to a similar manner to that of Preparation 1.

mp: 74°–75° C.

IR (Nujol): 1680, 1645 cm$^{-1}$

NMR (DMSO-d$_6$, δ): 0.94 (s), 1.12 (s) and 1.27 (s)(9H), 2.6–3.1 (2H, m), 2.71 (3H, s), 2.82 (3H, s), 4.2–4.7 (2H, m), 4.9–5.4 (1H, m), 6.9–7.4 (10H, m)

Preparation 27

The object compound was obtained according to a similar manner to that of Example 27.

NMR (DMSO-d$_6$, δ): 1.39 (9H, s), 2.5 (2H, m), 2.74 and 2.79 (3H, s), 2.8–3.0 (2H, m), 4.1–4.4 (1H, m), 4.46 (2H, s), 4.8–5.1 (1H, m), 7.0–7.4 (11H, m), 8.04 (1H, d, J=8Hz), 12.21 (1H, s)

Preparation 28

The object compound was obtained according to a similar manner to that of Preparation 6.

mp: 191°–193° C.

IR (Nujol): 3320, 1730, 1660 cm$^{-1}$

NMR (DMSO-d$_6$, δ): 1.2–1.4 (1H, m), 1.39 (9H, s), 1.5–1.7 (1H, m), 1.7–1.9 (1H, m), 1.9–2.2 (1H, m), 2.8–3.1 (1H, m), 3.7–3.8 (2H, m), 4.5–4.8 (2H, m), 12.7 (1H, broad)

Preparation 29

The object compounds were obtained according to a similar manner to that of Preparation 3 or 17.

(1)

IR (Neat): 3350 (broad), 1690–1630 cm$^{-1}$

NMR (DMSO-d$_6$, δ): 1.2–1.5 (2H, m), 1.33 (9H, s), 1.6–1.8 (1H, m), 1.8–2.1 (1H, m), 2.8–3.2 (6H, m), 3.6–3.8 (2H, m), 4.3–4.7 (4H, m), 4.9–5.1 (1H, m), 7.0–7.1 (2H, m), 7.1–7.4 (8H, m), 8.1–8.2 (1H, m)

(2)

mp: 115–116° C.

IR (Nujol): 1690, 1645 cm$^{-1}$

NMR (DMSO-d$_6$, δ): 1.29 (s), 1.30 (s), 1.38 (s) and 1.39 (s)(9H), 1.5–1.9 (3H, m), 2.0–2.3 (1H, m), 2.5–2.9 (1H, m), 2.72 (s) and 2.77 (s)(3H), 3.00 (3H, s), 3.2–3.5 (3H, m), 4.3–4.7 (3H, m), 5.4–5.7 (1H, m), 6.8–6.9 (1H, m), 7.0–7.1 (1H, m), 7.1–7.4 (8H, m)

Elemental Analysis. Calculated for C$_{38}$H$_{37}$N$_3$O$_4$: C 70.12, H 7.78, N 8.76; Found: C 69.93, H 7.81, N 8.70

(3)

IR (CHCl$_3$): 3350, 3000, 1700–1640, 1530, 1495, 1410, 1320 cm$^{-1}$

NMR (DMSO-d$_6$, δ): 1.21 (s), 1.25 (s), 1.33 (s) and 1.39 (s)(9H), 1.5–1.8 (1H, m), 1.8–2.1 (1H, m), 2.7–3.1 (5H, m), 3.1–3.3 (1H, m), 3.3–3.5 (1H, m), 4.0–4.3 (2H, m), 4.4–4.7 (2H, m), 4.9–5.2 (1H, m), 6.8–7.6 (8H, m), 7.7–7.8 (1H, m), 8.3–8.5 (1H, m)

(4)

IR (CHCl$_3$): 3430, 3320, 3000, 1690–1620, 1595, 1525, 1490 cm$^{-1}$

NMR (DMSO-d$_6$, δ): 1.25 (s) and 1.38 (s)(9H), 1.5–1.8 (1H, m), 1.8–2.1 (1H, m), 2.78 (s) and 2.87 (s)(3H), 2.7–3.1 (2H, m), 3.1–3.3 (1H, m), 3.3–3.5 (1H, m), 4.1–4.3 (2H, m), 4.3–4.6 (2H, m), 4.8–5.0 (2H, m), 6.8–7.0 (2H, m), 7.0–7.4 (7H, m), 8.3–8.4 (1H, m)

(5)

IR (CHCl$_3$): 3600–3250, 1695, 1680, 1645, 1490, 1455 cm$^{-1}$

NMR (DMSO-d$_6$, δ): 1.24 (s) and 1.38 (s)(9H), 1.5–1.8 (1H, m), 1.8–2.1 (1H, m), 2.7–3.1 (m) and 2.91 (s)(5H), 3.1–3.3 (1H, m), 3.3–3.5 (1H, m), 4.1–4.3 (2H, m), 4.3–4.6 (2H, m), 4.9–5.1 (2H, m), 6.9–7.4 (9H, m), 8.2–8.4 (1H, m)

(6)

IR (Neat): 3330, 3000, 2950, 1700, 1640, 1400 cm$^{-1}$

NMR (DMSO-d$_6$, δ): 1.25 (s) and 1.39 (s)(9H), 1.5–1.8 (1H, m), 2.0–2.3 (1H, m), 2.78 (s) and 2.85 (s)(3H), 2.8–3.1 (2H, m), 3.18 (s) and 3.19 (s)(3H), 3.4–3.5 (2H, m), 3.8–3.9 (1H, m), 4.0–4.2 (1H, m), 4.4–4.8 (2H, m), 4.8–5.1 (1H, m), 7.0–7.3 (10H, m), 8.37 (1H, d, J=8Hz)

(7)

IR (Neat): 3310, 1715, 1640, 1495 cm$^{-1}$

NMR (DMSO-d$_6$, δ): 1.06 (d, J=7Hz) and 1.11 (d, J=7Hz)(3H), 1.37 (9H, s), 2.72 (s) and 2.79 (s)(3H), 2.8–3.1 (2H, m), 3.8–4.1 (1H, m), 4.44 (s) and 2.47 (s)(2H), 4.8–5.1 (1H, m), 6.8–7.0 (1H, m), 7.0–7.4 (10H, m), 8.1–8.2 (1H, m)

(8)

IR (Neat): 3330, 1715, 1645, 1630, 1495 cm$^{-1}$

NMR DMSO-d$_6$, δ): 0.9–1.0 (3H, m), 1.39 (9H, s), 2.72 (s) and 2.79 (s)(3H), 2.8–3.1 (2H, m), 3.7–3.9 (2H, m), 4.3–4.6 (2H, m), 4.7–4.8 (1H, m), 4.9–5.1 (1H, m), 6.41 (1H, d, J=8Hz), 7.0–7.3 (10H, m), 8.1–8.3 (1H, m)

(9)

NMR (DMSO-d$_6$, δ): 1.38 (9H, s), 1.6-1.8 (2H, m), 2.3-2.4 (2H, m), 2.73 and 2.80 (3H, s), 2.8-3.1 (2H, m), 3.9-4.1 (1H, m), 4.3-4.5 (2H, m), 4.9-5.1 (1H, m), 6.9-7.35 (11H, m), 8.1-8.25 (1H, m)

(10)

IR (Neat): 1710, 1640, 1490, 1170 cm$^{-1}$

NMR (DMSO-d$_6$, δ): 1.30 (s) and 1.37 (s)(9H), 2.6-3.6 (10H, m), 4.3-4.7 (5H, m), 5.5-5.7 (1H, m), 6.7-7.4 (16H, m)

(11)

IR (Neat): 3320, 2980, 1720, 1640 cm$^{-1}$

NMR (DMSO-d$_6$, δ): 0.96 (s), 1.04 (s), 1.05 (s) and 1.08 (s)(9H), 2.6-3.5 (4H, m), 2.75 (s) and 2.77 (s)(3H), 3.02 (s) and 3.05 (s)(3H), 4.1-4.8 (3H, m), 5.03 (2H, s), 5.57 (1H, t, J=7Hz), 6.8-7.6 (16H, m)

Preparation 30

The object compounds were obtained according to a similar manner to that of Preparation 20.

(1)

IR (Neat): 1690-1630, 1510, 1405, 1160 cm$^{-1}$

NMR (DMSO-d$_6$, δ): 1.26 (s) and 1.39 (s)(9H), 1.5-2.1 (2H, m), 2.7-3.0 (5H, m), 3.2-3.5 (2H, m), 4.0-4.3 (2H, m), 4.3-5.1 (4H, m), 6.5-6.7 (2H, m), 6.7-7.4 (6H, m), 7.6-7.8 (1H, m), 8.1-8.3 (1H, m), 8.47 (d, J=4Hz) and 8.54 (d, J=4Hz)(1H), 9.14 (s) and 9.23 (s)(1H)

(2)

IR (Neat): 1690-1650, 1640, 1405, 1160 cm$^{-1}$

NMR (DMSO-d$_6$, δ): 1.24 (s) and 1.39 (s)(9H), 1.5-2.1 (2H, m), 2.8-3.2 (5H, m), 3.2-3.5 (2H, m), 4.0-4.3 (2H, m), 4.4-5.1 (4H, m), 6.8-7.4 (7H, m), 7.6-7.8 (1H, m), 8.2-8.4 (1H, m), 8.48 (d, J=5Hz) and 8.55 (d, J=5Hz)(1H)

(3)

IR (CHCl$_3$): 1740, 1705-1630, 1525 cm$^{-1}$

NMR (DMSO-d$_6$, δ): 1.22, 1.24 and 1.39 (9H, s), 1.5-2.1 (2H, m), 1.89 and 1.92 (3H, s), 2.8-3.1 (2H, m), 3.1-3.8 (4H, m), 3.8-4.0 (2H, m), 4.1-4.2 (2H, m), 4.4-5.1 (4H, m), 7.0-7.4 (10H, m), 8.3-8.5 (1H, m)

Preparation 31

The object compound was obtained according to a similar manner to that of Example 28.

mp: 172-175° C.

IR (Nujol): 3320, 3200, 1693, 1660 (sh), 1645, 1530 cm$^{-1}$

Preparation 32

The object compound was obtained according to a similar manner to that of Example 35.

IR (Neat): 3330, 2990, 1745, 1710, 1640, 1235, 1170 cm$^{-1}$

NMR (DMSO-d$_6$, δ): 1.27 (s) and 1.33 (s)(9H), 1.93 (3H, s), 2.6-3.1 (2H, m), 3.3-3.9 (2H, m), 3.9-4.2 (2H, m), 4.4-4.7 (3H, m), 7.0-7.4 (11H, m)

Preparation 33

The object compound was obtained according to a similar manner to that of Example 38.

IR (Neat): 3400, 2990, 1640, 1490 cm$^{-1}$

NMR (DMSO-d$_6$, +D$_2$O, δ): 0.97 (s), 1.05 (s), 1.08 (s) and 1.09 (s)(9H), 2.6-2.9 (1H, m), 2.77 (3H, br s), 2.98 (s) and 3.03 (s)(3H), 3.2-3.4 (3H, m), 3.7-3.9 (1H, m), 4.1-4.9 (2H, m), 5.5-5.8 (1H, m), 6.8-7.4 (10H, m)

Preparation 34

To an ice-cooled solution of Starting Compound (2.31 g) and methyl iodide (5 ml) in THF (30 ml) was added sodium hydride (60% in oil, 1.2 g) under atmosphere of nitrogen. The mixture was stirred for one and half an hour at the same temperature and for nine hours at room temperature. Ether and water were added to the reaction mixture and the aqueous layer was separated. After acidification with 6N hydrochloric acid, the aqueous layer was extracted with ethyl acetate twice. The extract was washed successively with water and sodium chloride solution and was dried over magnesium sulfate. Evaporation of the extract gave Object Compound (2.64 g) as an oil.

IR (Neat): 3000, 2950, 1740, 1700, 1400, 1160 cm$^{-1}$

NMR (DMSO-d$_6$, δ): 1.34 (s) and 1.39 (s)(9H), 1.9-2.0 (1H, m), 2.2-2.4 (1H, m), 3.21 (3H, s), 3.3-3.5 (2H, m), 3.9-4.1 (2H, m), 12.55 (1H, br)

EXAMPLE 1

Starting Compound (865 mg) was treated in TFA (15 ml) under ice-cooling for ten minutes and at room temperature for ten minutes. After concentration, the residue was dissolved in methylene chloride (30 ml), and under cooling, a solution of sodium hydrogencarbonate was added until aqueous layer was neutralized to pH 7. The organic layer was separated, washed with sodium chloride solution and dried over anhydrous magnesium sulfate to give the intermediate. After filtration, BSA (0.905 g) was added to the filtrate, and under ice-cooling, indole-3-carbonyl chloride (384 mg) was added. The solution was stirred for half an hour and concentrated. The residue was dissolved in a mixture of THF (15 ml) and 1N hydrochloric acid (5 ml), and the solution was stirred for half an hour. Ethyl acetate and water were added to the solution and the separated organic layer was washed with water, diluted sodium hydrogencarbonate solution, and sodium chloride solution, and dried over magnesium sulfate. After concentration, the residue was dissolved in chloroform and subjected to a silica gel column chromatography and eluted first with ethyl acetate and then with chloroform-methanol (4:1). The main fraction was concentrated and the residue was triturated with ether, filtered, and dried to give Object Compound (683 mg).

IR (Nujol) 3250, 1630, 1590 (sh), 1530 cm$^{-1}$

NMR (DMSO-d$_6$, δ): 1.7-2.1 (2H, m), 2.65-3.1 (7H, m), 3.65 (d, J=10Hz) and 3.9 (m)(2H), 4.2-4.6 (3H, m), 4.7 (1H, m), 4.9-5.05 (2H, m), 6.9-7.3 (12H, m), 7.45 (1H, d, J=7Hz), 7.85 (1H, br), 8.03 (1H, d, J=7Hz), 8.4 (1H, m), 11.64 (1H, s)

Elemental Analysis. Calculated for C$_{31}$H$_{32}$N$_4$O$_4$.½H$_2$O: C 69.78, H 6.23, N 10.50; Found: C 69.40, H 6.19, N 10.39

EXAMPLE 2

Starting Compound (1.02 g) was treated with TFA (15 ml) under ice-cooling for 15 minutes and at room temperature for 10 minutes. After concentration, the residue was dissolved in methylene chloride (50 ml), and under cooling, sodium hydrogencarbonate solution was added until the aqueous layer was neutralized to pH 7. The organic layer was separated, washed with sodium chloride solution, and dried over anhydrous magnesium sulfate. After filtration, indole-2-carboxylic acid (387 mg), HOBT (324 mg) was added, and under ice-cooling, WSC.HCl (458 mg) was added. The mixture was stirred at the same temperature for two hours and at room temperature overnight. The solution was concentrated and the product was extracted with ethyl acetate. The organic layer was washed successively with water diluted sodium hydrogencarbonate solution, 0.5N hydrochloric acid, and sodium chloride solution and dried over anhydrous magnesium sulfate. After concentration, the residue was applied to a silica gel column chromatography and eluted first with chloroform and then with chloroform-methanol (100:6). The main fraction was concentrated and the residue was triturated with diisopropyl ether, filtered, and dried to give Object Compound (840 mg).

IR (Nujol) 3250, 1630, 1595, 1525 cm$^{-1}$

NMR (DMSO-d$_6$, δ): 1.7–2.2 (2H, m), 2.72 and 2.79 (3H s) 2.8–3.2 (2H, m), 3.7–3.9 (1H, m), 4.0–4.2 (1H, m), 4.3–4.6 (3H, m), 4.6–4.8 (1H, m), 4.9–5.2 (2H, m), 6.9–7.3 (13H, m), 7.46 (1H, d, J=8Hz), 7.67 (1H, d, J=8Hz), 8.5–8.6 and 8.76 (1H, m), 11.47 and 11.57 (1H, s)

Elemental Analysis. Calculated for C$_{31}$H$_{32}$N$_4$O$_4$: C 70.97, H 6.15, N 10.68; Found: C 69.75, H 6.11, N 10.74

EXAMPLE 3

To an ice-cooled solution of Starting Compound (1.13 g) in methylene chloride (5 ml) was added TFA (13 ml). The solution was stirred at the same temperature for 15 minutes and at room temperature for another 15 minutes. The solution was concentrated and the residue was dissolved in methylene chloride (3 ml). Sodium hydrogencarbonate solution was added until the aqueous layer was neutralized to pH 7. The organic layer was separated, washed with sodium chloride solution, and dried over magnesium sulfate. After filtration, under ice-cooling, TEA (0.473 g) and trans-cinnamoyl chloride (391 mg) were added to the solution. After stirring for half an hour, the solution was concentrated and the product was extracted with ethyl acetate. The organic layer was washed successively with water, diluted sodium hydrogencarbonate solution, 0.5N hydrochloric acid, and sodium chloride solution, and dried over anhydrous magnesium sulfate. After concentration, the residue was applied to a silica gel column chromatography and eluted successively with methylene chloride, methylene chloride-acetate (10:1 to 3:1, gradient), and methylene chloride-acetone-methanol (70:30:2). The main fraction was pooled and concentrated, and the residue was triturated with ether, filtered, and dried to give Object Compound (0.737 g) as an amorphous solid.

IR (Nujol): 3250, 1640, 1595, 1080, 975 cm$^{-1}$

NMR (DMSO-d$_6$, δ): 1.7–2.2 (2H, m), 2.63–2.73 and 2.79 (3H, s), 2.8–3.1 (2H, m), 3.5–3.9 (2H, m), 4.2–4.8 (4H, m), 4.9–5.2 (2H, m), 6.70 (dd, J=15.4Hz and 4.5Hz) and 6.95–7.8 (m)(15H), 8.4–8.46 and 8.86–8.95 (1H, m)

EXAMPLE 4

To an ice-cooled solution of Starting Compound (1.0 g), 3-indoleacetic acid (0.419 g) and HOBT (0.323 g) in methylene chloride (30 ml), was added WSC (0.372 g). The solution was stirred at the same temperature for two hours. Then stirring was continued at room temperature for three hours, during which period, TEA (0.16 ml) and WSC.HCl (229 mg) were added to the solution. The solution was concentrated and the product was extracted with ethyl acetate. The organic layer was washed successively with water, diluted sodium hydrogencarbonate solution, 0.5N hydrochloric acid, and sodium chloride solution, and dried over anhydrous magnesium sulfate. After concentration, the residue was applied to a silica gel column chromatography and eluted first with chloroform and then with chloroform-methanol (100:2 to 100:7, gradient elution). The main fraction was concentrated and the residue was triturated with ether, filtered, and dried to give Object Compound (950 mg).

IR (Nujol): 3430 (sh), 3300, 1645 (sh), 1630 cm$^{-1}$

NMR (DMSO-d$_6$, δ): 1.75–2 0 and 2.0–2.2 (2H, m), 2.70–3.2 (5H, m), 3.3–3.45 (2H, m), 3.7 (2H, s), 4.1–4.3 (1H, m), 4.35–4.60 (3H, m), 4.9–5.1 (2H, m), 6.9–7.6 (15H, m), 8.3–8.4 and 8.8–8.9 (1H, m), 10.85 and 10.89 (1H, s)

EXAMPLE 5

To an ice-cooled solution of Starting Compound (0.90 g) in methylene chloride (20 ml) were added NMM (0.43 ml) and phenylacetyl chloride (0.26 ml). The solution was stirred at the same temperature for an hour and concentrated. The product was extracted with ethyl acetate and the organic layer was successively washed with water, 1N hydrochloric acid, 5% sodium hydrogencarbonate solution, and sodium chloride solution, and dried over anhydrous magnesium sulfate. Filtration and concentration gave Object Compound (0.76 g) as an amorphous solid.

IR (Nujol): 3290, 1630, 1490 cm$^{-1}$

NMR (DMSO-d$_6$, δ): 1.7–2.2 (2H, m), 2.7–3.4 (7H, m), 3.64 (2H, s), 4.1–4.6 (4H, m), 4.8–5.1 (2H, m), 7.0–7.4 (15H, m), 8.3–8.4 (m) and 8.8–8.9 (m)(1H)

EXAMPLE 6

The object compounds were obtained according to a similar manner to that of Example 1.

(1)
NMR (DMSO-d$_6$, δ): 1.75–1.85 (2H, m), 1.96–2.05 (2H, m), 2.43 and 2.80 (3H, s), 2.94–3.13 (2H, m), 3.45–3.50 (2H, m), 4.12 and 4.50 (2H, ABq, J=10Hz), 4.67–4.79 (1H, m), 5.06–5.17 (1H, m), 6.98–7.30 (14H, m), 7.52 (1H, m), 8.13 (1H, m), 10.21 (1H, m)

(2)
IR (Nujol): 3300–3150, 1650, 1630, 1590, 1530 cm$^{-1}$

NMR (DMSO-d$_6$, δ): 1.4–2.1 (4H, m), 2.75–3.1 (7H, m), 3.71 (2H, m), 4.3–4.7 (3H, m), 4.85–5.15 (1H, m), 7.0–7.3 (12H, m), 7.43 (1H, d, J=7.5Hz), 7.80 (1H, br), 8.06 (1H, d, J=7.4Hz), 8.4–8.6 (1H, m), 11.60 (1H, s)

Elemental Analysis. Calculated for C$_{31}$H$_{32}$N$_4$O$_3$: C 73.21, H 6.34, N 11.02; Found: C 73.03, H 6.26, N 11.00

(3)
IR (Nujol): 3250, 1630, 1540 cm$^{-1}$

NMR (DMSO-d$_6$, δ): 2.76 (s) and 2.83 (s)(3H), 2.8–3.1 (2H, m), 3.7–4.0 (2H, m), 4.3–4.8 (2H, m), 4.9–5.1 (1H, m), 7.0–7.3 (12H, m), 7.4–7.5 (1H, m), 8.0–8.2 (3H, m), 8.3–8.5 (1H, m), 11.57 (1H, s)

(4)
IR (Nujol): 3270, 1625, 1535 cm$^{-1}$

NMR (DMSO-d$_6$, δ): 2.72 (s) and 2.81 (s)(3H), 2.8–3.1 (2H, m), 3.6–3.7 (2H, m), 4.3–4.7 (3H, m), 4.92 (1H, t, J=6Hz), 5.03 (1H, q, J=8Hz), 7.0–7.3 (12H, m), 7.4–7.5 (1H, m), 7.7–7.80 (1H, m), 8.1–8.2 (2H, m), 8.3–8.4 (1H, m), 11.62 (1H, s)

(5)
IR (Nujol): 3290, 1665, 1630, 1535 cm$^{-1}$

NMR (DMSO-d$_6$, δ): 2.45–2.70 (2H, m), 2.73 (s) and 2.81 (s)(3H), 2.80–3.10 (2H, m), 4.30–4.60 (2H, m), 4.75–5.05 (2H, m), 6.93 (1H, s), 7.00–7.40 (13H, m), 7.40–7.50 (1H, m), 7.95–8.35 (4H, m), 11.63 (1H, s)

(6)
Nujol): 3270, 1630, 1535, 1495 cm$^{-1}$

NMR (DMSO-d$_6$, δ): 1.41 (s) and 1.45 (s)(6H), 2.70 (s) and 2.87 (s)(3H), 2.8–3.1 (2H, m), 4.3–4.7 (2H, m), 4.9–5.1 (1H, m), 7.0–7.4 (12H, m), 7.4–7.5 (1H, m), 7.7–7.9 (2H, m), 8.1–8.2 (2H, m), 11.60 (1H, s)

EXAMPLE 7

The object compounds were obtained according to a similar manner to that of Example 2.

(1)
IR (Nujol): 3250, 1640 (sh), 1630, 1595, 1525 cm$^{-1}$
NMR (DMSO$_6$, δ): 1.7–2.2 (2H, m), 2.71 and 2.79 (3H, s), 2.8–3.1 (2H, m), 3.7–4.1 (2H, m), 4.2–4.5 (3H, m), 4.6–4.7 (1H, m), 4.9–5.1 (2H, m), 6.7–7.3 (14H, m), 8.45–8.55 and 8.77 (1H, m), 8.82 (1H, m), 11.17 and 11.27 (1H, s)

(2)
IR (Nujol): 3300, 1645, 1600, 1530 cm$^{-1}$
NMR (DMSO-d$_6$, δ): 1.6–2.2 (4H, m), 2.74 and 2.81 (3H, s), 2.85–3.1 (2H, m), 3.6–4.0 (2H, m), 4.35–4.7 (3H, m), 4.9–5.05 (1H, m), 7.0–7.3 (13H, m), 7.46 (1H, d, J=8Hz), 7.66 (1H, d, J=8Hz), 8.48 (d, J=8Hz) and 8.71 (d, J=8Hz)(1H), 11.55 (1H, s)

EXAMPLE 8

The object compound was obtained according to a similar manner to that of Example 3.

NMR (DMSO-d$_6$, δ): 1.7–2.3 (4H, m), 2.8–3.1 (5H, m), 3.45–3.9 (2H, m), 4.35–4.75 (3H, m), 4.9–5.05 (1H, m), 6.68 (d, J=15.4Hz), 7.0–7.8 (m)(17H), 8.38 (d, J=8.3Hz), 8.7–8.8 (m)(1H)

EXAMPLE 9

The object compounds were obtained according to a similar manner to that of Example 4.

(1)
IR (Neat): 3300, 1630, 1495 cm$^{-1}$
NMR (DMSO-d$_6$, δ): 1.7–2.6 (4H, m), 2.6–3.1 (7H, m), 3.25–3.65 (2H, m), 4.1–4.6 (4H, m), 4.8–5.1 (2H, m), 7.0–7.3 (15H, m), 8.3–8.4 (m) and 8.7–8.8 (m)(1H)

(2)
IR (Neat): 3300, 1630, 1495 cm$^{-1}$
NMR (DMSO-d$_6$, δ): 1.6–2.5 (7H, m), 2.5–3.1 (6H, m), 3.2–3.6 (2H, m), 4.1–4.6 (4H, m), 4.9–5.1 (2H, m), 7.0–7.4 (15H, m), 8.3–8.4 (m) and 8.7–8.8 (m)(1H)

(3)
IR (Nujol): 3300, 1660 (sh), 1640, 1605 cm$^{-1}$
NMR (DMSO-d$_6$, δ): 1.65–2.2 (2H, m), 2.7–3.1 (5H, m), 3.2–3.5 (2H, m), 3.55–3.9 (2H, m), 4.2–4.6 (3H, m), 4.8–5.2 (2H, m), 5.4–5.55 (1H, m), 6.5–6.7 (3H, m), 7.0–7.4 (13H, m), 8.4 and 8.8 (1H, m)

(4)
IR (Nujol): 3250, 1625, 1210 cm$^{-1}$
NMR (DMSO-d$_6$, δ): 1.7–2.2 (2H, m), 2.7–3.15 (5H, m), 3.3–3.5 (2H, m), 3.55–3.75 (2H, m), 4.2 (1H, m), 4.35–4.6 (3H, m), 4.9–5.1 (2H, m), 6.60 (1H, dd, J=9Hz, 2Hz), 6.85 (1H, dd, J=9Hz, 2Hz), 7.0–7.4 (12H, m), 8.35–8.4 and 8.8–8.9 (1H, m), 8.55–8.6 (1H, m), 10.54 and 10.58 (1H, m)

(5)
IR (Nujol): 3260, 1630, 1590 cm$^{-1}$
NMR (DMSO-d$_6$, δ): 1.7–2.1 (2H, m), 2.72 (s) and 2.79 (s)(3H), 2.8–3.1 (2H, m), 3.6–4.0 (2H, m), 4.2–4.7 (4H, m), 4.8–5.1 (2H, m), 6.18 (1H, br s), 6.61 (1H, br s), 6.92 (1H, br s), 7.0–7.4 (10H, m), 8.4–8.5 (1H, m), 11.46 (1H, br s)

EXAMPLE 10

The object compounds were obtained according to a similar manner to that of Example 1.

(1)
mp: 234–236° C.
IR (Nujol): 3440, 3250, 1665, 1630, 1595 cm$^{-1}$
NMR (DMSO-d$_6$, δ): 1.65–1.85 (1H, m), 2.20–2.45 (1H, m), 2.67 (s) and 2.72 (s)(3H), 2.7–3.1 (2H, m), 3.55–3.70 (1H, m), 3.85–4.00 (1H, m), 4.15–4.30 (1H, m), 4.40 (2H, s), 4.55–4.70 (1H, m), 4.80–5.05 (1H, m), 5.28 (1H, br s), 6.90–7.00 (2H, m), 7.00–7.30 (10H, m), 7.44 (1H, d, J=7.5Hz), 7.86 (1H, s), 8.02 (1H, d, J=8Hz), 8.45 (1H, d, J=8Hz), 11.66 (1H, s)
Elemental Analysis. Calculated for C$_{31}$H$_{32}$N$_4$O$_4$: C 70.97, H 6.15, N 10.68; Found: C 70.88, H 6.08, N 10.60

(2)
IR (Nujol): 3180, 1640, 1590, 1570 cm$^{-1}$
NMR (DMSO-d$_6$, δ): 1.9–2.1 (1H, m), 2.3–2.5 (1H, m), 2.74 (s) and 2.84 (s)(3H), 2.8–3.1 (2H, m), 4.1–4.6 (4H, m), 4.8–5.1 (2H, m), 7.0–7.4 (12H, m), 7.4–7.5 (1H, m), 7.78 (1H, s), 8.15 (1H, d, J=8Hz), 8.5–8.7 (1H, m), 11.74 (1H, s)

(3)
IR (Nujol): 50, 1630, 1525 cm$^{-1}$
NMR (DMSO-d$_6$, δ): 2.74 (s) and 2.83 (s)(3H), 2.8–3.35 (4H, m), 4.4–4.7 (3H, m), 4.9–5.2 (3H, m), 7.0–7.3 (12H, m), 7.46 (1H, d, J=7Hz), 7.87 (1H, d, J=2Hz), 7.94 (1H, d, J=7Hz), 8.56 (d, J=8Hz) and 8.60 (d, J=8Hz)(1H), 11.79 (1H, s)

(4)
IR (Nujol): 3400, 1685, 1240 cm$^{-1}$
NMR (DMSO-d$_6$, δ): 1.7–2.2 (2H, m), 2.67 (s) and 2.75 (s)(3H), 2.6–3.0 (2H, m), 3.6–3.8 (1H, m), 3.8–4.1 (1H, m), 4.2–4.6 (3H, m), 4.6–5.0 (3H, m), 6.59 (d, J=8Hz), 6.62 (d, J=8Hz)(2H), 6.8–7.3 (9H, m), 7.44 (1H, d, J=7Hz), 7.85 (1H, s), 8.03 (1H, d, J=7Hz), 8.2–8.4 (1H, m), 9.20 (s) and 9.22 (s)(1H), 11.64 (1H, s)

EXAMPLE 11

The object compounds were obtained according to a similar manner to that of Example 4.

(1)
IR (Nujol): 3400, 3300, 1640 (sh), 1630, 1570 cm$^{-1}$
NMR (DMSO-d$_6$, δ): 1.7–2.4 (2H, m), 2.59, 2.64, 2.72 and 2.79 (3H, s), 2.8–3.1 (2H, m), 3.66, 3.8–3.9 and 3.95–4.1 (2H, m), 4.25–4.55 (3H, m), 4.6–4.8 (1H, m), 4.9–5.2 (2H, m), 6.8–7.8 (15H, m), 8.58 and 8.76 (2H, two sets of d, J=8Hz)
Elemental Analysis. Calculated for C$_{31}$H$_{31}$N$_3$O$_5$: C 70.84, H 5.94, N 7.99; Found: C 70.09, H 6.02, N 8.01

(2)
IR (Nujol): 3400, 3220, 1770, 1630, 1615, 1570 cm$^{-1}$
NMR (DMSO-d$_6$, δ): 1.75–2.3 (2H, m), 2.59, 2.72 and 2.79 (3H, s), 2.9–3.1 (2H, m), 3.73 and 4.10 (2H, br s), 4.20–4.55 (3H, m), 4.65–4.8 (1H, m), 4.95–5.1 and 5.3–5.4 (2H, m), 6.8–7.3 (11H, m), 7.4 (1H, m), 7.6 (1H, m), 8.17 (1H, d, J=8.1Hz), 8.45–8.6 (1H, m)
Elemental Analysis. Calculated for C$_{30}$H$_{33}$N$_5$O$_4$: C 68.29, H 6.30, N 13.27; Found: C 67.20, H 5.93, N 13.33

EXAMPLE 12

The object compounds were obtained according to a similar manner to that of Example 2.

(1)
IR (Nujol): 3200, 1670, 1640, 1605 cm$^{-1}$
NMR (DMSO-d$_6$, δ): 1.7–2.3 (2H, m), 2.46 (s), 2.57 (s), 2.70 (s) and 2.76 (s)(3H), 2.7–3.0 (2H, m), 3.6–4.5 (5H, m), 4.5–5.4 (3H, m), 6.5–6.7 (2H, m), 6.7–7.1 (4H, m), 7.1–7.3 (4H, m), 7.3–7.5 (1H, m), 7.5–7.7 (1H, m), 8.16 (1H, d, J=8Hz), 8.37 (d, J=8Hz) and 8.48 (d, J=8Hz)(1H), 9.21 (1H, br s), 13.3–13.7 (1H, broad)

(2)
IR (Nujol): 3250, 1630–1595, 1530, 1510 cm$^{-1}$
NMR (DMSO-d$_6$, δ): 1.7–2.1 (2H, m), 2.5–3.0 (2H, m), 2.70 (s) and 2.76 (s)(3H), 3.7–3.9 (1H, m), 3.9–4.1 (1H, m), 4.2–4.5 (3H, m), 4.5–5.0 (2H, m), 5.09 (1H d, J=2Hz), 6.5–7.1 (9H, m), 7.1–7.3 (4H, m), 8.42 (d, J=8Hz) and 8.72 (d, J=8Hz)(1H), 8.81 (1H, s), 9.22 (1H, s), 11.26 (1H, br s)

EXAMPLE 13

To a solution of Starting Compound (1.67 g) in methylene chloride (30 ml), 3-chloroperoxybenzoic acid (0.64 g) was added under ice-cooling. After stirring at the same temperature for 15 minutes, 5% sodium hydrogen carbonate solution was added. The mixture was filtered over celite. The organic layer was separated, dried over anhydrous magnesium sulfate and evaporated. The residue was applied to a silica gel column and eluted with a mixture of chloroform and methanol (20:1). The fractions containing the more polar product were collected and evaporated. The residue was pulverized with IPE, filtered and dried to give A-isomer of Object Compound (0.48 g).

IR (Nujol): 3250, 1640, 1525, 1040 $cm^{-1}$

NMR (DMSO-$d_6$, δ): 2.69 (s) and 2.77 (s)(3H), 2.8-3.1 (3H, m), 3.45-3.65 (1H, m), 4.3-4.6 (3H, m), 4.9-5.1 (1H, m), 5.3-5.4 (1H, m), 5.4-5.6 (1H, m), 7.0-7.1 (2H, m), 7.1-7.3 (10H, m), 7.47 (1H, d, J=7Hz), 7.9-8.0 (2H, m), 8.55-8.65 (1H, m), 11.86 (1H, s)

The fractions containing the less polar product were collected and evaporated. The residue was crystallized with IPE, filtered and dried to give B-isomer of Object Compound (0.40 g).

IR (Nujol): 3500, 3300, 1640, 1610, 1530, 1040 $cm^{-1}$

NMR (DMSO-$d_6$, δ): 2.72 (s) and 2.78 (s)(3H), 2.75-3.15 (3H, m), 3.25-3.50 (1H, m), 4.3-4.7 (3H, m), 4.9-5.1 (1H, m), 5.1-5.3 (1H, m), 5.40-5.55 (1H, m), 6.95-7.35 (12H, m), 7.49 (1H, d, J=7Hz), 7.85-7.95 (2H, m), 8.7-8.8 (1H, m), 11.82 (1H, s)

EXAMPLE 14

To a solution of Starting Compound (0.5 g) in methylene chloride (10 ml), 3-chloroperoxybenzoic acid (0.4 g) was added. After stirring at room temperature for 40 minutes, 3-chloroperoxybenzoic acid (0.2 g) was added and the mixture was warmed at 38° C. for half an hour. After adding 5% sodium hydrogencarbonate solution, the mixture was filtered over Celite. The organic layer was separated, washed with brine, dried over anhydrous magnesium sulfate and evaporated. The residue was applied to a silica gel column and eluted with a mixture of chloroform and methanol (30:1). The main fractions were collected and evaporated. The residue was pulverized with IPE, filtered and dried to give Object Compound (0.26 g).

IR (Nujol): 3280, 1630, 1525 $cm^{-1}$

NMR (DMSO$_6$, δ): 2.74 (s) and 2.80 (s)(3H), 2.8-3.3 (3H, m), 3.6-3.8 (1H, m), 4.4-4.5 (2H, m), 4.6-4.8 (1H, m), 4.9-5.1 (1H, m), 5.2-5.3 (1H, m), 5.4-5.5 (1H, m), 7.0-7.3 (12H, m), 7.48 (1H, d, J=7.5Hz), 7.9-8.0 (2H, m), 8.7-8.8 (1H, m), 11.94 (1H, s)

EXAMPLE 15

To a mixture of Starting Compound (5.0 g), cetyltrimethylammonium chloride (313 mg), and powdered sodium hydroxide (1.52 g) in methylene chloride (100 ml) was added tert-butyl bromoacetate (1.88 g) under ice cooling. The mixture was stirred at the same temperature for an hour. To the mixture was added 1N-hydrochloric acid (25 ml) and methylene chlorode was evaporated. Ethyl acetate and water were added to the residue and the mixture was acidified to pH 3 with 1N hydrochloric acid and was separated. The aqueous layer was extracted with ethyl acetate again and the combined organic layer was washed successively with water, diluted sodium hydrogencarbonate solution, sodium chloride solution and dried with magnesium sulfate. After concentration, the residue was chromatographed on a silica gel column (120 g) eluting with chloroform-methanol (methanol 1.5% to 2.5% gradient).

The fractions containing the more polar product were collected and evaporated to give Object Compound A (0.93 g).

IR (CH$_2$Cl$_2$): 1740, 1640 $cm^{-1}$

NMR (DMSO-$d_6$, δ): 1.39 (9H, s), 1.43 (9H, s), 1.8-2.0 (1H, m), 2.1-2.3 (1H, m), 2.71 and 2.78 (3H, s), 2.8-3.1 (2H, m), 3.8-4.0 (2H, m), 3.97 (2H, s), 4.18 (1H, m), 4.42 (2H, s), 4.68 (1H, t, J=7.5Hz), 4.9-5.1 (2H, m), 5.1 (2H, s), 7.0-7.3 (11H, m), 7.42 (1H, d, J=7.7Hz), 7.93 (1H, br s), 8.06 (1H, d, J=7.4Hz), 8.46 (1H, m)

The fractions containing the less polar product were collected and evaporated to give Object Compound B (4.46 g).

IR (CH$_2$Cl$_2$): 3600, 3400, 1740, 1670, 1640 $cm^{-1}$

NMR (DMSO-$d_6$, δ): 1.43 (9H, s), 1.75 -2.1 (2H, m), 2.70 and 2.78 (3H, s), 2.8-3.1 (2H, m), 3.6-3.7 and 3.8-4.0 (2H, m), 4.2-4.5 (3H, m), 4.65-4.8 (1H, m), 4.9-5.1 (2H, m), 5.1 (2H, s), 7.0-7.5 (13H, m), 7.9 (1H, br s), 8.1 (1H, d, J=8Hz), 8.44 (1H, m)

EXAMPLE 16

A solution of Starting Compound (3.56 g) and anisole (3.0 ml) in methylene chloride (25 ml) was treated with trifluoroacetic acid (16 ml) at room temperature for an hour. After concentration, the residue was dissolved in ethyl acetate and neutralized to pH 8 with sodium hydrogencarbonate solution. The aqueous layer was acidified with 4N-hydrochloric acid to pH 3 and extracted three times with ethyl acetate. The combined organic layer was washed with sodium chloride solution and dried over magnesium sulfate. After concentration, the residue was triturated in a mixed solvent of ethyl acetate and IPE and the resulting powder was filtered, washed with diisopropyl ether and dried to give Object Compound (3.04 g).

IR (Nujol): 3300, 1730, 1620, 1530 $cm^{-1}$

NMR (DMSO-$d_6$, δ): 1.75-2.1 (2H, m), 2.70 and 2.78 (3H, s), 2.8-3.2 (2H, m), 3.6-3.7 and 3.8-4.0 (2H, m), 4.31 (1H, br), 4.42 (2H, s), 4.8-5.1 (2H, m), 5.12 (2H, s), 7.0-7.3 (12H, m), 7.45 (1H, d, J=7.7Hz), 7.93 (1H, s), 8.07 (1H, d, J=7Hz), 8.44 (1H, m)

EXAMPLE 17

To a solution of Starting Compound (900 mg) and HOBT (209 mg) in methylene chloride (20 ml) was added WSC.HCl (295 mg) under ice-cooling. After stirring at the same temperature for twenty minutes, N,N-dimethylethylenediamine (133 mg), and the solution was stirred overnight under cooling. After concentration, the residue was extracted with ethyl acetate (100 ml) with sodium hydrogencarbonate solution. The organic layer was washed with sodium chloride solution and dried over magnesium sulfate. After concentration, the residue was dissolved in THF (12 ml) and 4N-HCl/DOX (0.31 ml) was added. The mixture was stirred for half an hour and concentrated. The residue was triturated with diethyl ether, filtered, washed with diethyl ether, and dried to give Object Compound (0.87 g).

IR (Nujol): 3250, 2700, 1680 (sh), 1640, 1530 $cm^{-1}$

NMR (DMSO-$d_6$, δ): 1.7-2.1 (2H, m), 2.7-2.8 (9H, m), 2.8-3.1 (2H, m), 3.2 (2H, m), 3.45 (2H, m), 3.6-3.7 and 3.8-4.0 (2H, m), 4.3-4.5 (3H, m), 4.7 (1H, m), 4.9-5.1 (2H, m), 5.04 (2H, s), 6.95-7.3 (12H, m), 7.51 (1H, d, J=7.7Hz), 7.98 (1H, s), 8.06 (1H, d, J=7.4Hz), 8.47 (1H, m), 8.68 (1H, m), 10.58 (1H, br s)

EXAMPLE 18

The object compound was obtained according to a similar manner to that of Example 15.

NMR (DMSO-d$_6$, $\delta$): 1.75-2.2 (2H, m), 2.20 (6H, s), 2.6-2.8 (5H, m), 3.4 (2H, m), 3.6-3.7 (1H, m) 3.9 (1H, br), 4.2-4.4 (5H, m), 4.71 (1H, m), 4.9-5.05 (2H, m), 7.0-7.3 (12H, m), 7.54 (1H, d, J=8Hz), 7.91 (1H, s), 8.0-8.05 (1H, m), 8.46 (1H, m)

EXAMPLE 19

To a solution of Starting Compound (1.39 g) in methylene chloride (14 ml) was added TEA (0.74 ml) under ice-cooling. To this solution was added a solution of MsCl (0.21 ml) in methylene chloride (1 ml) maintaining the temperature blow 6° C. After stirring for one hour. TEA (0.74 ml) was added and a solution of MsCl (0.21 ml) in methylene chloride (1 ml) was added dropwise. The mixture was stirred for additional half an hour and washed with water. The organic layer was dried over magnesium sulfate, and evaporated. The residue was subjected to a silica gel column chlomatography (60 g) and eluted with a mixture of chloroform and methanol (50:1-30:1). The main fractions were evaporated to give Object Compound (1.57 g).

IR (Nujol): 3250, 1630, 1525, 1170 cm$^{-1}$

NMR (DMSO-d$_6$, $\delta$): 1.9-2.1 (1H, m), 2.3-2.5 (1H, m), 2.69 (s) and 2.76 (s)(3H), 2.8-3.1 (2H, m), 3.22 3H, s), 4.0-4.3 (2H, m), 4.41 (2H, br s), 4.7-5.0 (2H, m), 5.33 (1H, br s), 6.9-7.3 (12H, m), 7.45 (1H, d, J=7Hz), 7.87 (1H, br s), 8.00 (1H, d, J=8Hz), 8.5-8.6 (1H, m), 11.72 (1H, s)

EXAMPLE 20

To a solution of Starting Compound (1.8 g) in DMSO (9 ml), sodium azide (0.39 g) was added. The solution was heated at 70° C. for 13.5 hours. After cooling, ethyl acetate (50 ml) was added and the solution was washed with water (three times) and brine. The organic layer was dried over magnesium sulfate and concentrated to give the concentrate of Intermediate Compound (ca. 20 ml). To the solution was added triphenylphosphine (0.78 g), then heated at 50° C. for 2 hours. After adding water (0.16 ml), the mixture was heated at 65° C. for 4.5 hours. The precipitates were filtered, subjected to a silica gel columnchromatography (10 g) and eluted with chloroform-methanol (4:1). The main fractions were evaporated to give Object Compound (0.95 g).

IR (Nujol): 3300, 1640, 1605 cm$^{-1}$

NMR (DMSO-d$_6$, $\delta$): 1.5-1.7 (1H, m), 1.78 (2H, br s), 2.2-2.4 (1H, m), 2.66 (s) and 2.73 (s)(3H), 2.7-3.1 (2H, m), 3.3-3.5 (2H, m), 3.8-4.0 (1H, m), 4.3-4.7 (3H, m), 4.8-5.1 (1H, m), 6.9-7.3 (11H, m), 7.43 (1H, d, J=8Hz), 7.5-7.7 (1H, m), 7.81 (1H, s), 8.00 (1H, d, J=8Hz), 8.4-8.7 (1H, m), 11.63 (1H, s)

EXAMPLE 21

In ethanol, Starting Compound (0.30 g) was dissolved under heating. After ice-cooling, 4N-HCl/DOx (0.16 ml) was added and the solution was evaporated. The residue was pulverized with ether, filtered and dried to give Object Compound (0.31 g).

IR (Nujol): 3200, 1625, 1520 cm$^{-1}$

NMR (DMSO-d$_6$, $\delta$): 1.8-2.2 (1H, m), 2.50 (1H, br s), 2.72 (3H, s), 2.7-3.2 (2H, m), 3.7-4.3 (3H, m), 4.3-4.6 (2H, m), 4.6-5.1 (2H, m), 6.9-7.6 (13H, m), 7.8-8.1 (2H, m), 8.4 (3H, br s), 8.85-9.15 (1H, m), 11.82 (1H, m)

EXAMPLE 22

To a solution of Starting Compound (1.5 g) and pyridine (0.23 ml) in mixed solvent of methylene chloride (30 ml) and DMF (20 ml) was added dropwise a solution of ehtyloxalyl chloride (0.32 ml) in methylene chloride (3 ml) under ice-cooling. The solution was stirred for four hours at the same temperature, during which period ethyloxalyl chloride (64 $\mu$l) and pyridine (46 $\mu$l) were added. After concentration, the product was extracted with ethyl acetate and the organic layer was washed successively with 1N hydrochloric acid, water, 5% sodium hydrogencarbonate solution, water, and sodium chloride solution and dried over magnesium sulfate. After concentration, the residue was applied to a column of silica gel (60 g) eluting with a mixed solvent of chloroform and methanol (50:1) to give Object Compound (1.75 g) as an amorphous solid.

IR (Nujol): 3260, 1750, 1690, 1640, 1525 cm$^{-1}$

NMR (DMSO$_6$, $\delta$): 1.22 (3H, t, J=7Hz), 1.7-2.0 (1H, m), 2.3-2.6 (1H, m), 2.69 (s) and 2.76 (s)(3H), 2.7-3.0 (1H, m), 3.0-3.2 (1H, m), 3.6-3.8 (1H, m), 4.0-4.6 (4H, m), 4.18 (2H, q, J=7Hz), 4.6-4.8 (1H, m), 4.8-5.1 (1H, m), 6.9-7.3 (12H, m), 7.45 (1H, d, J=7Hz), 7.85 (1H, s), 8.05 (1H, d, J=8Hz), 8.6-8.8 (1H, m), 9.1-9.3 (1H, m), 11.69 (1H, s)

EXAMPLE 23

The object compound was obtained according to a similar manner to that of Example 4.

mp: 125-130° C.

IR (Nujol): 3490, 3320, 3160, 1720, 1695, 1605 cm$^{-1}$

NMR (DMSO-d$_6$, $\delta$): 1.9-2.4 (2H, m), 2.60, 2.72 and 2.78 ( s), 2.9-3.1 (2H, m), 3.75-3.9 (1H, m), 4.17-4.26 (1H, m), 4.3-4.5 (2H, m), 4.7-4.8 (1H, m), 4.9-5.2 and 5.4 (2H, m), 6.60 (2H, br), 6.8-7.7 (13H, m), 8.17 (1H, d, J=8Hz), 8.5-8.7 (1H, m), 13.6 (1H, br)

EXAMPLE 24

The object compound was obtained according to a similar manner to that of Example 21.

IR (Nujol): 3250, 2650, 1630, 1530 cm$^{-1}$

NMR (DMSO-d$_6$, $\delta$): 1.75-2.1 (2H, m), 2.7-3.1 (11H, m), 3.5 (2H, m), 3.6-3.7 and 3.8-4.0 (2H, m), 4.3-4.5 (3H, m), 4.65-5.0 (5H, m), 7.0-7.3 (12H, m), 7.73 (1H, d, J=7.9Hz), 8.0-8.15 (2H, m), 8.47 (1H, m), 11.28 (1H, br s)

EXAMPLE 25

The object compounds were obtained according to a similar manner to that of the latter half of Example 1.

(1)

NMR (DMSO-d$_6$, $\delta$): 1.85-2.05 (1H, m), 2.15-2 35 (1H, m), 2.7 and 2.77 (3H, s), 2.8-3.1 (2H, m), 3.83 (1H, d, J=11.4Hz), 4.1 (1H, m), 4.42 (2H, s), 4.60-4.8 (1H, m), 4.9-5.1 (2H, m), 6.6 (2H, br), 7.0-7.3 (11H, m), 7.45 (1H, d, J=3.7Hz), 7.87 (1H, br s), 8.03 (1H, d, J=7.1Hz), 8.5 (1H, m), 11.7 (1H, s)

(2)

IR (Nujol) 3250, 1750, 1630, 1530 cm$^{-1}$

NMR (DMSO-d$_6$, $\delta$): 1.16 (3H, t, J=7Hz), 1.8-1.9 (1H, m), 2.15-2.3 (1H, m), 2.69 and 2.77 (3H, s), 2.8-3.1 (2H, m), 3.8-4.2 (7H, m), 4.41 (2H, br s), 4.68 (1H, m), 4.96 (1H, m), 6.95-7.3 (11H, m), 7.49 (1H, d, J=8.2Hz), 7.87 (1H, br s), 8.03 (1H, d, J=7.2Hz), 8.44 (1H, m), 11.67 (1H, br s)

EXAMPLE 26

The object compound was obtained according to a similar manner to that of the latter half of Example 1.

IR (Nujol) 3200-3400, 2600, 1660-1600, 1550-1530 cm$^{-1}$

NMR (DMSO-d$_6$, δ): 1.7-2.2 (2H, m), 2.7-3.1 (5H, m), 3.56-3.9 (2H, m), 4.3-4.6 (4H, m), 4.9-5.1 (2H, m), 7.0-7.3 (11H, m), 7.4-7.65 (1H, m), 7.9-8.1 (1H, m), 8.50 and 8.66 (1H, d, J=8Hz), 8.8-8.9 (1H, m), 9.0-9.3 (1H, m)

EXAMPLE 27

A solution of Starting Compound (703 mg) in a mixed solvent of ethanol (20 ml) and THF (5 ml) was hydrogenated under atmospheric pressure in the presence of 10% palladium on carbon (200 mg) at room temperature for two hours. Filtration and concentration gave Object Compound (500 mg) as an amorphous solid.

IR (Nujol): 3250, 1710, 1630, 1540 cm$^{-1}$

NMR (DMSO-d$_6$, δ): 2.72 and 2.79 (3H, s), 2.4-3.0 (4H, m), 4.43 (2H, m), 4.7-5.2 (2H, m), 6.9-7.3 (13H, m), 7.55 (1H, d, J=8Hz), 7.63 (1H, d, J=8Hz), 8.2 (1H, m), 8.6 (1H, m), 12.71 (1H, s)

EXAMPLE 28

To an ice-cooled solution of Starting Compound (2.54 g), HCl.H-Gln-NHBu$^t$ (1.52 g), and HOBT (0.648 g) in DMF (40 ml), was added WSC (0.783 g). After stirring at the same temperature for two hours and at room temperature for half an hour, NMM (0.18 ml) was added and the solution was stirred overnight. The solution was concentrated and the residue was triturated with water under cooling. Filtration and recrystallization of the precipitates gave Object Compound (1.42 g).

mp: 205-206° C.

IR (Nujol): 3300, 1660 (sh), 1642, 1630, 1545, 1535 cm$^{-1}$

NMR (DMSO$_6$, δ): 1.24 (9H, s), 1.6-2.2 (4H, m), 2.5-3.1 (4H, m), 2.71 and 2.78 (3H, s), 4.0-4.6 (3H, m), 4.7-5.1 (2H, m), 6.9-7 3 (13H, m), 7.38 (2H, s), 7.44 (1H, d, J=8Hz), 7.62 (1H, d, J=8Hz), 7.9 (1H, m), 8.2 (1H, m), 8.5 (1H, m), 11.54 (1H, s)

Elemental Analysis Calculated for $C_{39}H_{47}N_7O_6 \cdot H_2O$: C 64.40, H 6.79, N 13.47; Found: C 64.81, H 6.50, N 13.62

EXAMPLE 29

To an ice-cooled solution of Starting Compound (3.02 g) and BSA (2.27 g) in methylene chloride (50 ml) was added indole-3-carbonyl chloride (1.0 g). The solution was stirred at this temperature for two hours and BSA (0.82 g) and indole-3-carbonyl chloride (0.2 g) was added. The solution was washed with water, diluted sodium hydrogencarbonate solution 0.5N hydrochloric acid and sodium chloride solution and dried over magnesium sulfate. After concentration, the residue was applied to a silica gel (50 g) column and eluted firstly with chloroform and secondly with chloroform-methanol (100:1 to 100:2.5 gradient elution) to give Object Compound (3.3 g) as an amorphous solid.

IR (Nujol): 3270, 1740, 1635 (sh), 1620, 1550, 1540 cm$^{-1}$

NMR (DMSO-d$_6$, δ) : 2.64 and 2.81 (3H, s), 2.6-3.3 (4H, m), 4.27 and 4.67 (2H, ABq, J=15Hz), 5.0-5.3 (2H, m), 5.13 (2H, s), 7.03 (5H, s), 7.0-7.7 (13H, m), 7.8-8.1 (2H, m), 9.67 (1H, s)

EXAMPLE 30

To a solution of Starting Compound (2.87 g) in ethanol (60 ml) was added 10% palladium on carbon (780 mg). The solution was hydrogenated at room temperature for two hours under atmospheric pressure. After filtration, 4N-HCl/DOX (1.1 ml) was added to the filtrate and the solution was concentrated. Water (100 ml) and ethyl acetate (50 ml) were added to the residue and the aqueous layer was lyophilized to give Object Compound (2.09 g) as an amorphous solid.

IR (Nujol) : 3400-3100, 2750-2600, 1630, 1535 cm$^{-1}$

NMR (DMSO-d$_6$, δ) : 1.2-1.9 (6H, m), 2.70 and 2.77 (3H, s), 2.6-3.1 (4H, m), 4.2-4.6 (3H, m), 4.9-5.2 (1H, m), 6.9-7.5 (14H, m), 7.8-8.4 (6H, m)

Elemental Analysis. Calculated for $C_{32}H_{37}N_5O_3 \cdot HCl$: C 66.71, H 6.65, N 12.16, Cl 6.15; Found : C 62.22, H 6.33, N 11.63, Cl 7.51.

EXAMPLE 31

To an ice-cooled solution of Starting Compound (1.0 g), 3-diethylaminopropionic acid hydrochloride (318 mg), and HOBT (283 mg) was added WSC (271 mg). The solution was stirred at the same temperature for an hour and at room temperature for six hours. During these reaction period, NMM (0.1 ml) and WSC.HCl (33 mg) were added. The solution was concentrated and was acidified with diluted hydrochloric acid to pH 2 and washed twice with ethyl acetate. The aqueous layer was neutralized to pH 8 with sodium hydrogencarbonate solution and extracted twice with ethyl acetate. The organic layer was dried with magnesium sulfate and concentrated. The residue was dissolved in THF (15 ml) and 4N-HCl/DOX (0.35 ml) was added. After evaporation of THF, the residue was dissolved in water and washed with diethyl ether. The aqueous layer was lyophilized to give Object Compound (803 mg).

IR (Nujol) : 3200, 1630, 1535 cm$^{-1}$

NMR (DMSO-d$_6$, δ) : 1.17 (9H, s), 1.2-1.9 (6H, m), 2.5-2.7 (2H, m), 2.73 and 2.8 (3H, s), 2.9-3.4 (10H, m), 4.4-4.7 (3H, m), 4.8-5.1 (1H, m), 7.0-7.3 (12H, m), 7.4 (1H, m), 8.1-8.4 (3H, m), 10.3 (1H, br), 11.7 (1H, s)

EXAMPLE 32

Starting Compound (0.82 g) and anisole (1.0 ml) was dissolved in methylene chloride (5 ml), and under ice-cooling, TFA (15 ml) was added to the solution. The solution was stirred at the same temperature for twelve minutes and at room temperature for twenty minutes. After evaporation of TFA, 4N-HCl/DOX (0.6 ml) was added to the residue. The mixture was concentrated again and the residue was triturated with IPE. The powder was filtered, washed with ether, and dried under vacuum to give the intermediate (0.66 g). This intermediate was dissolved in methylene chloride (10 ml), and TEA (197 mg) and AC$_2$O (99 mg) were added into the solution at −15° C. After stirring the solution for half an hour, DMF (15 ml) and methanol (2 ml) was added to the solution to dissolve the precipitates and the solution was concentrated. The product was extracted with ethyl acetate and the organic layer was washed successively with water, diluted sodium hydrogencarbonate solution, 0.5N hydrochloric acid, and sodium chloride solution, and was dried over magnesium sulfate. After filtration, the precipitates formed after left standing were collected, washed with ethyl acetate, and dried to give Object Compound (0.36 g).

mp : 198°-201° C.

IR (Nujol) : 3250, 1660 (sh), 1635, 1620, 1550, 1250, 1215 cm$^{-1}$

NMR (DMSO-d$_6$, δ) : 1.0 (3H, d, J=6Hz), 1.2–1.8 (6H, m), 1.88 (3H, s), 2.70 and 2.77 (3H, s), 2.8–3.2 (4H, m), 3.8–4.2 (2H, m), 4.35–4.6 (3H, m), 4.70 (1H, d, J=5Hz), 4.85–5.2 (1H, m), 6.9–7.3 (11H, m), 7.3–7.75 (5H, m), 8.0–8.35 (3H, m), 11.5 (1H, br)

Elemental Analysis. Calculated for C$_{38}$H$_{46}$N$_6$O$_6$.½CH$_3$COOC$_2$H$_5$: C 66.84, H 6.79, N 12.31; Found : C 66.10, H 6.93, N 11.56.

EXAMPLE 33

To a solution of Starting Compound (0.70 g) in DMF (10 ml), NMM (0.14 ml) was added at 4° C. Then

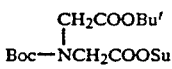

(0.47 g) was added and stirred at room temperature for 2 hours. After evaporation, the residue was dissolved in methylene chloride (20 ml) and N,N'-dimethyl-1,3-propanediamine (10 drops) was added. The mixture was stirred for 30 minutes, then evaporated. The residue was dissolved ethyl acetate, and the organic layer was washed successively with 2% hydrochloric acid, water, 5% sodium hydrogencarbonate, water and brine. The organic layer was dried over anhydrous magnesium sulfate, then evaporated. The residue was subjected to column chromatography on silica gel (30 g) and eluted with a mixture of chloroform and methanol (20:1). The fractions containing the object compound were combined and evaporated. The residue was pulverized with IPE, filtered and dried to give Object Compound (0.67 g).

IR (Nujol) : 3290, 1730, 1710, 1630, 1620, 1545 cm$^{-1}$

NMR (DMSO-d$_6$, δ) : 1.20–1.50 (4H, m), 1.33 (s) and 1.35 (s)(9H), 1.40 (s) and 1.41 (s)(9H), 1.50–1.80 (2H, m), 2.72 (s) and 2.81 (s)(3H), 2.80–3.20 (4H, m), 3.70–3.90 (4H, m), 4.30–4.60 (3H, m), 4.90–5.10 (1H, m), 7.00–7.40 (12H, m), 7.40–7.50 (1H, m), 7.70–7.85 (1H, m), 7.90–8.00 (1H, m), 8.10–8.20 (2H, m), 8.30–8.40 (1H, m), 11.60 (1H, s)

EXAMPLE 34

To a solution of Starting Compound (0.70 g) and morpholinecarbonyl chloride (0.18 g) in DMF (10 ml), NMM (0.28 ml) was added. The mixture was stirred for 4 hours and allowed to stand overnight. The evaporated residue was dissolved in a mixture ethyl acetate and THF and washed successively with 2% hydrochloric acid, water, 5% sodium hydrogencarbonate, water and brine. The organic layer was dried over anhydrous magnesium sulfate and evaporated. The residue was subjected to column chromatography on silica gel (25 g) and eluted with a mixture of chloroform and methanol (20:1). The fractions containing the object compound were combined and evaporated to give Object Compound (0.29 g).

IR (Nujol) : 3270, 1630, 1540 cm$^{-1}$

NMR (DMSO-d$_6$, δ) : 1.20–1.55 (4H, m), 1.55–1.80 (2H, m), 2.72 (s) and 2.80 (s)(3H), 2.80–3.10 (4H, m), 3.10–3.30 (4H, m), 3.40–3.60 (4H, m), 4.30–4.60 (3H, m), 4.90–5.10 (1H, m), 6.40–6.55 (1H, m), 7.00–7.40 (12H, m), 7.40–7.50 (1H, m), 7.77 (1H, d, J=8Hz), 8.10–8.20 (2H, m), 8.37 (1H, d, J=8Hz), 11.60 (1H, s)

EXAMPLE 35

To an ice-cooled solution of Starting Compound (1.0 g) in DMF (10 ml) were added pyridine (1.5 ml) and acetic anhydride (0.7 ml). The solution was stirred three hours at room temperature and DMAP (0.1 g) was added. The solution was stirred for further an hour and concentrated. The product was extracted with ethyl acetate and the organic layer was washed successively with 1N-hydrochloric acid, water, 5% sodium hydrogencarbonate solution, water, and sodium chloride solution and dried over magnesium sulfate. Evaporation and trituration of the extract gave Object Compound (0.85 g) as an amorphous solid.

mp 89°–91° C.

IR (Nujol) : 3330, 1740, 1635, 1605, 1245 cm$^{-1}$

NMR (DMSO-d$_6$, δ) : 1.9–2.3 (2H, m), 1.98 (3H, s), 2.69 (s) and 2.76 (s)(3H), 2.7–3.1 (2H, m), 3.8–4.3 (2H, m), 3.85 (3H, s), 4.41 (2H, s), 4.7–4.8 (1H, m), 4.8–5.1 (1H, m), 5.24 (1H, br s), 6.9–7.4 (12H, m), 7.50 (1H, d, J=8Hz), 7.91 (1H, br s), 8.06 (1H, d, J=8Hz), 8.52 (1H, br s)

Elemental Analysis. Calculated for C$_{34}$H$_{36}$N$_4$O$_5$.½H$_2$O C 69.25, H 6.32, N 9.50; Found : C 69.64, H 6.28, N 9.52.

EXAMPLE 36

To an ice-cooled solution of Starting Compound (1.0 g), Z-Gly-OH (0.4 g), and HOBT (0.26 g) in DMF (10 ml) was added WSC.HCl (0.37 g). The solution was stirred at room temperature for three hours and concentrated. The product was extracted with ethyl acetate and the organic layer was successively washed with water, 1N-hydrochloric acid, water, 5% sodium hydrogencarbonate solution, water, and sodium chloride solution and dried over magnesium sulfate. After evaporation, the crude product was purified on a silica gel column (75 g) eluting with chloroform-methanol (20:1) to give Object Compound (1.3 g) as an amorphous solid.

IR (Nujol) : 3250, 1720, 1710, 1660, 1635, 1525 cm$^{-1}$

NMR (DMSO-d$_6$, δ) : 1.6–1.9 (1H, m), 2.3–2.6 (1H, m), 2.68 (s) and 2.73 (s)(3H), 2.7–3.2 (2H, m), 3.4–3.7 (3H, m), 4.0–5.0 (6H, m), 5.02 (2H, s), 6.9–7.5 (19H, m), 7.81 (1H, s), 8.01 (1H, d, J=8Hz), 8.1–8.3 (1H, m), 8.5–8.7 (1H, m), 11.66 (1H, s)

EXAMPLE 37

To a solution of Starting Compound (0.93 g) in ethanol 25 ml) was added 4N-HCl/DOX (3.25 ml) and the solution was hydrogenated under atmospheric pressure in the presence of 10% palladium on carbon (1.3 g) for ten hours. After filtration and evaporation, the residue was dissolved in water (50 ml) and the solution was shaken twice with ethyl acetate (25 ml). The aqueous layer was separated and filtered through a Millipore filter and lyophilized to give Object Compound (0.49 g) as a powder.

IR (Nujol) : 3220, 1625, 1525 cm$^{-1}$

DMSO-d$_6$, δ) : 1.7–2.0 (1H, m), 2.4–2.6 (1H, m), 2.68 (s) and 2.74 (s)(3H), 2.7–3.2 (2H, m), 3.4–3.9 (3H, m), 4.1–5.1 (6H, m), 6.9–7.4 (12H, m), 7.45 (1H, d, J=7Hz), 7.79 (1H, s), 7.98 (1H, d, J=8Hz), 8.20 (3H, br s), 8.4–8.7 (1H, m), 8.7–8.9 (1H, m), 11.84 (1H, s)

EXAMPLE 38

Starting Compound (1.13 g) was dissolved in ethanol (200 ml), and the solution was hydrogenated under atmospheric pressure in the presence of 20% palladium hydroxide on carbon (2.2 g) for three hours. After filtration and evaporation, the residue was triturated with IPE, and dried to give Object Compound (0.53 g) as an amorphous solid.

IR (Nujol) : 3250, 1630, 1525 cm$^{-1}$
NMR (DMSO-d$_6$, δ) : 1.6–1.9 (1H, m), 1.9–2.1 (2H, m), 2.2–2.5 (3H, m), 2.69 (s) and 2.75 (s)(3H), 2.7–3.2 (2H, m), 3.76 (1H, t, J=6Hz), 4.0–4.8 (5H, m), 4.8–5.1 (1H, m), 6.9–7.3 (12H, m), 7.47 (1H, d, J=7Hz), 7.81 (1H, s), 7.99 (1H, d, J=8Hz)

EXAMPLE 39

To an ice-cooled solution of Starting Compound (1.0 g) and TEA (0.27 ml) in DMF (10 ml) was added succinic anhydride (0.19 g) at a time. The solution was stirred at the same temperature for three quarters an hour and concentrated. The product was extracted with ethyl acetate and the organic layer was washed successively with 1N hydrochloric acid, water and 5% sodium hydrogencarbonate solution. The last aqueous layer was then acidified to pH 2 with 1N hydrochloric acid and extracted with ethyl acetate. The extract was washed sodium chloride solution and dried with magnesium sulfate. After concentration the residue (1.1 g) was dissolved in a mixed solvent of ethanol (70 ml) and water (130 ml) and 1N sodium hydroxide solution (1.55 ml) was added. After evaporation of the alcohol, the solution was filtered through a Millipore Filter (trademark, prepared by Millipore Corporation) (type HA, 0.45 μm) and lyophilized to give Object Compound (1.07 g) as a powder.

IR (Nujol) : 3200, 1640, 1630, 1570-1515 cm$^{-1}$
NMR (DMSO-d$_6$, δ) : 1.6–1.9 (1H, m), 2.1–2.3 (4H, m), 2.3–2.5 (1H, m), 2.68 (s) and 2.74 (s)(3H), 2.7–3.2 (2H, m), 4.0–4.8 (5H, m), 4.8–5.1 (1H, m), 6.9–7.4 (12H, m), 7.47 (1H, d, J=7Hz), 7.82 (1H, s), 8.00 (1H, d, J=8Hz), 8.5–8.8 (2H, m), 12.17 (1H, broad)

EXAMPLE 40

To an ice-cooled solution of Starting Compound (1.45 g) in ethanol (30 ml) was added a solution of 1N sodium hydroxide (1.94 ml). The solution was stirred at room temperature for two hours. After evaporation of alcohol, water (50 ml) was added and the solution was lyophilized to give Object Compound (1.26 g) as a powder.

IR (Nujol) : 3300 (broad), 1635, 1520 cm$^{-1}$
NMR (DMSO-d6, δ) : 1.7–1.9 (1H, m), 2.3–2.5 (1H, m), 2.67 (s) and 2.75 (s)(3H), 2.7–3.0 (1H, m), 3.0–3.2 (1H, m), 3.6–3.8 (1H, m), 4.0–4.8 (5H, m), 4.8–5.1 (1H, m), 6.9–7.3 (12H, m), 7.46 (1H, d, J=7Hz), 7.84 (1H, s), 8.03 (1H, d, J=8Hz), 8.4–8.7 (2H, m), 11.85 (1H, broad)

EXAMPLE 41

Starting Compound (1.0 g) was dissolved in THF (15 ml). Sodium 2-ethylhexanoate (287 mg) was added to the solution. THF (25 ml) was added into it, and the suspended mixture was stirred for half an hour. After concentration of the solution to one-fourth of its original volume, diethyl ether (50 ml) was added and the resulting precipitates were collected. After drying, the product was dissolved in water (100 ml) and shaken once with diethyl ether (50 ml). The aqueous layer was lyophilized to give Object Compound (820 mg) as a powder.

IR (Nujol) : 3350, 1630-1600 cm$^{-1}$
NMR (DMSO-d$_6$, δ) : 1.75–2.1 (2H, m), 2.69 and 2.76 (3H, s), 2.8–3.1 (2H, m), 3.6–3.74 and 3.8–4.0 (2H, m), 4.30 (1H, m), 4.41 (2H, s), 4.54 (2H, s), 4.72 (1H, m), 4.9–5.2 (2H, m), 6.95–7.4 (13H, m), 7.83 (1H, s), 8.03 (1H, d, J=7Hz), 8.44 (1H, m)

EXAMPLE 42

To a solution of Starting Compound (1.0 g) in DMF (5 ml), was added methyl mercaptan sodium salt (ca. 15% in water, 1.35 ml). The solution was stirred at room temperature for 9 hours and allowed to stand overnight. Then the solution was poured to a mixture of ethyl acetate and sodium hydrogencarbonate solution. The organic layer was washed with sodium hydrogencarbonate solution, 1N sodium hydroxide solution, water and brine, and was dried over magnesium sulfate. After evaporation, the crude product was purified by column chromatography on silica gel (40 g) eluting with chloroform-methanol (50:1) crystallization with ethanol-hexane gave Object Compound (0.48 g).

IR (Nujol) : 3350, 1705, 1640, 1620, 1605, 1530 cm$^{-1}$
NMR (DMSO-d$_6$, δ) : 1.4–2.0 (2H, m), 2.11 (3H, s), 2.4–3.7 (3H, m), 2.68 (s), 2.76 (s) and 2.80 (s)(3H), 3.83 (s) and 3.86 (s)(3H), 4.0–5.2 (6H, m), 6.9–7.4 (12H, m), 7.50 (1H, d, J=8Hz), 7.95 (1H, br s), 8.02 (1H, d, J=8Hz), 8.44 (1H, m)

EXAMPLE 43

The object compounds were obtained according to a similar manners to those of Preparation 4 and Example 4, successively.

(1)
IR Nujol) : 3310, 1655, 1650, 1620, 1565, 1545 cm$^{-1}$
NMR (DMSO-d$_6$, δ) : 1.8–2.1 (2H, m), 2.03 (3H, s), 2.4–2.6 (2H, m), 2.72 (s) and 2.81 (s)(3H), 2.8–3.1 (2H, m), 3.85 (3H, s), 4.3–4.7 (3H, m), 4.9–5.1 (1H, m), 7.0–7.3 (12H, m), 7.50 (1H, d, J=7Hz), 7.85 (1H, d, J=8Hz), 8.1–8.2 (1H, m), 8.12 (1H, s), 8.3–8.5 (1H, m)

(2)
mp : 85°–87° C.
IR (Nujol) : 3300, 1630, 1535 cm$^{-1}$
NMR (DMSO-d$_6$, δ) : 1.04 (d, J=6Hz) and 1.06 (d, J=6Hz)(3H), 2.71 (s) and 2.80 (s)(3H), 2.8–3.1 (2H, m), 3.86 (3H, s), 4.0–4.1 (1H, m), 4.3–4.6 (3H, m), 4.92 (1H, d, J=6Hz), 4.9–5.1 (1H, m), 6.9–7.3 (12H, m), 7.43 (1H, d, J=8Hz), 7.52 (1H, d, J=8Hz), 8.09 (1H, d, J=8Hz), 8.13 (1H, s), 8.34 (1H, d, J=8Hz)
Elemental Analysis Calculated for C$_{31}$H$_{34}$N$_4$O$_4$.½ H$_2$O C 69.51, H 6.59, N 10.46; Found : C 69.73, H 6.44, N 10.38.

(3)
IR (Nujol) : 3300, 1630, 1540, 1240 cm$^{-1}$
NMR (DMSO-d$_6$, δ) : 1.23 (d, J=7Hz) and 1.28 (d, J=7Hz)(3H), 2.73 (s) and 2.81 (s)(3H), 2.8–3.1 (2H, m), 3.84 (3H, s), 4.4–4.6 (3H, m), 4.9–5.1 (1H, m), 7.0–7.3 (13H, m), 7.50 (1H, d, J=8Hz), 7.80 (d, J=8Hz) and 7.83 (d, J=8Hz)(1H), 8.11 (1H, s), 8.12 (1H, d, J=8Hz), 8.3–8.4 (1H, m)

(4)
mp : 89°–91° C.
IR (Nujol) : 3260, 1670, 1630, 1585, 1570, 1530, 1100 cm$^{-1}$
NMR (DMSO-d$_6$, δ) : 1.7–2.0 (1H, m), 2.0–2.3 (1H, m), 2.69 (s) and 2.77 (s)(3H), 2.7–3.1 (2H, m), 3.19 (3H, s), 3.7–4.1 (6H, m), 4.3–4.5 (2H, m), 4.5–4.7 (1H, m), 4.8–5.1 (1H, m), 6.9–7.3 (12H, m), 7.49 (1H, d, J=8Hz), 7.91 (1H, br s), 8.05 (1H, d, J=8Hz), 8.44 (1H, br s)
Elemental Analysis. Calculated for C$_{33}$H$_{36}$N$_4$O$_4$.½ H$_2$O C 70.57, H 6.64, N 9.97; Found : C 70.76, H 6.78, N 9.77.

(5)
Neat) : 1640-1630, 1540 cm$^{-1}$

NMR (DMSO-d$_6$, δ) : 2.6-3.4 (9H, m), 3.5-3.7 (1H, m), 3.7-3.9 (3H, m), 4.0-4.8 (4H, m), 5.0-5.3 (1H, m), 5.5-5.7 (1H, m), 6.8-7.4 (17H, m), 7.4-7.6 (1H, m), 7.8-8.2 (3H, m)

EXAMPLE 44

The object compounds were obtained according to a similar manner to that of Example 4.

(1)
IR (Nujol) : 3250, 1735, 1645 (sh), 1630, 1545 cm$^{-1}$
NMR (DMSO-d$_6$, δ) : 2.6-3.1 (4H, m), 2.79 (3H, s), 4.40 (2H, s), 4.8-5.1 (2H, m), 5.05 (2H, s), 6.9-7.8 (19H, m), 8.3 (1H, m), 8.65 (1H, m), 11.6 (1H, s)

(2)
mp : 222°-224° C.
IR (Nujol) : 3280, 1680 (sh), 1660 (sh), 1645, 1630, 1550, 1535 cm$^{-1}$
NMR (DMSO-d$_6$, δ) : 1.23 (9H, s), 1.6-2.7 (4H, m), 2.55-3.05 (4H, m), 2.70 and 2.76 (3H, s), 4.0-4.3 (1H, m), 4.3-4.7 (2H, m), 4.7-5.1 (2H, m), 6.64 (1H, br s), 6.9-7.3 (14H, m), 7.3-7.7 (3H, m), 7.9-8.1 (1H, m), 8.2-8.4 (1H, m), 8.45-8.65 (1H, m), 11.59 (1H, s)

(3)
NMR (CDCl$_3$, δ) 2.58 and 2.81 (3H, s), 2.5-3.1 (4H, m), 3.73 and 3.75 (2H, s), 4.07 and 4.19 (ABq, J=16.5Hz) and 4.25 and 4.63 (ABq, J=14.6Hz)(Two set of ABq, 2H), 4.8-5.1 (4H, m), 6.7-7.4 (16H, m), 7.5-7.6 (1H, m), 8.49 (1H, s)

(4)
IR (Nujol) : 3250, 1710, 1620, 1550, 1530, 1240 cm$^{-1}$
NMR (DMSO-d$_6$, δ) : 1.2-2.8 (6H, m), 2.69 and 2.73 (3H, s), 2.8-3.15 (4H, m), 4.3-4.7 (3H, m), 4.8-5.1 (1H, m), 5.06 (2H, s), 6.9-7.7 (18H, m), 8.2-8.5 (2H, m), 11.58 (1H, s)

(5)
IR (Nujol) : 3300, 1700, 1640, 1630 cm$^{-1}$
NMR (DMSO-d$_6$, δ) : 1.0-1.7 (6H, m), 2.71 (s) and 2.76 (s)(3H), 2.8-3.1 (4H, m), 3.4-3.7 (2H, m), 4.2-4.4 (1H, m), 4.43 (2H, s), 4.8-5.1 (1H, m), 5.00 (2H, s), 6.8-7.5 (20H, m), 7.55 (1H, d, J=8Hz), 7.92 (1H, d, J=8Hz), 8.40 (1H, d, J=8Hz), 10.86 (1H, s)

(6)
IR (Nujol) : 3250, 1630, 1490 cm$^{-1}$
NMR (DMSO-d$_6$, δ) : 1.7-2.0 and 2.1-2.3 (2H, m), 2.7-3.1 (5H, m), 3.4-4.0 (4H, m), 4.2-4.75 (4H, m), 4.85-5.2 (2H, m), 6.8-7.35 (11H, m), 7.5 (1H, m), 7.67 and 7.8 (1H, m), 8.42 (d, J=8.1Hz) and 8.9 (m)(1H), 12.95 and 12.98 (1H, br s)

(7)
IR (CH$_2$Cl$_2$) : 3600, 3400, 3300, 1620, 1505 cm$^{-1}$
NMR (DMSO-d$_6$, δ) : 1.7-2.4 (2H, m), 2.6-3.1 (9H, m), 3.25-3.45 (2H, m), 4.1-4.6 (4H, m), 4.85-5.1 (2H, m), 6.6-6.7 (2H, m), 6.9-7.4 (12H, m), 8.3-8.4 (m) and 8.7-8.8 (m)(1H), 9.1-9.15 (1H, m)

(8)
IR (CH$_2$Cl$_2$) : 1650 (sh), 1630, 1600, 1480, 1380, 1150 cm$^{-1}$
NMR (DMSO-d$_6$, δ) : 1.42 and 1.53 (9H, s), 1.8-2.05 (2H, m), 2.64 and 2.69 (3H, s), 2.75-3.1 (4H, m), 3.4-3.6 (2H, m), 4.3-4.6 (4H, m), 4.8-5.2 (3H, m), 6.85-7.0 (3H, m), 7.1-7.4 (10H, m), 7.73 (1H, d, J=8Hz), 8.40 (1H, d, J=8Hz)

(9)
mp : 122°-124° C.
NMR (DMSO-d$_6$, δ) : 1.7-2.1 (2H, m), 2.69 and 2.77 (3H, s), 2.9-3.1 (2H, m), 3.6-3.7 (1H, m), 3.85 (1H, m), 3.85 (3H, s), 4.2-4.6 (3H, m), 4.65-4.75 (1H, m), 4.9-5.05 (2H, m), 7.0-7.3 (12H, m), 7.49 (1H, d, J=7.9Hz), 7.88 (1H, s), 8.06 (1H, d, J=7.5Hz), 8.4 (1H, m)

(10)
mp : 92°-96° C.
IR (Nujol) : 3430, 3300, 1660, 1630, 1605, 1545 cm$^{-1}$
NMR (DMSO-d$_6$, δ) : 1.51 (6H, s), 1.7-2.1 (2H, m), 2.69 and 2.77 (3H, s), 2.8-3.2 (2H, m), 3.67 (br s) and 3.9-4.1 (m)(1H), 4.2-4.5 (3H, m), 4.6-5.0 (4H, m), 6.9-7.3 (12H, m), 7.58 (1H, d, J=7.6Hz), 7.89 (1H, m), 8.64 (1H, d, J=7.3Hz), 8.45 (1H, m)

(11)
IR (Nujol) : 3250, 1640, 1600, 1525, 1510 cm$^{-1}$
NMR (DMSO-d$_6$, δ) : 1.8-2.3 (2H, m), 2.72 and 2.79 (3H, s), 2.91 (1H, d of ABq, J=13.9Hz, 6.3Hz), 3.06 (1H, d of ABq, J=13.9Hz, 7.4Hz), 3.6-4.1 (2H, m), 4.3-4.53 (3H, m), 4.6-4.7 (1H, m), 4.9-5.2 (2H, m), 6.9-7.5 (13H, m), 7.7 (1H, m), 8.5-8.8 (1H, m), 11.69 and 11.79 (1H, s)

(12)
IR (Nujol) : 3280, 1642, 1608, 1580, 1510 cm$^{-1}$
NMR (DMSO-d$_6$, δ) : 1.7-2.2 (2H, m), 2.6-3.1 (5H, m), 3.5-3.6 (2H, m), 4.2-4.6 (4H, m), 4.9-5.1 (2H, m), 6.4-7.6 (14H, m), 8.4 and 8.8 (1H, m), 9.87 (1H, br s)

(13)
mp : 135°-137° C.
IR (Nujol) : 3280, 1670, 1645, 1595, 1580, 1512 cm$^{-1}$
NMR (DMSO-d$_6$, δ) : 1.7-2.2 (2H, m), 2.6-3.1 (5H, m), 3.5-3.7 (2H, m), 3.80 (3H, s), 3.82 (3H, s), 4.2-4.6 (4H, m), 4.8-5.2 (2H, m), 6.6-7.5 (12H, m), 8.4 and 8.9 (1H, m), 8.82 (1H, br s)

(14)
mp : 103°-105° C.
IR (Nujol) : 3420, 3330, 1665, 1645, 1630, 1540 cm$^{-1}$
NMR (DMSO-d$_6$, δ) : 0.77 (d, J=6Hz) and 0.88 (d, J=6Hz)(6H), 1.2-2.3 (6H, m), 2.71 (s), 2.76 (s) and 2.87 (s)(3H), 2.8-3.1 (2H, m), 3.3-3.7 (2H, m), 4.1-4.6 (4H, m), 4.8-5.1 (2H, m), 7.0-7.4 (10H, m), 8.30 (d, J=8Hz) and 8.72 (d, J=8Hz)(1H)
Elemental Analysis. Calculated for C$_{28}$H$_{37}$N$_3$O$_4$: C 70.12, H 7.78, N 8.76; Found : C 69.98, H 7.65, N 8.69.

(15)
IR (Nujol) : 3270, 1640 (sh), 1630, 1595, 1520, 1204 cm$^{-1}$
NMR(DMSO-d$_6$, δ) : 1.7-2.3 (2H, m), 2.79 and 2.85 (3H, s), 2.90 (1H, d, of ABq, J=13.9Hz, 6.5Hz), 3.06 (1H, d of ABq, J=13.9Hz, 7.5Hz), 3.77 (3H, s), 3.65-3.85 (1H, m), 3.9-4.1 (1H, m), 4.3-4.5 (3H, m), 4.6-4.7 (1H, m), 4.9-5.2 (2H, m), 6.8-7.4 (14H, m), 8.6-8.8 (1H, m), 11.34 and 11.43 (1H, s)

(16)
IR (Nujol) : 3270, 1630, 1600, 1530 cm$^{-1}$
NMR (DMSO-d$_6$, δ) : 1.7-2.1 (2H, m), 2.38 (3H, s), 2.72 and 2.79 (3H, s), 2.91 (1H, d of ABq, J=13.4Hz and 7.1Hz), 3.06 (1H, d of ABq, J=13.4Hz, 7.4Hz), 3.7-4.1 (2H, m), 4.3-4.55 (3H, m), 4.6-4.75 (1H, m), 4.9-5.15 (2H, m), 6.9-7.4 (14H, m), 8.5-8.8 (1H, m), 11.34 and 11.45 (1H, s)

(17)
IR (Nujol) : 3300, 1630, 1525 cm$^{-1}$
NMR (DMSO-d$_6$, δ) : 1.6-1.9 (1H, m), 2.0-2.2 (1H, m), 2.4-3.2 (5H, (singlet at 2.71 and 2.79), 3.6-3.72 (2H, m), 3.83 (3H, s), 4.2-5.2 (6H, m), 6.55-7.35 (13H, m), 7.4-7.7 (2H, m), 8.5-8.62 (1H, m)

(18)
IR (Nujol) : 3220, 1640, 1530 cm$^{-1}$
NMR (DMSO-d$_6$, δ) : 1.6-2.3 (2H, m), 2.45-3.1 (5H, m), 3.7-4.1 (2H, m), 4.25-4.55 and 4.65-4.8 (5H, m), 4.9-5.1 and 5.4-5.5 (1H, m), 7.65-7.35 (10H, m), 7.6-8.2 (5H, m), 8.4-8.7 (1H, m)

(19)
IR (CH$_2$Cl$_2$) : 3400, 1670, 1635 cm$^{-1}$

NMR (DMSO-d$_6$, δ) : 1.7–2.1 and 2.2–2.4 (2H, m), 2.68–3.1 (5H, m), 3.82 and 3.92 (3H, s), 3.35–3.6 (2H, m), 4.0–5.3 (8H, m), 6.55–7.55 (13H, m), 7.9–8.05 (2H, m), 8.36 (d, J=7.8Hz) and 8.94 (m)(1H)

(20)

mp : 157°–158° C.

IR (Nujol) : 3420, 3300, 1625 cm$^{-1}$

NMR (DMSO-d$_6$, δ) : 2.72 (s) and 2.80 (s)(3H), 2.8–3.1 (2H, m), 3.6–3.7 (2H, m), 3.85 (3H, s), 4.3–4.6 (3H, m), 4.92 (1H, t, J=5.5Hz), 4.9–5.1 (1H, m), 7.0–7.3 (12H, m), 7.51 (1H, d, J=8Hz), 7.6–7.7 (1H, m), 8.1–8.2 (2H, m), 8.34 (1H, t, J=8Hz)

Elemental Analysis. Calculated for C$_{30}$H$_{32}$N$_4$O$_4$: C 70.29, H 6.29, N 10.93; Found : C 70.19, H 6.26, N 10.92.

(21)

IR (Nujol) : 3300, 1620, 1512 cm$^{-1}$

NMR (DMSO-d$_6$, δ) : 1.7–2.4 (2H, m), 2.6–3.0 (5H, m), 3.6–4.1 (2H, m), 4.3–4.5 (3H, m), 4.6–4.7 (1H, m), 4.8–5.2 (2H, m), 6.6–7.8 (14H, m), 8.52 and 8.65 (d, J=7.7Hz), 9.2 (1H, m)

(22)

mp : 124°–128° C.

IR (Nujol) : 3270, 1656, 1630 (sh), 1610, 1514 cm$^{-1}$

NMR (DMSO-d$_6$, δ) : 1.51 (6H, br s), 1.75–2.2 (2H, m), 2.6–3.0 (5H, m), 3.65 (1H, d, J=9.6Hz), 3.9–4.1 (1H, m), 4.2–4.5 (3H, m), 4.6–5.0 (4H, m), 6.5–6.6 (2H, m), 6.8–7.4 (9H, m), 7.58 (1H, d, J=7.8Hz), 7.9 (1H, br s), 8.04 (1H, d, J=7.4Hz), 8.38 (1H, m), 9.22 (1H, s)

(23)

IR (Nujol) : 3280, 1630, 1510 cm$^{-1}$

NMR (DMSO-d$_6$, δ) : 0.88 (6H, d, J=6Hz), 1.2–2.3 (7H, m), 2.6–3.0 (5H, m), 3.3–3.5 (1H, m), 3.5–3.7 (1H, m), 4.1–4.6 (4H, m), 4.7–5.1 (1H, m), 6.6–6.7 (2H, m), 6.8–7.1 (4H, m), 7.2–7.3 (3H, m), 8.24 (d, J=8Hz) and 8.65 (d, J=8Hz)(1H), 9.20 (s) and 9.22 (s)(1H)

(24)

NMR (DMSO-d$_6$, δ) : 1.8–2.15 (2H, m), 2.67 and 2.75 (3H, s), 2.8–3.0 (2H, m), 3.6–3.7 (1H, m), 3.8–3.9 (1H, m), 3.85 (3H, s), 4.3–4.5 (3H, m), 4.7–4.8 (1H, m), 4.9 (1H, m), 5.0–5.04 (1H, m), 6.53–6.65 (2H, m), 6.9–7.3 (9H, m), 7.5 (1H, d, J=8Hz), 7.89 (1H, br s), 8.06 (1H, d, J=8Hz), 8.4 (1H, m), 9.23 (1H, s)

(25)

IR (Nujol) : 3230, 1640, 1610, 1515 cm$^{-1}$

NMR (DMSO-d$_6$, δ) : 1.7–1.9 (1H, m), 1.9–2.3 (1H, m), 2.6–3.1 (5H, m), 3.7–3.8 (m) and 4.0–4.4 (3H, m), 4.6–5.0 (m) and 5.3–5.4 (1H, m), 6.5–6.7 (2H, m), 6.8–7.1 (2H, m), 7.1–7.3 (3H, m), 7.3–7.8 (2H, m), 8.0–8.2 (2H, m), 8.44 (d, J=8Hz) and 8.56 (d, J=8Hz)(1H), 8.7–8.8 (1H, m), 13.49 (s) and 13.71 (s)(1H)

(26)

IR (Nujol) : 3400–3000, 1640–1610, 1340, 750 cm$^{-1}$

NMR (DMSO-d$_6$, δ) : 1.7–1.9 (1H, m), 1.9–2.3 (1H, m), 2.7–3.2 (5H, m), 3.6–3.8 (m) and 4.0–4.4 (m)(3H), 4.6–5.0 (m) and 5.3–5.4 (m)(4H), 7.0–7.5 (8H, m), 7.5–7.7 (2H, m), 8.0–8.2 (2H, m), 8.5–8.8 (2H, m), 13.50 (s) and 13.74 (s)(1H)

(27)

IR (Nujol) : 3420, 3300, 1745, 1660, 1635, 1605, 1570, 1535 cm$^{-1}$

NMR (DMSO-d$_6$, δ) : 1.7–2.1 (2H, m), 1.88 (s) and 1.90 (s)(3H), 2.8–3.1 (2H, m), 3.2–3.4 (2H, m), 3.6–4.0 (7H, m), 4.1–4.9 (4H, m), 4.9–5.1 (2H, m), 7.0–7.4 (13H, m), 7.50 (1H, d, J=8Hz), 7.85 (1H, s), 8.01 (1H, m)

(28)

IR (Nujol) : 3350 (broad), 1635, 1525 cm$^{-1}$

NMR (DMSO-d$_6$, δ) : 1.6–2.1 (2H, m), 2.71 (s) and 2.79 (s)(3H), 2.7–3.1 (2H, m), 3.6–3.7 (1H, m), 3.9–4.1 (1H, m), 4.2–4.7 (4H, m), 4.8–5.1 (2H, m), 6.9–7.4 (11H, m), 7.47 (1H, t, J=8Hz), 8.14 (1H, d, J=8Hz), 8.44 (2H, br s), 8.82 (1H, br d)

(29)

IR (Nujol) : 3250, 1640, 1580, 1510, 1285 cm$^{-1}$

NMR (DMSO-d$_6$, δ) : 1.7–2.2 (2H, m), 2.73 and 2.80 (3H, s), 2.8–3.1 (2H, m), 3.2–3.8 (2H, m), 4.1–5.2 (6H, m), 6.3–7.4 (15H, m), 8.4 and 8.85 (1H, m), 9.2 (2H, br)

(30)

IR (Nujol) : 3400–3300, 2600, 2450, 1640, 1600 cm$^{-1}$

NMR (DMSO-d$_6$, δ) : 1.7–2.2 (2H, m), 2.74 and 2.79 (3H, s), 2.7–3.0 (2H, m), 2.99 (3H, s), 3.04 (3H, s), 3.5–3.9 (2H, m), 4.2–4.6 (4H, m), 4.7–5.0 (2H, m), 6.5–7.8 (16H, m), 8.4 and 7.9 (1H, m)

(31)

mp : 167°–169° C.

IR (Nujol) : 3440, 3290, 3120, 1660, 1640, 1605, 1575, 1490 cm$^{-1}$

NMR (DMSO-d$_6$, δ) : 1.6–1.9 (1H, m), 1.9–2.1 (1H, m), 2.70 (s) and 2.83 (s)(3H), 2.8–3.1 (2H, m), 3.6–4.0 (2H, m), 3.85 (3H, s), 4.2–4.4 (4H, m), 4.65 (1H, t, J=8Hz), 4.8–5.1 (1H, m), 6.8–7.0 (m) and 7.0–7.4 (m)(11H), 7.49 (1H, d, J=8Hz), 7.9 (1H, br s), 8.05 (1H, d, J=8Hz), 8.3–8.5 (1H, m)

(32)

mp : 146°–147° C.

IR (Nujol) : 3460, 3280, 3250, 3100, 1660, 1645, 1605, 1575, 1535, 1415 cm$^{-1}$ NMR (DMSO-d$_6$, δ) : 1.7–1.9 (1H, m), 1.9–2.1 (1H, m), 2.72 (s) and 2.88 (s)(3H), 2.8–3.1 (2H, m), 3.5–3.7 (1H, m), 3.8–4.1 (1H, m), 3.85 (3H, s), 4.2–4.5 (2H, m), 4.6–4.8 (2H, m), 4.9–5.1 (2H, m), 6.87 (1H, d, J=7Hz), 7.0–7.8 (11H, m), 7.91 (1H, br s), 8.06 (1H, d, J=7Hz), 8.4–8.6 (1H, m)

(33)

mp : 206°–207° C.

IR (Nujol) : 3430, 3300, 3120, 1660, 1635, 1615, 1575, 1535, 1250 cm$^{-1}$

NMR (DMSO-d$_6$, δ) : 1.7–1.9 (1H, m), 1.9–2.1 (1H, m), 2.70 (s) and 2.78 (s)(3H), 2.9–3.1 (2H, m), 3.6–3.7 (2H, m), 3.65 (3H, s), 4.2–4.6 (2H, m), 4.6–4.8 (2H, m), 4.8–5.1 (2H, m), 6.8–7.4 (11H, m), 7.48 (1H, d, J=7Hz), 7.88 (1H, s), 8.05 (1H, d, J=7Hz), 8.4–8.6 (1H, m)

(34)

mp : 70° C.~(dec.)

IR (Nujol) : 3350, 1640, 1605, 1530, 1495, 1430 cm$^{-1}$

NMR (DMSO-d$_6$, δ) : 1.7–2.0 (3H, m), 2.0–2.2 (1H, m), 2.72 (s) and 2.81 (s)(3H), 2.9–3.1 (2H, m), 3.7–4.0 (5H, m), 4.3–4.7 (3H, m), 4.9–5.1 (1H, m), 7.0–7.4 (12H, m), 7.47 (1H, d, J=8Hz), 7.88 (1H, broad s), 8.08 (1H, d, J=8Hz), 8.3–8.5 (1H, m)

EXAMPLE 45

The object compounds were obtained according to a similar manner to that of Example 27.

(1)

IR (Nujol) : 3430, 3200, 1720, 1672, 1635, 1605, 1580, 1537, 1195 cm$^{-1}$

NMR (DMSO-d$_6$, δ) : 2.6–3.0 (4H, m), 2.89 (3H, s), 4.3–4.6 (2H, m), 4.7–5.1 (2H, m), 6.9–7.3 (12H, m), 7.3–7.5 (1H, m), 7.8–8.2 (4H, m), 11.5 (1H, s), 12.1 (1H, br s)

(2),

IR (Nujol) : 3300, 1720 (sh), 1630 cm$^{-1}$

NMR (DMSO-d$_6$, δ) : 2.3–2.6 (2H, m), 2.75–3.0 (2H, m), 2.71 and 2.69 (3H, m), 3.56 (2H, s), 4.2–4.72 (3H, m), 4.8–5.0 (1H, m), 6.9–7.4 (15H, m), 7.55 (1H, d, J=7.6Hz), 8.2–8.3 (1H, m), 8.4–8.6 (1H, m), 10.91 (1H, s)

EXAMPLE 46

The object compounds were obtained according to a similar manner to that of Example 28.

(1)

IR (Nujol) : 3250, 1660 (sh), 1640, 1630, 1540 cm$^{-1}$

NMR (DMSO-d$_6$, δ) : 1.5–2.2 (4H, m), 1.24 (9H, s), 2.5–3.0 (4H, m), 2.71 and 2.78 (3H, s), 4.0–4.6 (3H, m), 4.6–5.0 (2H, m), 6.61 (1H, s), 6.9–7.5 (15H, m), 7.8–8.2 (5H, m), 11.60 (1H, s)

(2)

mp : 238°–240° C. (dec.)

IR (Nujol) : 3380, 3300, 3280 (sh), 3200 (sh), 1665, 1640, 1620, 1545 cm$^{-1}$

NMR (DMSO-d$_6$, δ) : 0.98 (3H, d, J=6Hz), 2.72 and 2.75 (3H, s), 2.6–3.1 (4H, m), 3.9–4.2 (3H, m), 4.3–4.6 (2H, m), 4.7–5.1 (3H, m), 6.9–7.4 (13H, m), 7.46 (1H, d, J=6Hz), 7.5–7.9 (3H, m), 8.3 (1H, m), 8.6 (1H, m), 11.58 (1H, s)

(3)

IR (Nujol) : 3280, 1645 (sh), 1630, 1545 cm$^{-1}$

NMR (DMSO-d$_6$, δ) : 2.74 and 2.83 (3H, s), 2.7–3.1 (4H, m), 3.2–3.65 (8H, m), 4.37 and 4.52 (2H, ABq, J=15Hz), 4.9–5.0 (2H, m), 7.0–7.4 (13H, m), 7.46 (1H, d, J=8Hz), 7.65 (1H, d, J=8Hz), 8.2–8.3 (1H, m), 8.5–8.6 (1H, m), 11.66 (1H, s)

(4)

mp : 135°–140° C.

IR (Nujol) : 3250, 1670, 1630, 1605 (sh), 1535, 1210 cm$^{-1}$

NMR (DMSO-d$_6$, δ) : 0.97 (3H, d, J=6Hz), 2.71 and 2.77 (3H, s), 2.5–3.0 (4H, m), 3.8–4.2 (2H, m), 4.3–4.5 (2H, m), 4.6–5.1 (3H, m), 6.9–7.3 (15H, m), 7.3–7.5 (1H, m), 7.6–7.8 (1H, m), 7.8–8.3 (4H, m)

Elemental Analysis. Calculated for C$_{34}$H$_{38}$N$_6$O$_6$.1-H$_2$O : C 63.34, H 6.25, N 13.03; Found C 63.74, H 6.10, N 13.15.

(5)

IR (Nujol) : 3390, 3330, 3240, 3100, 1662, 1640, 1605, 1510, 1200 cm$^{-1}$

NMR (DMSO-d$_6$, δ) : 2.5–2.95 (4H, m), 2.73 and 2.78 (3H, s), 3.63 (2H, d, J=5Hz), 4.2–4.6 (2H, m), 4.75–5.1 (2H, m), 6.95–7.6 (14H, m), 7.9–8.3 (5H, m)

(6)

mp : 218°–219° C.

IR (Nujol) : 3320, 3180, 3080, 1690, 1670, 1630, 1545 cm$^{-1}$

NMR (DMSO-d$_6$, δ) : 1.031 (3H, d, J=6Hz), 2.4–3.0 (4H, m), 2.72 and 2.74 (3H, s), 3.35 (1H, s), 4.11 (2H, m), 4.28–5.0 (5H, m), 6.9–7.4 (17H, m), 7.66–7.8 (1H, m), 8.1–8.3 (2H, m), 10.87 (1H, s)

EXAMPLE 47

The object compounds were obtained according to a similar manner to that of Example 5.

(1)

IR (Nujol) : 3400, 3300, 1660, 1630 cm$^{-1}$

NMR (DMSO-d$_6$, δ) : 1.7–2.4 (2H, m), 2.60 (s), 2.72 (s) and 2.78 (s)(3H), 2.8–3.2 (2H, m), 3.6–4.2 (2H, m), 4.2–4.8 (4H, m), 4.8–5.1 (1H, m), 5.1–5.2 (1H, m), 6.8–7.3 (10H, m), 7.3–7.6 (2H, m), 7.9–8.1 (3H, m), 8.5–8.8 (1H, m)

Elemental Analysis. Calculated for C$_{31}$H$_{31}$N$_3$O$_4$S : C 68.74, H 5.77, N 7.76; Found : C 68.57, H 5.68, N 7.77.

(2)

mp : 97°–100° C.

IR (Nujol) : 3310, 1650, 1620, 1545 cm$^{-1}$

NMR (DMSO-d$_6$, δ) : 2.73 (s) and 2.80 (s)(3H), 2.8–3.1 (2H, m), 3.5–3.6 (2H, m), 4.4–4.6 (3H, m), 4.9–5.1 (2H, m), 6.84 (1H, d, J=16Hz), 7.0–7.3 (10H, m), 7.4–7.5 (4H, m), 7.55–7.65 (2H, m), 8.1–8.2 (1H, m), 8.41 (1H, t, J=8Hz)

Elemental Analysis. Calculated for C$_{29}$H$_{31}$N$_3$O$_4$.H$_2$O : C 69.17, H 6.60, N 8.34; Found : C 69.15, H 6.59, N 8.43.

(3)

IR (Nujol) : 3300, 1625, 1515 cm$^{-1}$

NMR (DMSO-d$_6$, δ) : 0.8–1.0 (6H, m), 1.7–2.2 (4H, m), 2.7–3.0 (6H, m), 3.4–3.7 (2H, m), 4.2–4.6 (4H, m), 4.7–5.1 (2H, m), 6.64 (2H, d, J=8Hz), 6.9–7.2 (4H, m), 7.2–7.4 (3H, m), 8.2–8.3 (m) and 8.6–8.7 (m)(1H), 9.22 (1H, s)

(4)

IR (Nujol) : 3300, 1625, 1190, 1080 cm$^{-1}$

NMR (DMSO-d$_6$, δ) : 0.98 (s), 1.06 (s), 1.07 (s) and 1.10 (s)(9H), 2.6–2.9 (1H, m), 2.77 (s) and 2.79 (s)(3H), 3.0–3.3 (1H, m), 3.06 (s) and 3.11 (s)(3H), 3.3–3.5 (2H, m), 4.1–5.1 (3H, m), 5.5–5.7 (1H, m), 6.73 (1H, d, J=16Hz), 6.8–7.6 (16H, m), 8.1–8.4 (1H, m)

(5)

IR (Nujol) : 3300, 1630 cm$^{-1}$

NMR (DMSO-d$_6$, δ) : 1.6–1.9 (1H, m), 1.9–2.1 (1H, m), 2.66 (s), 2.72 (s) and 2.80 (s)(3H), 2.8–3.1 (2H, m), 3.2–3.3 (1H, m), 3.6–3.8 (1H, m), 4.2–4.8 (4H, m), 4.9–5.1 (2H, m), 6.9–7.4 (11H, m), 7.4–7.6 (4H, m), 8.44 (1H, d, J=8Hz)

EXAMPLE 48

The object compounds were obtained according to a similar manner to that of Example 29.

(1)

NMR (DMSO-d$_6$, δ) : 1.2–2.0 (6H, m), 2.57 and 2.72 (3H, s), 2.8–3.25 (4H, m), 4.0–4.7 (3H, m), 4.75–5.4 (2H, m), 4.96 (2H, s), 7.85–7.4 (21H, m), 7.6–8.2 (3H, m), 9.65 (1H, s)

(2)

IR (Nujol) : 3430, 3270, 1715, 1620, 1550 cm$^{-1}$

NMR (DMSO-d$_6$, δ) : 1.3–1.75 (4H, m), 2.71 and 2.80 (3H, s), 2.8–3.2 (4H, m), 4.3–4.6 (3H, m), 4.98 (2H, s), 4.8–5.1 (1H, m), 6.9–7.5 (17H, m), 7.67 (1H, d, J=9Hz), 8.0–8.35 (3H, m), 11.54 (1H, s)

(3)

IR (Nujol) : 3200, 1640, 1515 cm$^{-1}$

NMR (DMSO-d$_6$, δ) : 1.7–1.9 (1H, m), 1.9–2.1 (1H, m), 2.7–3.1 (5H, m), 3.6–3.7 (1H, m), 3.8–4.1 (1H, m), 4.30 (1H, br s), 4.5–5.0 (4H, m), 6.65 (2H, d, J=8Hz), 6.8–7.3 (5H, m), 7.46 (1H, d, J=8Hz), 7.6–7.7 (1H, m), 7.87 (2H, br d), 8.00 (1H, d, J=8Hz), 8.3–8.5 (1H, m), 8.68 (1H, d, J=5Hz), 11.74 (1H, s)

(4)

IR (Nujol) : 3230, 1640, 1525, 1445 cm$^{-1}$

NMR (DMSO-d$_6$, δ) : 1.6–1.8 (1H, m), 1.8–2.1 (1H, m), 2.7–3.2 (5H, m), 3.6–3.7 (1H, m), 3.8–4.1 (1H, m), 4.28 (1H, br s), 4.5–4.7 (2H, m), 4.7–5.1 (2H, m), 7.0–7.5 (10H, m), 7.5–7.7 (1H, m), 7.87 (2H, br s), 8.00 (1H, d, J=8Hz), 8.45 (1H, br d, J=8Hz), 8.68 (1H, d, J=5Hz), 11.79 (1H, s)

EXAMPLE 49

The object compounds were obtained according to a similar manner to that of Example 30.

(1)

IR (Nujol) : 3250, 1630, 1525 cm$^{-1}$

NMR (DMSO-d$_6$, δ) : 1.05–1.70 (6H, m), 2.50–3.10 (4H, m), 2.72 (s) and 2.77 (s)(3H), 3.53 (1H, d, J=15Hz), 3.62 (1H, d, J=15Hz), 4.20–4.40 (1H, m), 4.43 (s) and 4.46 (s)(2H), 4.80–5.05 (1H, m), 6.90–7.40 (14H, m), 7.56

(1H, d, J=8Hz), 8.02 (4H, br s), 8.42 (1H, d, J=8Hz), 10.93 (1H, s)

(2)

IR (Nujol) : 3200, 1625, 1535, 1205 cm$^{-1}$

NMR (DMSO-d$_6$, δ) : 1.5-1.9 (4H, m), 2.70 and 2.78 (3H, s), 2.7-3.1 (4H, m), 4.4-4.7 (3H, m), 4.8-5.1 (1H, m), 6.9-7.5 (14H, m), 7.8-8.5 (6H, m), 11.76 (1H, s)

EXAMPLE 50

The object compounds were obtained according to a similar manner to that of Example 31.

(1)

The product was used in the next reaction without purification.

(2)

IR (Nujol) : 3280, 1630, 1535 cm$^{-1}$

NMR (DMSO-d$_6$, δ) : 1.2-1.5 (4H, m), 1.36 (9H, s), 1.5-1.8 (2H, m), 2.20 (2H, t, J=7Hz), 2.72 (s) and 2.81 (s)(3H), 2.8-3.2 (6H, m), 4.3-4.6 (3H, m), 4.9-5.1 (1H, m), 6.7-6.8 (1H, m), 7.0-7.4 (12H, m), 7.4-7.5 (1H, m), 7.7-7.9 (2H, m), 8.1-8.2 (2H, m), 8.37 (1H, d, J=8Hz), 11.60 (1H, s)

(3)

IR (Nujol) : 3290, 1630, 1535 cm$^{-1}$

NMR (DMSO-d$_6$, δ) : 1.1-1.5 (4H, m), 1.37 (9H, s), 1.5-1.8 (2H, m), 2.72 (s) and 2.81 (s)(3H), 2.8-3.1 (4H, m), 3.49 (2H, d, J=6Hz), 4.3-4.6 (3H, m), 4.9-5.1 (1H, m), 6.87 (1H, t, J=6Hz), 6.9-7.4 (12H, m), 7.44 (1H, d, J=7Hz), 7.7-7.9 (2H, m), 8.1-8.2 (2H, m), 8.36 (1H, d, J=8Hz), 11.60 (1H, s)

(4)

IR (Nujol) : 1660, 1640, 1630, 1545 cm$^{-1}$

NMR (DMSO-d$_6$, δ) : 1.1-1.7 (6H, m), 1.19 (6H, t, J=7Hz), 2.5-3.3 (12H, m), 2.72 (s) and 2.77 (s)(3H), 3.4-3.7 (2H, m), 4.2-4.5 (3H, m), 4.8-5.0 (1H, m), 6.9-7.4 (14H, m), 7.55 (1H, d, J=8Hz), 7.99 (1H, d, J=8Hz), 8.1-8.2 (1H, m), 8.40 (1H, d, J=8Hz), 10.27 (1H, s), 10.91 (1H, s)

(5)

NMR (CDCl$_3$, δ) : 1.32 (3H, d, J=6Hz), 1.41 (9H, s), 1.4-2.0 (4H, m), 2.67 and 2.81 (3H, s), 2.10 (1H, s), 2.85-3.15 (4H, m), 3.7-4.1 (1H, m), 4.1-4.75 (5H, m), 4.85-5.25 (3H, m), 5.78 (1H, d, J=8Hz), 6.9-7.4 (12H, m), 7.7-8.2 (3H, m), 9.65 (1H, br s)

(6)

IR (Nujol) : 3280, 1730, 1640, 1525 cm$^{-1}$

NMR (DMSO-d$_6$, δ) : 1.6-2.1 (3H, m), 2.1-2.3 (2H, m), 2.3-2.5 (1H, m), 2.68 (s) and 2.73 (s)(3H), 2.7-3.2 (2H, m), 3.3-3.6 (1H, m), 3.9-4.8 (6H, m), 4.8-5.1 (1H, m), 5.01 (s) and 5.03 (s)(2H), 5.11 (2H, s), 6.9-7.5 (24H, m), 7.7-7.9 (1H, m), 7.99 (1H, d, J=7Hz), 8.0-8.1 (1H, m), 8.58 (1H, t, J=7Hz), 11.68 (1H, s)

(7)

IR (Nujol) : 3280, 1725, 1640, 1525 cm$^{-1}$

NMR (DMSO-d$_6$, δ) : 1.6-2.1 (3H, m), 2.3-2.5 (3H, m), 2.67 (s) and 2.72 (s)(3H), 2.7-3.1 (2H, m), 3.4-3.6 (1H, m), 3.9-4.8 (6H, m), 4.8-5.1 (1H, m), 4.98 (s) and 5.00 (s)(2H), 5.06 (2H, s), 6.9-7.0 (2H, m), 7.0-7.4 (20H, m), 7.45 (2H, d, J=8Hz), 7.79 (1H, s), 8.00 (1H, d, J=8Hz), 8.2-8.3 (1H, m), 8.5-8.6 (1H, m), 11.65 (1H, s)

EXAMPLE 51

The object compounds were obtained according to a similar manner to that of Example 32.

(1)

mp : 133°-137° C.

IR (Nujol) : 3260, 1620, 1545, 1215 cm$^{-1}$

NMR (DMSO-d$_6$, δ) : 1.0 (3H, d, J=6Hz), 1.3-1.8 (4H, m), 1.89 (3H, s), 2.70 and 2.77 (3H, s), 2.8-3.2 (4H, m), 3.8-4.25 (3H, m), 4.3-4.6 (2H, m), 4.71 (1H, d, J=6Hz), 4.8-5.1 (1H, m), 6.9-7.8 (15H, m), 8.0-8.35 (4H, m), 11.6 (1H, br)

(2)

IR (Nujol) : 3250, 1645, 1520 cm$^{-1}$

NMR (DMSO-d$_6$, δ) : 1.3-1.6 (2H, m), 1.7-2.1 (2H, m), 2.79 (s) and 2.89 (s)(3H), 2.9-3.3 (3H, m), 3.6-3.7 (1H, m), 3.9-4.1 (1H, m), 4.35-4.65 (2H, m), 4.72 (1H, d, J=3Hz), 4.9-5.1 (2H, m), 7.0-7.4 (12H, m), 7.44 (1H, d, J=7Hz), 7.7-7.9 (2H, m), 8.1-8.2 (1H, m), 11.53 (1H, s)

(3)

mp : 167°-169° C.

IR (Nujol) : 1645, 1585, 1550, 1520 cm$^{-1}$

NMR (DMSO-d$_6$, δ) : 1.4-2.2 (4H, m), 2.6-3.4 (8H, m), 3.6-3.9 (2H, m), 4.2-4.6 (2H, m), 4.8-5.1 (1H, m), 5.3-5.6 (1H, m), 6.7-7.5 (13H, m), 7.6-7.8 (1H, m), 7.8-8.1 (1H, m), 11.46 (1H, br s)

Elemental Analysis. Calculated for C$_{32}$H$_{34}$N$_4$O$_3$: C 73.54, H 6.56, N 10.72; Found : C 73.32, H 6.59, N 10.56.

(4)

mp : 175° C. (dec.)

IR (Nujol) : 3300, 1695, 1675, 1630, 1600, 1570, 1530 cm$^{-1}$

NMR (DMSO-d$_6$, δ) : 1.5-1.9 (3H, m), 1.9-2.1 (1H, m), 2.5-3.1 (4H, m), 3.4-3.8 (4H, m), 4.4-4.8 (3H, m), 5.0-5.1 (1H, m), 7.0-7.3 (11H, m), 7.41 (1H, d, J=8Hz), 7.80 (1H, s), 8.0-8.1 (1H, m), 8.2-8.4 (1H, m), 11.61 (1H, s)

Elemental Analysis. Calculated for C$_{32}$H$_{32}$N$_4$O$_3$·$\frac{3}{4}$C$_2$H$_5$OH : C 72.47, H 6.63, N 10.09; Found : C 72.14, H 6.53, N 10.05.

EXAMPLE 52

The object compounds were obtained according to a similar manner to the former half of Example 32.

(1)

NMR (DMSO-d$_6$, δ) : 1.2-1.8 (6H, m), 2.4-2.6 (2H, m), 2.72 (s) and 2.81 (s)(3H), 2.8-3.1 (6H, m), 4.4-4.6 (3H, m), 4.9-5.1 (1H, m), 7.0-7.4 (12H, m), 7.45 (1H, d, J=8Hz), 7.8-8.1 (4H, m), 8.1-8.3 (3H, m), 8.40 (1H, d, J=8Hz), 11.75 (1H, s)

(2)

NMR (DMSO-d$_6$, δ) : 1.2-1.8 (6H, m), 2.72 (s) and 2.81 (s)(3H), 2.8-3.2 (4H, m), 3.4-3.6 (2H, m), 4.3-4.6 (3H, m), 4.8-5.1 (1H, m), 7.0-7.4 (12H, m), 7.4-7.5 (1H, m), 7.93 (1H, d, J=8Hz), 8.0-8.3 (5H, m), 8.39 (1H, d, J=8Hz), 8.4-8.6 (1H, d), 11.73 (1H, s)

EXAMPLE 53

The object compounds were obtained according to a similar manner to that of Example 16.

(1)

IR (Nujol) : 3500, 3400, 1665, 1640, 1600, 1500 cm$^{-1}$

NMR (DMSO-d$_6$, δ) : 2.6-2.9 (1H, m), 2.76 (s) and 2.79 (s)(3H), 3.0-3.3 (1H, m), 3.09 (s) and 3.12 (s)(3H), 3.5-3.8 (2H, m), 4.2-4.7 (2H, m), 4.8-5.1 (2H, m), 5.58 (1H, t, J=7Hz), 6.9-7.9 (15H, m), 8.38 (1H, d, J=8Hz)

(2)

IR (Nujol) : 3300, 1625, 1490 cm$^{-1}$

NMR (DMSO-d$_6$, δ) : 2.6-2.9 (1H, m), 2.75 (s) and 2.78 (s)(3H), 3.0-3.3 (1H, m), 3.08 (s) and 3.11 (s)(3H), 3.4-3.7 (2H, m), 4.1-4.7 (2H, m), 4.8-5.1 (2H, m), 5.57 (1H, t, J=7Hz), 6.74 (1H, d, J=16Hz), 6.9-7.6 (16H, m), 8.22 (1H, d, J=8Hz)

(3)

IR (Nujol) : 3300, 1730, 1610, 1530 cm$^{-1}$

NMR (DMSO-d$_6$, δ) : 1.7-1.9 (1H, m), 2.1-2.3 (1H, m), 2.71 and 2.78 (3H, s), 2.8-3.1 (2H, m), 3.8-4.0 (2H, m), 4.01 (2H, s), 4.21 (1H, m), 4.43 (2H; s), 4.68 (1H, m), 4.97 (1H, m), 5.12 (2H, s), 7.0–7.3 (12H, m), 7.46 (1H, d, J=7.8Hz), 7.95 (1H, s), 8.07 (1H, d, J=7.4Hz), 8.45 (1H, m)

EXAMPLE 54

The object compounds were obtained according to a similar manner to the latter half of Preparation 20.

(1)

IR (Neat) : 1640, 1620, 1535 cm$^{-1}$

NMR (DMSO-d$_6$, δ) : 1.00 (s), 1.02 (s), 1.05 (s), 1.09 (s), 1.10 (s) and 1.12 (s)(9H), 2.6–2.9 (1H, m), 2.76 (s), 2.78 (s) and 2.81 (s)(3H), 3.07 (s), 3.11 (s) and 3.14 (s)(3H), 3.1–3.7 (3H, m), 3.80 (s), 3.82 (s) and 3.84 (s)(3H), 4.1–5.0 (2H, m), 5.0–5.2 (1H, m), 5.5–5.8 (1H, m), 6.8–7.4 (12H, m), 7.4–7.6 (1H, m), 7.7–8.0 (1H, m), 8.0–8.2 (1H, m), 8.10 (1H, s)

(2)

IR (Nujol) : 3440, 1670, 1640, 1600, 1500 cm$^{-1}$

NMR (DMSO-d$_6$, δ) : 0.96 (s) and 1.11 (s)(9H), 2.7–2.9 (1H, m), 2.78 (s) and 2.81 (s)(3H), 3.0–3.3 (1H, m), 3.09 (s) and 3.13 (s)(3H), 3.4–3.7 (2H, m), 4.22 (d) and 4.29 (d)(J=14.5Hz, 1H), 4.71 (d) and 4.78 (d)(J=14.5Hz, 1H), 4.9–5.1 (1H, m), 5.61 (1H, t, J=7Hz), 6.8–7.6 (12H, m), 7.6–7.9 (2H, m), 7.64 (1H, s), 8.32 (d) and 8.39 (d)(J=8Hz, 1H)

Elemental Analysis. Calculated for C$_{34}$H$_{39}$N$_3$O$_5$ : C 71.68, H 6.90, N 7.38; Found : C 71.61, H 6.87, N 7.25.

EXAMPLE 55

The object compound was obtained according to a similar manner to that of Example 19.

IR (Nujol) : 3350, 1630, 1615, 1530, 1175, 900 cm$^{-1}$

NMR (DMSO-d$_6$, δ) : 1.9–2.1 (1H, m), 2.1–2.4 (1H, m), 2.31 (3H, s), 2.68 (s) and 2.73 (s)(3H), 2.7–3.1 (2H, m), 3.7–4.1 (2H, m), 3.83 (3H, s), 4.40 (2H, s), 4.7–5.0 (2H, m), 5.1–5.2 (1H, m), 6.9–7.4 (14H, m), 7.51 (1H, d, J=8Hz), 7.72 (2H, d, J=8Hz), 7.79 (1H, s), 8.00 (1H, d, J=8Hz), 8.55 (1H, br s)

EXAMPLE 56

The object compounds were obtained according to a similar manner to that of Example 38.

(1)

IR (Nujol) : 3230, 1625, 1525 cm$^{-1}$

NMR (DMSO-d$_6$, δ) : 1.7–2.1 (3H, m), 2.2–2.5 (3H, m), 2.67 (s) and 2.74 (s)(3H), 2.7–3.1 (2H, m), 3.5–3.7 (2H, m), 4.0–4.6 (4H, m), 4.6–4.8 (1H, m), 4.8–5.1 (1H, m), 6.9–7.4 (12H, m), 7.45 (1H, d, J=7Hz), 7.82 (1H, s), 8.00 (1H, d, J=8Hz), 8.4–8.7 (1H, m), 8.7–8.9 (1H, m), 11.73 (1H, s)

(2)

IR (Nujol) : 3400, 1625, 1540 cm$^{-1}$

NMR (DMSO-d$_6$, δ) : 2.6–2.9 (1H, m), 2.74 (s) and 2.79 (s)(3H), 3.0–3.3 (1H, m), 3.12 (s) and 3.15 s)(3H), 3.4–3.8 (2H, m), 3.84 (3H, s), 4.2–4.8 (2H, m), 4.9–5.2 (2H, m), 5.59 (1H, t, J=6Hz), 6.9–7.3 (12H, m), 7.50 (1H, d, J=8Hz), 7.76 (1H, d, J=8Hz), 8.09 (1H, s), 8.12 (1H, d, J=8Hz)

EXAMPLE 57

The object compound was obtained according to a similar manner to that of Example 22.

IR (Nujol) : 3200, 1630, 1525 cm$^{-1}$

NMR (DMSO-d$_6$, δ) : 1.6–2.0 (1H, m), 2.3–3.2 (3H, m), 2.68 (s) and 2.72 (s)(3H), 2.93 (3H, s), 3.5–4.3 (3H, m), 4.40 (2H, br s), 4.5–5.1 (2H, m), 6.9–7.55 (14H, m), 7.80 (1H, s), 7.9–8.1 (1H, m), 8.4–8.7 (1H, m), 11.62 (1H, s)

EXAMPLE 58

The object compound was obtained according to a similar manner to that of Example 36.

IR (Nujol) : 3220, 1660, 1640, 1630, 1525 cm$^{-1}$

NMR (DMSO-d$_6$, δ) : 1.22 (6H, t, J=7Hz), 1.7–1.9 (1H, m), 2.3–3.3 (14H, m), 4.0–4.6 (4H, m), 4.6–4.8 (1H, m), 4.8–5.1 (1H, m), 6.9–7.4 (12H, m), 7.46 (1H, d, J=7Hz), 7.80 (1H, s), 7.99 (1H, d, J=8Hz), 8.4–8.7 (2H, m), 10.39 (1H, br s), 11.77 (1H, s)

EXAMPLE 59

The object compound was obtained according to a similar manner to that of Example 40.

IR (Nujol) : 3200, 1630 (sh), 1600, 1525 cm$^{-1}$

NMR (DMSO-d$_6$, δ) : 1.75–1.9 (1H, m), 2.1–2.3 (1H, m), 2.69 and 2.77 (3H, s), 2.9–3.1 (2H, m), 3.59 (2H, s), 3.8–4.0 (2H, m), 4.23 (1H, m), 4.42 (2H, s), 4.69 (1H, m), 4.96 (1H, m), 7.0–7.3 (12H, m), 7.47 (1H, d, J=7.4Hz), 7.89 (1H, s), 8.06 (1H, d, J=7.3Hz), 8.45 (1H, m)

EXAMPLE 60

The object compound was obtained according to a similar manner to that of Example 41.

IR (Nujol) : 3400, 1600, 1530 cm$^{-1}$

NMR (DMSO-d$_6$, δ) : 1.83 (1H, m), 2.18 (1H, m), 2.70 and 2.77 (3H, s), 2.9–3.1 (2H, m), 3.58 (2H, s), 3.91 (2H, br), 4.19 (1H, m), 4.4–4.75 (5H, m), 4.96 (1H, m), 6.9–7.4 (13H, m), 7.87 (1H, br s), 8.04 (1H, m), 8.45 (1H, br)

EXAMPLE 61

The object compound was obtained according to a similar manner to that of Preparation 4.

IR (Nujol) : 3300, 1640, 1530 cm$^{-1}$

NMR (DMSO-d$_6$, δ) : 1.75–1.9 (1H, m), 2.06–2.2 (1H, m), 2.65 and 2.71 (3H, s), 2.8–3.5 (4H, m), 3.6–3.8 (3H, m), 4.25–4.6 (4H, m), 4.8–5.06 (2H, m), 6.4 (2H, br), 6.95–7.4 (14H, m), 8.59 (d, J=7.7Hz) and 9.03 (d, J=7.7Hz)(1H)

EXAMPLE 62

The object compound was obtained according to a similar manner to the latter half of Example 32.

IR (Nujol) : 3300, 1720, 1630, 1536 cm$^{-1}$

NMR (DMSO-d$_6$, δ) : 1.3–1.8 (4H, m), 2.3–2.5 (4H, m), 2.69 and 2.78 (3H, s), 2.9–3.3 (4H, m), 4.4–4.7 (3H, m), 4.85–5.2 (1H, m), 6.95–7.5 (13H, m), 7.7–7.9 (2H, m), 8.1–8.45 (3H, m), 11.6 (1H, s), 12 (1H, br)

EXAMPLE 63

To an ice-cooled solution of Starting Compound (0.45 g) in methanol (45 ml) was added 1N sodium hydroxide (0.75 ml) solution. The solution was stirred for two hours at room temperature. After concentration, the product was extracted with ethyl acetate and the organic layer was washed successively with water and sodium chloride solution, and was dried over magnesium sulfate. After evaporation of the solvent, the solid residue was washed with ethyl acetate, filtered and dried to give Object Compound (0.30 g).

mp 131°–136° C.

IR (Nujol) : 3440, 3275, 1720, 1660, 1630, 1605, 1580, 1635 cm$^{-1}$

NMR (DMSO-d$_6$, δ) : 1.7–2.1 (2H, m), 2.8–3.4 (4H, m), 3.5–4.0 (4H, m), 3.85 (3H, s), 4.2–5.2 (7H, m), 6.9–7.4 (12H, m), 7.48 (1H, d, J=8Hz), 7.88 (1H, s), 8.06 (1H, d, J=8Hz), 8.38 (1H, s)

What we claim is:

1. A compound of the formula:

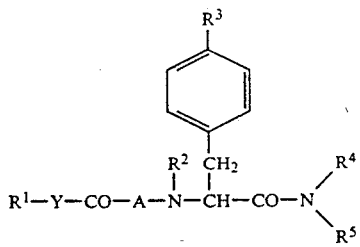

wherein
R[1] is lower alkyl, aryl, arylamino, pyridyl, pyrrolyl, pyrazolopyridyl, quinolyl, or a group of the formula:

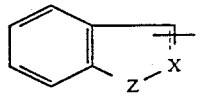

wherein
the symbol of a line and dotted line is a single bond or a double bond,
X is CH or N, and
Z is O, S or NH
each of which may have suitable substituent(s);
R[2] is hydrogen or lower alkyl;
R[3] is hydrogen or hydroxy;
R[4] is lower alkyl which may have suitable substituent(s), and
R[5] is ar(lower)alkyl which may have suitable substituent(s) or pyridyl(lower)alkyl, or
R[4] and R[5] are linked together to form benzene-condensed lower alkylene;
A is a bivalent residue derived from an amino acid selected from the group consisting of proline, hydroxyproline, glycine, serine, asparagine, aminoisobutyric acid, azetidinecarboxylic acid, thioproline, aspartic acid, lysine, methionine, threoine, alanine ornithine, hydroxypiperidinecarboxylic acid, 4-acyloxyproline, 4-lower alkoxyproline, 4-carboxy(lower)alkoxyproline, 4-esterified carboxy(lower)alkoxyproline, 4-lower alkylthioproline, 4-aminoproline, 4-acylaminoroline, O[3]-lower alkylserine, O[3]-ar(lower)alkylserine, thioproline sulfoxide, thioproline sulfone, O[4]-ar(lower)alkyl hydrogen aspartate, (carbamoyl and hydroxy substituted lower alkylamino)-β-aspartate, carbamoyl(lower)alkylamino-β-aspartate, morpholine-β-aspartate, (carbamoyl and lower alkylcarbamoyl substituted lower alkylamino)-β-aspartate, N[6]-acyllysine, and N[5]-acylornithine, and
Y is bond, lower alkylene or lower alkenylene, or a pharmaceutically acceptable salt thereof.

2. A compound of claim 1, wherein
R[1] is lower alkyl, aryl which may have one to three substituent(s) selected from the group consisting of hydroxy, lower alkoxy and N,N-di(lower)alkylamino, arylamino, pyridyl, pyrrolyl, pyrazolopyridyl, quinolyl, benzofuryl, benzothienyl, and a group of the formula:

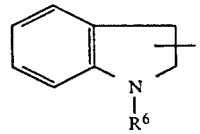

wherein R[6] is hydrogen or esterified carboxy, or a group of the formula:

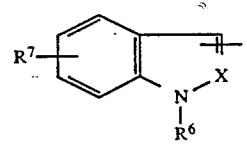

wherein
X is CH or N,
R[6] is hydrogen, lower alkyl, carboxy(lower)alkyl, esterified carboxy(lower)alkyl, N,N-di(lower)alkylamino(lower)alkyl or N,N-di(lower)alkylamino(lower)alkylcarbamoyl(lower)alkyl and
R[7] is hydrogen, hydroxy, halogen, lower alkyl, lower alkoxy, N,N-di(lower)alkylamino or acyl,
R[2] is hydrogen or lower alkyl,
R[3] is hydrogen or hydroxy,
R[4] is lower alkyl, hydroxy(lower)alkyl or acyloxy(lower)alkyl,
R[5] is ar(lower)alkyl, haloar(lower)alkyl, halo(lower)alkylar(lower)alkyl or pyridyl(lower)alkyl, or
R[4] and R[5] are linked together to form benzene-condensed lower alkylene,
A is a bivalent residue derived from an amino acid selected from the group consisting of proline, hydroxyproline, glycine, serine, asparagine, aminoisobutyric acid, azetidinecarboxylic acid, thioproline, aspartic acid, lysine, methionine, threonine, alanine, ornithine, hydroxypiperidinecarboxylic acid, 4-acyloxyproline, 4-lower alkoxyproline, 4-carboxy(lower)alkoxyproline, 4-esterified carboxy(lower)alkoxyproline, 4-lower alkylthioproline, 4-aminoproline, 4-acylaminoproline, O[3]-lower alkylserine, O[3]-ar(lower)alkylserine, thioproline sulfoxide, thioproline sulfone, O[4]-ar(lower)alkyl hydrogen aspartate, (carbamoyl and hydroxy substituted lower alkylamino)-β-aspartate, carbamoyl(lower)alkylamino-β-aspartate, morpholine-β-aspartate, (carbamoyl and lower alkylcarbamoyl substituted lower alkylamino)-β-aspartate, N[6]-acyllysine, and N[5]-acylornithine, and
Y is bond, lower alkylene or lower alkenylene.

3. A compound of claim 2, wherein
R[1] is lower alkyl, aryl which may have one to three substituent(s) selected from the group consisting of hydroxy, lower alkoxy and N,N-di(lower)alkylamino, arylamino, pyridyl, pyrrolyl, pyrazolopyridyl, quinolyl, benzofuryl, indazolyl, benzothienyl, and a group of the formula:

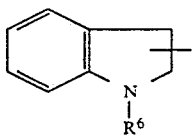

wherein $R^6$ is hydrogen or lower alkoxycarbonyl, or a group of the formula:

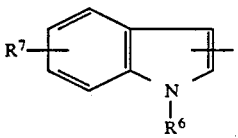

wherein
- $R^6$ is hydrogen, lower alkyl, carboxy(lower)alkyl, lower alkoxycarbonyl(lower)alkyl, N,N-di(lower)alkylamino(lower)alkyl or N,N-di(lower)alkylamino(lower)alkylcarbamoyl(lower alkyl, and
- $R^7$ is hydrogen, hydroxy, halogen, lower alkyl, lower alkoxy or N,N-di(lower)alkylamino or lower alkoxycarbonyl, and
- $R^4$ is lower alkyl, hydroxy(lower)alkyl or lower alkanoyloxy(lower)alkyl,
- $R^5$ is ar(lower)alkyl, haloar(lower)alkyl, halo(lower)alkylar(lower)alkyl or pyridyl(lower)alkyl, or
- $R^4$ and $R^5$ are linked together to form benzene-condensed lower alkylene,
- A is a bivalent residue derived from an amino acid selected from the group consisting of proline, 4-hydroxyproline, glycine, serine, asparagine, 2-aminoisobutyric acid, azetidine-2-carboxylic acid, thioproline, aspartic acid, lysine, methionine, threonine, alanine, ornithine, 5-hydroxypiperidine-2-carboxylic acid, 4-lower alkanoyloxyproline, 4-lower alkanesulfonyloxyproline, 4-arenesulfonyloxyproline, 4-carbamoyloxyproline, 4-lower alkoxyproline, 4-carboxy(lower)alkoxyproline, 4-lower alkoxycarbonyl-lower alkoxyproline, 4-lower alkylthioproline, 4-aminoproline, 4-carboxy(lower)alkanoylaminoproline, 4-amino(lower)alkanoylaminoproline, 4-ar(lower)alkoxycarbonylamino(lower)alkanoylaminoproline, 4-amino and carboxy substituted lower alkanoylaminoproline, 4-ar(lower)alkoxycarbonylamino and ar(lower)alkoxycarbonyl substituted lower alkanoylaminoproline, 4-oxaloaminoproline, 4-lower alkoxyalaminoproline, 4-lower alkanesulfonylaminoproline, 4-N,N-di(lower)alkylamino(lower)alkanoylaminoproline, $O^3$-lower alkylserine, $O^3$-ar(lower)alkylserine, thioproline sulfoxide, thioproline sulfone, $O^4$-ar(lower)alkyl hydrogen aspartate, (carbamoyl and hydroxy substituted lower alkylamino)-β-aspartate, carbamoyl(lower)alkylamino-β-aspartate, morpholino-β-aspartate, (carbamoyl and lower alkylcarbamoyl substituted lower alkylamino)-β-aspartate, $N^6$-ar(lower)alkoxycarbonyllysine, $N^6$-haloar(lower)alkoxycarbonyllysine, $N^6$-N,N-di(lower)alkylamino-lower alkanoyllysine, $N^6$-morpholinocarbonyllysine, $N^6$-N-lower alkoxycarbonyl-N-lower alkoxycarbonyl(lower)alkylamino(lower)alkanoyllysine, $N^6$-(hydroxy and lower alkanoylamino substituted lower alkanoyl)lysine, $N^6$-(hydroxy and lower alkoxycarbonylamino substituted lower alkanoyl)lysine, $N^6$-lower alkoxycarbonylamino(lower)alkanoyllysine, $N^6$-amino(lower)alkanoyllysine, $N^5$-ar(lower)alkoxycarbonylornithine, $N^5$-(hydroxy and lower alkanoylamino substituted lower alkanoyl)ornithine, and $N^5$-(hydroxy and lower alkoxycarbonylamino substituted lower alkanoyl)ornithine.

4. A compound of claim 3, wherein
$R^1$ is indazolyl or a group of the formula:

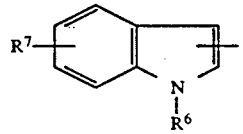

wherein
- $R^6$ is hydrogen, lower alkyl, carboxy(lower)alkyl, lower alkoxycarbonyl(lower)alkyl, N,N-di(lower)alkylamino(lower)alkyl or N,N-di(lower)alkylamino(lower)alkylcarbamoyl(lower)alkyl, and
- $R^7$ is hydrogen, hydroxy, halogen, lower alkyl, lower alkoxy or N,N-di(lower)alkylamino,
- $R^4$ is lower alkyl, hydroxy(lower)alkyl or lower alkanoyloxy(lower)alkyl,
- $R^5$ is phenyl(lower)alkyl, halophenyl(lower)alkyl, halo(lower)alkylphenyl(lower)alkyl or pyridyl(lower)alkyl, and
- A is a bivalent residue derived from an amino acid selected from the group consisting of proline, 4-hydroxyproline, glycine, serine, asparagine, 2-aminoisobutyric acid, azetidine-2-carboxylic acid, thioproline, aspartic acid, lysine, methionine, threonine, alanine, ornithine, 5-hydroxypiperidine-2-carboxylic acid, 4-lower alkanoyloxyproline, 4-lower alkanesulfonyloxyproline, 4-phenylsulfonyloxyproline, 4-carbamoyloxyproline, 4-lower alkoxyproline, 4-carboxy(lower)alkoxyproline, 4-lower alkoxycarbonyl-lower alkoxyproline, 4-lower alkylthioproline, 4-aminoproline, 4-carboxy(lower)alkanoylaminoproline, 4-amino(lower)alkanoylaminoproline, 4-phenyl(lower)alkoxycarbonylamino(lower)alkanoylaminoproline, 4-amino and carboxy substituted lower alkanoylaminoproline, 4-phenyl(lower)alkoxycarbonylamino and phenyl(lower)alkoxycarbonyl substitited lower alkanoylaminoproline, 4-oxaloaminoproline, 4-lower alkoxalylaminoproline, 4-lower alkanesulfonylaminoproline, 4-N,N-di(lower)alkylamino(lower)alkanoylaminoproline, $O^3$-lower alkylserine, $O^3$-phenyl(lower)alkylserine, thioproline sulfoxide, thioproline sulfone $O^4$-phenyl(lower)alkyl hydrogen aspartate, (carbamoyl and hydroxy substituted lower alkylamino)-β-aspartate, carbamoyl(lower)alkylamino-β-aspartate, morpholino-β-aspartate, (carbamoyl and lower alkylcarbamoyl substituted lower alkylamino)-β-aspartate, $N^6$-phenyl(lower)alkoxycarbonyllysine, $N^6$-halophenyl(lower)alkoxycarbonyllysine, $N^6$-N,N-di(lower)alkylamino-lower alkanoyllysine, $N^6$-morpholinocarbonyllysine, $N^6$-N-lower alkoxycarbonyl-N-lower alkoxycarbonyl(lower)alkylamino(lower)alkanoyllysine, $N^6$-(hydroxy and lower alkanoylamino substituted lower alkanoyl)lysine, $N^6$-(hydroxy and lower alkoxycarbonylamino substituted lower alkanoyl)lysine, $N^6$-lower alkoxycarbonylamino(-lower)alkanoyllysine, $N^6$-amino(lower)alkanoyllysine, $N^5$-phenyl(lower)alkoxycarbonylornithine, $N^5$-(hydroxy and lower alkanoylamino substituted lower alkanoyl)ornithine, and $N^5$-(hydroxy and lower alkoxycarbonylamino substituted lower alkanoyl)ornithine.

5. A compound of claim 4, wherein
$R^1$ is indazolyl or a group of the formula:

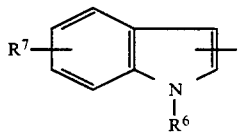

wherein
$R^6$ is hydrogen, methyl, isopropyl, carboxymethyl, t-butoxycarbonylmethyl, N,N-dimethylaminoethyl or N,N-dimethylaminoethylcarbamoylmethyl, and
$R^7$ is hydrogn, hydroxy, chloro, methyl, methoxy or N,N-dimethylamino,
$R^2$ is hydrogen or methyl,
$R^3$ is hydrogen or hydroxy,
$R^4$ is methyl, hydroxyethyl or acetyloxyethyl,
$R^5$ is benzyl, fluorobenzyl, chlorobenzyl, trifluoromethylbenzyl or pyridylmethyl,
A is selected from the group consisting of Pro, D—Pro, Pro(4OH), Gly, Ser, Asn, Aib, Azt, Tpr, Asp, Lys, Met, Thr, Ala, Orn, Tpr(O), Tpr(O$_2$), Pro(4OCH$_2$CO$_2$Bu$^t$), Pro(4OMs), Pro(4NH$_2$), 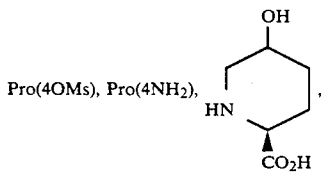

Pro(4NHCOCO$_2$Et), Pro(4OCONH$_2$), Asp(OBzl),

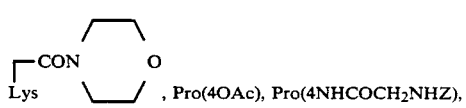

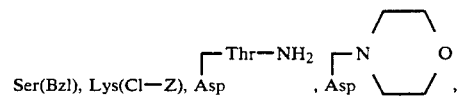

Pro(4NHCOCH$_2$NH$_2$), Pro(4NHCO(CH$_2$)$_2$CHCO$_2$Bzl),
|
NHZ

-continued
Pro(4NHCO(CH$_2$)$_2$CHCO$_2$H), Pro(4NHCO(CH$_2$)$_2$CO$_2$H),
|
NH$_2$ Pro(4NHCOCO$_2$H), Pro(4OTs), Pro(4SMe), Pro(4OMe),

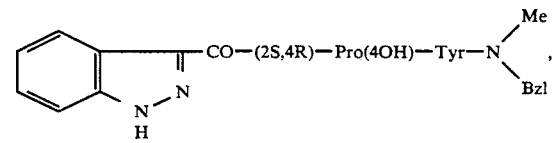

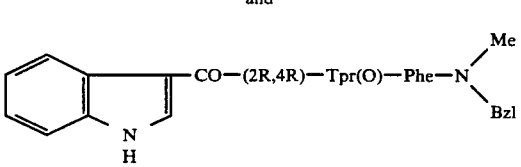

Pro(4NHCOCH(CH$_2$)$_2$CO$_2$Bzl), Ac—Thr┐ ,
|                                    Orn
NHZ

H-βAla┐      H—Gly┐
      Lys,         Lys, Pro(4OCH$_2$CO$_2$H),

Pro(4NHCOCH(CH$_2$)$_2$CO$_2$H), Pro(4NHMs),
|
NH$_2$

Pro(4NHCO(CH$_2$)$_2$NEt$_2$), Pro(4OCH$_2$CO$_2$Et) or

┌CO(CH$_2$)$_2$CO$_2$H
Orn                   ;

and
Y is bond, methylene, ethylene, trimethylene, or vinylene.

6. A compound of claim 5, wherein
$R^1$ is indazolyl or imidazolyl,
$R^2$ is hydrogen,
$R^3$ is hydrogen or hydroxy,
$R^4$ is methyl,
$R^5$ is benzyl, and
Y is bond.

7. A compound of claim 6, which is selected from the group consisting of:

[Structure: indazole—CO—(2S,4R)—Pro(4OH)—Tyr—N(Me)(Bzl)]

and

[Structure: indole—CO—(2R,4R)—Tpr(O)—Phe—N(Me)(Bzl)]

8. A pharmaceutical composition which comprises a compound of claim 1 and a pharmaceutically acceptable carrier or excipient.

9. A method for treating tachykinin mediated diseases which comprises administering an effective amount of a compound of claim 1 to an individual in need thereof.

10. The method of claim 9 wherein said effective amount is effective to cause Substance P antagonism.

* * * * *